(12) United States Patent
Manjunath et al.

(10) Patent No.: US 12,024,711 B2
(45) Date of Patent: Jul. 2, 2024

(54) METHODS AND COMPOSITIONS FOR GENERATING DOMINANT SHORT STATURE ALLELES USING GENOME EDITING

(71) Applicant: MONSANTO TECHNOLOGY LLC, St. Louis, MO (US)

(72) Inventors: Sivalinganna Manjunath, Chesterfield, MO (US); Linda A. Rymarquis, High Ridge, MO (US); Thomas L. Slewinski, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 201 days.

(21) Appl. No.: 17/613,115

(22) PCT Filed: May 28, 2020

(86) PCT No.: PCT/US2020/034993
§ 371 (c)(1),
(2) Date: Nov. 22, 2021

(87) PCT Pub. No.: WO2020/243361
PCT Pub. Date: Dec. 3, 2020

(65) Prior Publication Data
US 2022/0195445 A1    Jun. 23, 2022

Related U.S. Application Data

(60) Provisional application No. 62/886,726, filed on Aug. 14, 2019, provisional application No. 62/854,142, filed on May 29, 2019.

(51) Int. Cl.
| | | |
|---|---|---|
| C12N 15/82 | (2006.01) | |
| C12N 9/00 | (2006.01) | |
| C12N 9/02 | (2006.01) | |

(52) U.S. Cl.
CPC ....... *C12N 15/8218* (2013.01); *C12N 9/0071* (2013.01); *C12N 15/8213* (2013.01); *C12N 15/8262* (2013.01); *C12Y 114/11012* (2013.01)

(58) Field of Classification Search
None
See application file for complete search history.

(56) References Cited

U.S. PATENT DOCUMENTS

| | | |
|---|---|---|
| 2004/0060080 A1 | 3/2004 | Tanaka et al. |
| 2007/0209085 A1 | 9/2007 | Wu et al. |
| 2015/0052634 A1 | 2/2015 | Park et al. |
| 2018/0051295 A1 | 2/2018 | Allen et al. |
| 2018/0105824 A1 | 4/2018 | Simmons et al. |
| 2020/0029538 A1 | 1/2020 | Mashimo et al. |

FOREIGN PATENT DOCUMENTS

| | | |
|---|---|---|
| EP | 3546575 A1 | 10/2019 |
| WO | 199428141 A1 | 12/1994 |
| WO | 2006013072 A2 | 2/2006 |
| WO | 2015117041 A1 | 8/2015 |
| WO | 2017143061 A1 | 8/2017 |
| WO | 2018035354 A1 | 2/2018 |
| WO | 2018080389 A1 | 5/2018 |
| WO | 2018097257 A1 | 5/2018 |
| WO | 2018119225 A1 | 6/2018 |
| WO | 2019036599 A1 | 2/2019 |
| WO | 2019089884 A2 | 5/2019 |
| WO | 2019161146 A1 | 8/2019 |
| WO | 2020117553 A1 | 6/2020 |

OTHER PUBLICATIONS

GenBank. (2014) GenBank Accession No. AC209074, "Zea mays Cultivar B73 Chromosome 8 Clone CH201-426A6," 40 pages.
International Search Report and Written Opinion, dated Nov. 2, 2020, for PCT Application No. PCT/US2020/034993, filed May 28, 2020, 14 pages.
International Search Report and Written Opinion, dated Oct. 19, 2020, for PCT Application No. PCT/US2020/034996, filed May 28, 2020, 19 pages.
International Search Report and Written Opinion, dated Oct. 23, 2020, for PCT Application No. PCT/US2020/035001, filed May 28, 2020, 25 pages.
Kraft, K. et al. (2015) "Deletions, Inversions, Duplications: Engineering of Structural Variants using CRISPR/Cas in Mice," Cell Reports 10:833-839.
Nakamura, T. et al. (Jul. 2012, e-pub May 9, 2012). "Mechanistic Insight Into Pentatricopeptide Repeat Proteins as Sequence-Specific RNA-Binding Proteins for Organellar RNAs in Plants," Plant and Cell Physiology 53(7): 1171-1179.
Nicholson, S. J. (2009) "Transgene Constructs Lacking Transcription Termination Signal Induce Efficient Silencing of Endogenous Targets in *Arabidopsis*," Mol. Genet. Genomics, 282:319-328.
Soininen, R. et al. (1988) "The Structural Genes for a 1 and a2 Chains of Human Type IV Collagen are Divergently Encoded on Opposite DNA Strands and Have an Overlapping Promoter Region," The Journal of Biological Chemistry, 263(33): 17217-17220.
Yan, H. et al. (Aug. 2006) "New Construct Approaches for Efficient Gene Silencing in Plants," Plant Physiology, 141:1508-1518.

(Continued)

*Primary Examiner* — Brent T Page
(74) *Attorney, Agent, or Firm* — Morrison & Foerster LLP

(57) ABSTRACT

The present disclosure provides compositions and methods for altering gibberellin (GA) content in corn or other cereal plants. Methods and compositions are also provided for altering the expression of genes related to gibberellin biosynthesis through editing of specific subtypes of GA20 oxidase genes to introduce an antisense sequence or segment into the gene. Modified plant cells and plants having a dominant allele reducing the expression or activity of one or more GA oxidase genes are further provided comprising reduced gibberellin levels and improved characteristics, such as reduced plant height and increased lodging resistance, but without off-types.

44 Claims, 6 Drawing Sheets
Specification includes a Sequence Listing.

(56) References Cited

OTHER PUBLICATIONS

Hahn, F. et al. (Jul. 5, 2017). "Generation of Targeted Knockout Mutants in *Arabidopsis thaliana* Using CRISPR/Cas9," Bio Protoc. 7(13): e2384, 20 pages.

Kasim, V. et al. (2004, e-pub Apr. 23, 2004). "Control of siRNA Expression Using the Cre-loxP Recombination System," Nucleic Acids Res. 32(7):e66, 8 pages.

Lynagh, P. G. et al. (e-pub Aug. 26, 2018). "Translocation and Duplication from CRISPR-Cas9 Editing in *Arabidopsis thaliana*," BioRxiv, 34 pages.

Qi, Y. et al. (Oct. 2013, e-pub Oct. 1, 2013). "Targeted Deletion and Inversion of Tandemly Arrayed Genes in *Arabidopsis thaliana* Using Zinc Finger Nucleases," G3 (Bethesda) 3(10):1707-1715.

Köllner, T. G. et al. (Aug. 2010). "Herbivore-induced SABATH Methyltransferases of Maize that Methylate Anthranilic Acid Using S-Adenosyl-L-Methionine," Plant Physiol. 153(4):1795-1807.

```
                        SEQUENCE LISTING

<160> NUMBER OF SEQ ID NOS: 36

<210> SEQ ID NO 1
<211> LENGTH: 8800
<212> TYPE: DNA
<213> ORGANISM: zea mays

<400> SEQUENCE: 1
taaatttgtg atccttgtga agttgttata tcatgaattg tgaacttgtt gcatttgtga      60
tcttttgtca actttgttgt attgtgaagt ttgatatgtt taccgatcgt attttagatt     120
tcgatcgtta ccggtgtatt ttccgcacca aactttgtt tccgatgttt tcgaaatacc      180
gatatcgttt ccgtttctat agttaccctt ttcaatttta tttccgatta aaaatatgaa     240
aacggtaatg gttttagtgt ttatcgaccg ttttcatctc taatcatccc tgccggtgaa     300
gtttaatttt tcccttggct aaagagatgc aagctgctgt aaaatacgtt aaaacaggca     360
aggcagcccc agcagccagc atcgcgtgcc cgtctatgta catcagtgga tacgtagcat     420
ctctagtgag taatataacg attgcatttg gctggaggac gtatgttata taagtatgtc     480
atttaccagt tgcattagta tcttccctaa ctcctataat aactctcttc gtggaatgga     540
cgtagacgta tgctatataa gtattaaaaa atagtttttt aagctggtgt cctcaatttt     600
gctattgttc tcgtttttat ctttagttgt gtcacaaatt taatccgtac aacaaatcaa     660
aaataccata cccttcttat attaattttc taacataaca tttgtttaga tattttcagt     720
cgtgaaaata caattctaat tctaacgtcg tagtatcaaa tcaaaccatc cagaatttga     780
ccaagcttaa ttataaaaaa tataaaattt atgatactga atagatagca ttagatttgt     840
tatataatat atttttataa aataccattt ttatggtata aatattggta ctcctttact     900
ttaaactata gatagttttg actaaggatg caactagaat tgcatcctct tttcactgca     960
ccttcattag ttttaatatt tatttagatg ggcccttgca aactgtagat atcatctctt    1020
gcaacattct ttctatagca ccacgaaaat gtattgcggc tttgaaatta taattgaatt    1080
agttgtatca tttctttcac cgatgcgtta aattcaaaat taagtgttat atttcttcat    1140
aatttgttaa atatatagac cctataatcc accattattt actataatag catacattaa    1200
cattggtttt agcctacact acgacactcg aggcattgaa ttttcctcta tcaaagaatt    1260
atatgtgtag tagtattgtt cttgacaaaa aggggatta aaattaaact accaatattg    1320
atacttatct tatcacatcc atgaatacaa tcaacactct tacaaaagat aagatacaag    1380
attaaaaagt accatgataa tacattaaga ttattagcaa tgcattaaat taaataaatg    1440
tgcaagtgaa tcatgatttt agttttatct attttactt taaaatatga tattctctga    1500
ctacttctaa gcataaatgt gattctaagt catgaccgat cgtgcttatt cagaaaaatg    1560
```

```
aaggagacac agatttctat aaaaaaaggt tgtcatggga ctattgggtc aaccatctta    1620
ttcatttggg aaaataagtt tagaacacat caacccattt tagatgttga gtttggccct    1680
aatggtccat tgaccttact tttgtgggtt gacatagacc atctatccca agttattgtt    1740
gtgtcacatt ccctgatatc atgaatctat attttagctt tccgttttca tattttttagt   1800 cgttacatat tttttatccg cgtactagat taaaactcta gttgttgcaa tacattttgt    1860 tcatttttt ctatttcttc tttactaaca acatattcta gttcctagct acattcttaa    1920
gtaccatagt gctataaaca ttttttatcc tacattattc cacttaagaa attgaattt    1980 ctgcataaaa aaattatatg tccagtagtg ttgtcttata aaagcataaa gtgattaaaa    2040
ttaaaaccat tattgatatc ttattttca aaaaaaata taagcttata gaaagtgaat    2100
taatttcatg gtaaattaat atagtttaaa ttgaattatt agtgttatta ctatgtttat    2160
tatcaatgaa acattttca tggttgatat aacttagtgt tacttatttt agtattttt    2220 atataattct agttaacttt tagttttga tttaaaaaaa cgagaattgt gtccttttgt    2280
ggagtgagta taaagaaagt aatatctgtt catcataatt tggtttttta aggtacgtga    2340
aacttgcttt atatttggac tcaagctatg tctaaataca tagtaaaaaa gcaatatttc    2400
tagaaaagac aaaacatctt ataatttaga atcaaggaaa tatatagatt ttatgtgcag    2460
tgagaagcca tttacaatgg aacgttcaac gttgggccaa tagatatttt gcgatatgat    2520
gatgggcata tttttgcatg gttgtccctc cactagctat agtttgatga tacgatacgc    2580
tgcacacacc attgggttgt accatgttag tgtagcaaca gtagaaaccc aattgtggcc    2640
gtgaaccatg ataatactag gtagagtgct agctagaggt ttcaggctat tgatgcgtga    2700 attaaactt ctgttgtgtt gcgaggaaac gagtattgtg aaatatttga aacggttttt    2760
tttgtgaaag atttgaaacg gtattttgt tgtgaaataa agatcaaggc taaataaatt    2820
caaactaata aaacatatta attgacggcc tgaagccccc gccccatgg ccccatgcca    2880 tagcatcagg tcccacatga catgaggccg cgcctccctc tatgttggct ccctgccttc    2940
gccgttgtcg tcgctcccga actccctctc ctcccctgtt acaaatacc ccacccgccc    3000 ggacagcttc cctgcacact cgcagctcgc acatctcatg gtgtcctaag aacggcaaga    3060
gccagctctg cctagcagca gcgcacagcc acatccatgg acgccagccc gaccccaccg    3120 ctcccctcc gcgccccaac tcccagcatt gacctccccg ctggcaagga cagggccgac    3180
gcggcggcta acaaggccgc ggctgtgttc gacctgcgcc gggagcccaa gatcccggag    3240
ccattcctgt ggccgcacga agaggcgcgg ccgacctcgg ccgcggagct ggaggtgccg    3300
gtggtggacg tgggcgtgct gcgcaatggc gacggcgcgg ggctccgccg cgccgcggcg    3360
caagtggcgc cggcgtgcgc gacgcacggg ttcttccagg tgtgcgggca cggcgtggac    3420
gcggcgctgg ggcgcgccgc gctggacggc gccagcgact tcttccggct gccgctggct    3480
gagaagcagc gggcccggcg cgtccccggc ccgtgtccg ggtacacgag cgcgcacgcc    3540
gaccggttcg cgtccaagct cccctggaag gagaccctgt ccttcggctt ccacgacggc    3600
gccgcggcgc ccgtcgtcgt ggactacttc accggcaccc tcggccaaga tttcgagcca    3660
gtggggtgag taaagaagaa gatggcgccg aatttacatt tataagtagg accagcagaa    3720 gccctgccc ctgggggcct tagcattgca ttcgactgat gaatacgcat ggcaggcggg    3780
tgtaccagag gtactgcgag gagatgaagg agctgtcgct gacgatcatg gagctgctgg    3840
agctgagcct gggcgtggag cgcggctact accgggagtt cttcgaggac agccgctcca    3900
```

```
tcatgcggtg caactactac ccgccgtgcc cggtgccgga gcgcacgctg ggcacgggcc      3960
cgcactgcga ccccacggcg ctgaccatcc tcctgcagga cgacgtcggc gggctggagg      4020
tcctggtgga cggcgagtgg cgccccgtcc ggcccgtccc aggcgccatg gtcatcaaca      4080
tcggcgacac cttcatggta acgaacgaaa gcgccggctc ctctgctttt cttggcctct      4140
ttgtccctgc cctgtgctgc tgtgcatatt cattcattca gttctctgtg ggtttttttt      4200
tttgtttaat ttttttttgg gatcgtatcc agtgcacaag gccacgccg tgcacaaatg       4260 cacaaaacga aatctggccg tccatttttcc atccaacgac atgacggcgc gggggttt      4320 tcacaaaaca gactcggcaa gctacggagg ttgcgggagg gttcatctgc atatttacga      4380
cggccgttgg atggaaaatg gacggccaga tttcgttttg tgtatttgtg cacggcgtgg      4440
cccttgtgca ctggatacga tcccatttttt tttttttgccc cgaatcctag tggacctaac      4500
tggacagatt acagcacgca cacgtaggca tgtcatgtag cagcactgca gtcgggtgca      4560
gtccagtcca gtcctgtcca gccgcgacac tgtagtacat agcgatgcaa cggagacacg      4620
cgttggagtt ggttccatct cttctcggcg gccgtgccga ggcttccgcg gggaagctgc      4680
gacaacagaa cggaccgccg ggggtgggca ggcagcaagc tccctgttgg cttgtgccgt      4740
tgcgcagcgg cgggtaccgg acaacgcttt cggcggcgcg cggcctcgtc ggcttccct       4800 gtttttgatg ccgcctctcg gtgtccgggg accgggagga tcgatggggc ccgtgccgtc      4860
tgatccgcca cgcgagcggt cctatgcgat gcgccgcacg agcgcggggg ggccgtggaa      4920
cagtacacag ctgggtcact cactcactca tcccgctggt tgtggctgct tggttgcaac      4980
ttggctcggt tgtctgtctg ttgccccccgc cgcgttttct agccgtttcc gctttgctcg      5040
cggtttcgct ggcgatccgg cacgcggcgc ccacacccgg ggctggcccc ttggccgagt      5100
gggtggcagg cacttgcatg catccggccg gtttcccgcg accaagctgg cccgccgcaa      5160
caatgagagt gagacgagac tttgtgtcag tgtgtgtatg tacatgtatg tctgcgcgac      5220
agccctaccg tccgacacga tgattcttgt gcactgtact gtactgtact aactcccccc      5280
accccctccg gtatgtaacg catgccatat gcaggcgctg tccaacgggc ggtacaagag      5340
ctgcctgcac cgcgcggtgg tgaaccggcg gcaggagcgg caatcgctgg ccttcttcct      5400
gtgcccgcgc gaggaccggg tggtgcgccc gccggccagc gccgcgccgc ggcagtaccc      5460
ggacttcacc tgggccgacc tcatgcgctt cacgcagcgc cactaccgcg ccgacacccg      5520
cacgctggac gccttcaccc gctggctctc ccacggcccg gcggcggcgg ctccctgcac      5580
ctaacgagcc ggccgtctct ttcgccgggg cccgcgcggg gttcgcccac gtggtgatca      5640
ggtggcagac atgtggccca cgggccccgc gccgccttcc ccattttgg acgaccctac       5700 tgctactact actagtgtac atatgcaaaa aaatacatat atatataggt actttctcta      5760 atattttat atataagcaa ggcggcctgg tgttcttttc tttgttttgt cgacaactgt       5820
ttgatcccat cctatggacg atggatagtt caatgtttgt acgtacgtaa ctactctcta      5880
tagactagaa tgggctcatg aaactggacc gatcgacacg gacgtcacgt gcgtctggta      5940
ccggtagtgc aacgggtgcc gaatgtttgc tgggcccgga cgagaatcgc ttctcctcgt      6000
cctcggtcct caccctgaac gaacgaataa ggaaaatgct gcaccgaaag ctccagacgt      6060
ttccgaattc caaattccaa aaccccaaat cttcttgctt cacatcagtc ttacccggtt      6120
catctgtgac aaaaaaaaaa tagtgctagt ttaggaactc aggtcgagat tgaaggcaat      6180
tgtggaggaa tttaccctat aatccttatg agaatttgag ttcccaaact aactgagttg      6240
gagcattcaa catttcccta aattttgtgc acatgtttct ttgctattta tctttggaca      6300
```

```
tgggacgatg ggagacgcag atttagggga cccttcaatt cagaacttca ggtgcacaaa    6360
ccgaggttgg cttgcctgca ttcttgtttc ggacatgccc aactaggcca ctactcacta    6420
ccttcatctg agataccaat tgctgaccta aatgacaagt atacacttac atttcagtga    6480
tagctgcaac aaaaaaaaaa atcttaccgc attttatctc tgcattctgc atgccgcatc    6540
ctgaacatta cgtatctttc ccggtgctct gttgcgttct cacgcagttg atggcatgca    6600
gtcttgcgcc accgaatcca gtgtactggt cgtggtgact tgtcgcacag acagcagccc    6660
ggcagcacca agcgtgtcac tgtaaactgt tgggcgttaa acaacaactt gcacaacagc    6720
tcaaatatgg catatgctat ccgacaaact gaacaaggtg cccaattgat ctgaatgtac    6780
ctgtgatttc cagcactatc gtacagcaac gttgtcaaaa caagtggggt ggggttgggg    6840
acagattttt tcgataaaga agcttttata aaaaataaca atgatacaaa tcctgggtta    6900
tagatgtaca gaaagcacga agcacgaaag tccagtccaa agcacgtttt tttgcctggt    6960
actagcccga tccggccggc acgaataagc gggtcgagct cggacgggaa gctaagcacg    7020
acggactagc ccgacacgac ccgtttacct ctaatcccgt taaaccogct tttttgcact    7080 aaaccgtgct taccgaaccg tttagcccgt tttttggcct gattttttcgt gcttaacggg    7140 ccaggctcgg acaaggaaac aagcccgcgg gcttagacga tccggcctgg ttttttaacc    7200
gtgcctagcg ggtcgagccc aaaataggtc gggcttcact gggcccgagc cgggcgaccc    7260
gtttggccat ctctaacctg agtacaactt ccgacttctg caaaatacat acagccaaat    7320
aaaagaaaag taaaaagatc taaaaaatct cagctagaaa caatcaatcc gaagactaga    7380
tcgcctccca taagtctgga aaaagagac catggccact tgcaccaaga tgtgtgcatt    7440
attctacggt tacaccaaag atttttgttc tttaagggct agtttgggaa ccataatttt    7500
caaagggatt tctattttcc taaggaaaat tagttcattt ttccataaga aattagaaat    7560
ccattggaaa attgtggttc tcaaactagc cctaagcgtc gaaagaacc atatgcatat    7620 ctagagacaa aattcctcta atttctattc aggcttcagc acatatactt cacgtgcttg    7680
cgtcaagttc cttgggccgc cacatggact tatggacttc tcgacgcagc gaaagccgtc    7740
gttgcccttg gtgtagctag gtcatccgca cctcccactg gccagtggcc actgcaggga    7800
cttggccatg ggcttgtttg gttcagcttt tttctgacca gcttttctga aaatctggct    7860
gtgtgaagaa tctggctgtg agagaatctg agtatcatta cgattacgtg tggatgaaga    7920
taaagttgtt catagggctc aggatctaga aagtgacgga ttcctactat tacaatgact    7980
caaccgatta tgtgtttatg ttgatttttgg atgattttttg ccccaacaaa ttttatagaa    8040
gctggctgaa aagctgagcg tttggcagtc cacaacagtt tttggtggcc agaagctgcc    8100
agaagccgat acaaacaggg tccatgcttt ccatttcgtt taccgtgtac gcggtgtccc    8160
tcacaatcaa tcagtttacc ttgtggctcc aacacacatc aacctcggca caacaacact    8220
gtgaatcatt ttcggcggtc catattattt tcgacggttc atccctggcc gccgaaaatt    8280
gtctgttatt ttcggcggct tgacctagcc gtcgaaaata ggctgctatt ttcggcggcc    8340
aaatccgagc cgccgaaaat aaggctttta aaaaccgtcg gctccttctt cttctctgtt    8400 cttttctctcc tctcccaaag cccgccgccg ctcacccgcc gctcgctcgc cgggctgccc    8460
gccactccgc cgtcgtcgtc gagccaccgc atcgagaggt aaatttttttt tgcgtgtttt    8520 attccttatt ttcggcggtt gatatttagg cgccgccaaa attagtgtat atttgtaatt    8580
gtgtttgttt aattactatt tgtaattagt attattgttt aattcgattt cattaatgta    8640
```

| | |
|---|---:|
| ttagtggtat atgtgattta gggattaggg gcatattgta tttaggcatt aatttcatat | 8700 |
| taatatgtgg tattattata ttattggttt taatagtaca ttatattggt acgtagaata | 8760 |
| gttgcattat tagtgtttgt ggtacttagt ttgacttgat | 8800 |

<210> SEQ ID NO 2
<211> LENGTH: 1522
<212> TYPE: DNA
<213> ORGANISM: Zea mays

<400> SEQUENCE: 2

| | |
|---|---:|
| gcacactcgc agctcgcaca tctcatggtg tcctaagaac ggcaagagcc agctctgcct | 60 |
| agcagcagcg cacagccaca tccatggacg ccagcccgac cccaccgctc ccctccgcg | 120 |
| ccccaactcc cagcattgac ctccccgctg gcaaggacag ggccgacgcg gcggctaaca | 180 |
| aggccgcggc tgtgttcgac ctgcgcccggg agcccaagat cccggagcca ttcctgtggc | 240 |
| cgcacgaaga ggcgcggccg acctcggccg cggagctgga ggtgccggtg gtggacgtgg | 300 |
| gcgtgctgcg caatgcgac ggcgcgggc tccgccgcgc cgcggcgcaa gtggcggcgg | 360 |
| cgtgcgcgac gcacgggttc ttccaggtgt gcgggcacgg cgtggacgcg cgctggggc | 420 |
| gcgccgcgct ggacggcgcc agcgacttct tccggctgcc gctggctgag aagcagcggg | 480 |
| cccggcgcgt ccccggcacc gtgtccgggt acacgagcgc gcacgccgac cggttcgcgt | 540 |
| ccaagctccc ctggaaggag accctgtcct tcggcttcca cgacggcgcc gcggcgcccg | 600 |
| tcgtcgtgga ctacttcacc ggcaccctcg gccaagattt cgagccagtg gggcgggtgt | 660 |
| accagaggta ctgcgaggag atgaaggagc tgtcgctgac gatcatggag ctgctggagc | 720 |
| tgagcctggg cgtggagcgc ggctactacc gggagttctt cgaggacagc cgctccatca | 780 |
| tgcggtgcaa ctactacccg ccgtgccggg tgccggagcg cacgctgggc acgggcccgc | 840 |
| actgcgaccc cacggcgctg accatcctcc tgcaggacga cgtcggcggg ctggaggtcc | 900 |
| tggtggacgc cgagtggcgc cccgtccggc ccgtcccagg cgccatggtc atcaacatcg | 960 |
| gcgacacctt catggcgctg tccaacgggc ggtacaagag ctgcctgcac cgcgcggtgg | 1020 |
| tgaaccggcg gcaggagcgg caatcgctgg ccttcttcct gtgcccgcgc gaggaccggg | 1080 |
| tggtgcgccc gccggccagc gccgcgccgc ggcagtaccc ggacttcacc tgggccgacc | 1140 |
| tcatgcgctt cacgcagcgc cactaccgcg ccgacacccg cacgctggac gccttcaccc | 1200 |
| gctggctctc ccacggcccg gcggcggcgg ctccctgcac ctaacgagcc ggccgtctct | 1260 |
| ttcgccgggg cccgcgcggg gttcgcccac gtggtgatca ggtggcagac atgtggccca | 1320 |
| cgggccccgc gccgccttcc ccattttttgg acgaccctac tgctactact actagtgtac | 1380 |
| atatgcaaaa aaatacatat atatataggt actttctcta atattttat atataagcaa | 1440 |
| ggcggcctgg tgttctttc tttgttttgt cgacaactgt ttgatccat cctatggacg | 1500 |
| atggatagtt caatgtttgt ac | 1522 |

<210> SEQ ID NO 3
<211> LENGTH: 1161
<212> TYPE: DNA
<213> ORGANISM: Zea mays

<400> SEQUENCE: 3

| | |
|---|---:|
| atggacgcca gccgacccc accgctcccc ctccgcgccc caactcccag cattgacctc | 60 |
| cccgctggca aggacagggc cgacgcgcg gctaacaagg ccgcggctgt gttcgacctg | 120 |
| cgccgggagc ccaagatccc ggagccattc ctgtggccgc acgaagaggc gcggccgacc | 180 |

-continued

```
tcggccgcgg agctggaggt gccggtggtg acgtgggcg tgctgcgcaa tggcgacggc    240
gcggggctcc gccgcgccgc ggcgcaagtg gcggcggcgt gcgcgacgca cgggttcttc    300
caggtgtgcg ggcacggcgt ggacgcggcg ctggggcgcg ccgcgctgga cggcgccagc    360
gacttcttcc ggctgccgct ggctgagaag cagcgggccc ggcgcgtccc cggcaccgtg    420
tccgggtaca cgagcgcgca cgccgaccgg ttcgcgtcca agctcccctg gaaggagacc    480
ctgtccttcg gcttccacga cggcgccgcg gcgcccgtcg tcgtggacta cttcaccggc    540
accctcggcc aagatttcga gccagtgggg cgggtgtacc agaggtactg cgaggagatg    600
aaggagctgt cgctgacgat catggagctg ctggagctga gcctgggcgt ggagcgcggc    660
tactaccggg agttcttcga ggacagccgc tccatcatgc ggtgcaacta ctacccgccg    720
tgcccggtgc cggagcgcac gctgggcacg ggcccgcact cgaccccac ggcgctgacc    780
atcctcctgc aggacgacgt cggcgggctg gaggtcctgg tggacggcga gtggcgcccc    840
gtccggcccg tcccaggcgc catggtcatc aacatcggcg acaccttcat ggcgctgtcc    900
aacgggcggt acaagagctg cctgcaccgc gcggtggtga accggcggca ggagcggcaa    960
tcgctggcct tcttcctgtg cccgcgcgag accgggtgg tgcgcccgcc ggccagcgcc    1020
gcgccgcggc agtacccgga cttcacctgg gccgacctca tgcgcttcac gcagcgccac    1080
taccgcgccg acaccgcac gctggacgcc ttcacccgct ggctctccca cggcccggcg    1140
gcggcggctc cctgcaccta a                                              1161
```

<210> SEQ ID NO 4
<211> LENGTH: 386
<212> TYPE: PRT
<213> ORGANISM: Zea mays

<400> SEQUENCE: 4

```
Met Asp Ala Ser Pro Thr Pro Pro Leu Pro Leu Arg Ala Pro Thr Pro
1               5                   10                  15

Ser Ile Asp Leu Pro Ala Gly Lys Asp Arg Ala Asp Ala Ala Ala Asn
            20                  25                  30

Lys Ala Ala Ala Val Phe Asp Leu Arg Arg Glu Pro Lys Ile Pro Glu
        35                  40                  45

Pro Phe Leu Trp Pro His Glu Glu Ala Arg Pro Thr Ser Ala Ala Glu
    50                  55                  60

Leu Glu Val Pro Val Val Asp Val Gly Val Leu Arg Asn Gly Asp Gly
65                  70                  75                  80

Ala Gly Leu Arg Arg Ala Ala Ala Gln Val Ala Ala Ala Cys Ala Thr
                85                  90                  95

His Gly Phe Phe Gln Val Cys Gly His Gly Val Asp Ala Ala Leu Gly
            100                 105                 110

Arg Ala Ala Leu Asp Gly Ala Ser Asp Phe Phe Arg Leu Pro Leu Ala
        115                 120                 125

Glu Lys Gln Arg Ala Arg Arg Val Pro Gly Thr Val Ser Gly Tyr Thr
    130                 135                 140

Ser Ala His Ala Asp Arg Phe Ala Ser Lys Leu Pro Trp Lys Glu Thr
145                 150                 155                 160

Leu Ser Phe Gly Phe His Asp Gly Ala Ala Ala Pro Val Val Val Asp
                165                 170                 175

Tyr Phe Thr Gly Thr Leu Gly Gln Asp Phe Glu Pro Val Gly Arg Val
            180                 185                 190
```

```
Tyr Gln Arg Tyr Cys Glu Glu Met Lys Glu Leu Ser Leu Thr Ile Met
            195                 200                 205

Glu Leu Leu Glu Leu Ser Leu Gly Val Glu Arg Gly Tyr Tyr Arg Glu
        210                 215                 220

Phe Phe Glu Asp Ser Arg Ser Ile Met Arg Cys Asn Tyr Tyr Pro Pro
225                 230                 235                 240

Cys Pro Val Pro Glu Arg Thr Leu Gly Thr Gly Pro His Cys Asp Pro
                245                 250                 255

Thr Ala Leu Thr Ile Leu Leu Gln Asp Asp Val Gly Gly Leu Glu Val
                260                 265                 270

Leu Val Asp Gly Glu Trp Arg Pro Val Arg Pro Val Pro Gly Ala Met
        275                 280                 285

Val Ile Asn Ile Gly Asp Thr Phe Met Ala Leu Ser Asn Gly Arg Tyr
        290                 295                 300

Lys Ser Cys Leu His Arg Ala Val Val Asn Arg Arg Gln Glu Arg Gln
305                 310                 315                 320

Ser Leu Ala Phe Phe Leu Cys Pro Arg Glu Asp Arg Val Val Arg Pro
                325                 330                 335

Pro Ala Ser Ala Ala Pro Arg Gln Tyr Pro Asp Phe Thr Trp Ala Asp
                340                 345                 350

Leu Met Arg Phe Thr Gln Arg His Tyr Arg Ala Asp Thr Arg Thr Leu
        355                 360                 365

Asp Ala Phe Thr Arg Trp Leu Ser His Gly Pro Ala Ala Ala Ala Pro
        370                 375                 380

Cys Thr
385

<210> SEQ ID NO 5
<211> LENGTH: 8859
<212> TYPE: DNA
<213> ORGANISM: Zea mays

<400> SEQUENCE: 5
cctattttgt gtctaatact cttcttatat taattgtttg gtcaaacttt agataaattt      60
gactaatgat gcaattaaaa ctgcatcacc tttactaagg tactgcttta tatgtttcga     120
caaaattttc aattattctc tatgtgtttt aatctttgcg ctacacctcc attgatttaa     180
atactcattt atttttaaacc ataacttaaa ttatatcgga tctttgcatc ctttctatgg     240
caccatacat gaatcgatat tttggctgca aattttaat catgttagtt ttagcatttt       300
ttcatatcca tgtgttaagt ttgaatcatg tgttgttttt ataatttta ttgaaaatat      360 agatcctaaa cttcactaat acttacaaca atagcatcat catgtgtttt aatccacgcc     420
acaacactca aggcattgaa ttttcttcta ccaaagagtt gtatgtgtgt attgttcttt     480
aaaaaataga gtgattataa ttaaactacc agtattcata tgtaaaatgt atagacatct     540
aaaataaaat ttgcaaaaaa cattgttgca gactttcaat ataattaaga atgggtttta     600
gggtcatgat atatggtttg ttaaagaaac ttgttttttt ttgcaattga taaactataa     660
aatacatttt cactattgtg tgcatatgta cttggtatac atagtggcat atatcattt      720 tgtttacttt gaggtttgaa ttatctatgt taaaattgga taacatagat acattggtgt     780
gcgtcctttg gcccatttac ttgactgagg agcaatacta taagtaaaa catatttgga     840 tattttatct taaactccta gcataatatt gatttaatta tgaacaaata tatgtttagg     900
tgatagtttc atgggtggta aactatataa gaaggcttac catgatcttt gcaaactcta     960
```

```
ggctatgaaa gagttccatg atttgtctta gaagcataga caaaacagtg ataatgatct    1020
aaatcacact tatggcactg atgaccatat atgcaaagct aaatgcatgt taagttgtat    1080
tatatcatat gtttacaatg actatcgcat ataacgagga atacattgtc tatatagata    1140
gctattactg tagtagtgcc aaatgttgga caacatgaat cataatcttc aaacctagag    1200
aaattgtagt cagtcgtaca catatcgtct agtaagttgt ctatactttt tatttattgt    1260
atcaaatttt attgttatct tgcttgcttg tttgtttgta ccatagacac aatatggtca    1320
aaaagtggtc aatcgattcg aagaagattg caattgacga gtgctaacag ttgatccttt    1380
tgttgtgcac gctagcggag tagcatgaaa agagtaaaat atgaaattag cgttctaaac    1440
tgtttgtgct ataggtactt cgtatttaat ggagtgacta actataggaa ggtgagagct    1500
cagaagtcag caccctcaca cagagttcta gagttagtgg tcatcgaacc acgacaaact    1560
acatgatgag cagaagaggc aacatcaaga ctatgatcaa tagtttcggg tcaatgaatg    1620
acatcgtgat gagtatttat ctaactatat agaacaacaa cacatgatgt tttaagtaag    1680
ttcaactgat cttctattgc tatctttaag tatttaacgt agcgaataat gttttatcta    1740
tttcattcat aaataatgtt gtgacaaaag gggataacca tcacttttac catgttctag    1800
ataccacaac catctccacc atcataatgg gttcttcatt ggtgcttgga cctcaaataa    1860
tcatatctat agccaactta gctcaattct aataaaatta ggcaacttgg cttcattgta    1920
gcaaaaatag ccaacttagc tcaattttat ctaaacttag ctaatctagc acaacttaga    1980
tcaatattag gaaaaactaa tcaatctaat ctagctcaac tatagcgaaa gatagatatt    2040
gtagcataac ttagtagatc tatctcaaat tttagcaaaa actaatcaat ttagataaac    2100
tctataaaat tttaatcatt atgacttatt ccaactaat tgtaacttgc atgattttta    2160
tgttccttct ttataattag caacacctaa agacacgaat gatgagtggt ctaacgcatt    2220
cattaaccag ttgttaaata atactctagg tagatgataa gaactctaat tattctatga    2280
atctaagcta aaagatgttt aatatttaag tattggtgtt tattatgtta tttgaaacga    2340
ttcatgttac ttaaagattt gttatgattt ttaaatatga ttatgataat ttatgtggtg    2400
tggattaact tgtgaacata tgtgatgtag atgaatatgt atgttgtgga tggaaccata    2460
tgaatatata tacacactca tatactattc gttggtgtag gtaaagcttc atccatcggt    2520
aattactaaa tggtcttcag tcattaccac taggtgaagc ttcacacgac cgataattat    2580
tgaagaacgc tcattaattt ccggtaatgg cttattggcc ttcactagtc ggtgaaaatt    2640 agctatttt ataccaataa aaattagcta atatatgtaa accaggtcta attttatgg     2700 gcctcttacc gaccaaaatt gattagatta ttgttacaat agttttagtc aaaagctagc    2760
tatgctataa aaattttgaa ttaaagtgag tttcgtaata aaaattgcat acttttaaaa    2820
taaaataatt aaaaaacagt ttttagaaat acaatcaaac accttatgct ataaaaaaat    2880
tgtaatgtac ctacaaatat ataatacttt actttaaaat aggcctgtgc cttctcggct    2940
ctatatgggc tgcctccaac gaagcgccat ggccatgggc tccactgtgt cgggtcccac    3000
atgaggccgc gcctccctcc aaatgttccc tccctgcctt cgtctttgtc gttgctcgca    3060
aactccctgt cctcccctgt tacaaatacc cccaccgcc cggacagctt ccctgcatac     3120
ttgcagctcg cacatctcat ggtgtcgcag gaacgacaag agccagctgt gcctagcagc    3180
agcagcagca gcgccaagcg cgcagccacg tccatggacg ccagcccggc ccgccgctc     3240 ctcctccgcg cccccactcc cagccccagc attgacctcc ccgctggcaa ggacaaggcc    3300
gacgcggcgg ccagcaaggc cggcgcggcc gtgttcgacc tgcgccggga gcccaagatc    3360
```

-continued

```
cccgcgccat tcctgtggcc gcaggaagag gcgcggccgt cctcggccgc ggagctggag    3420
gtgccgatgg tggacgtggg cgtgctgcgc aatggcgacc gcgcggggct gcggcgcgcc    3480
gcggcgcagg tggccgcggc gtgcgcgacg cacgggttct tccaggtgtg cgggcacggc    3540
gtggacgcgg cgctggggcg cgccgcgctg gacggcgcca cgacttcttt ccggctgccg    3600
ctcgccgaga agcagcgcgc ccggcgcgtc cccggcaccg tgtccgggta cacgagcgcg    3660
cacgccgacc ggttcgcggc caagctcccc tggaaggaga ccctgtcgtt cggctaccac    3720
gacggcgccg cgtcgcctgt cgtcgtggac tacttcgtcg gcaccctcgg ccaggatttc    3780
gagccaatgg ggtaagtaag gtagtaagaa ggagcgccgg tttacattta ccgcacgtcg    3840
gcgtgcggtc gagtcgggac tcgggagacg tatgaacccc cgtcccgtcc catgcatgtg    3900
tggcaggtgg gtgtaccaga ggtactgcga ggagatgaag gagctgtcgc tgacgatcat    3960
ggagctgctg gagctgagcc tgggcgtgga gctgcgcggc tactaccggg agttcttcga    4020
ggacagccgg tccatcatgc ggtgcaacta ctacccgccg tgcccggagc cggagcgcac    4080
gctgggcacg ggcccgcact gcgaccccac ggcgctcacc atcctcctgc aggacgacgt    4140
gggcgggctg gaggtgctgg tggacggtga gtggcgcccc gtccggcccg tcccgggcgc    4200
catggtcatc aacatcggcg acaccttcat ggtaacgaaa cgaaagcgct cgctcctctg    4260
ttttccttgg ccgctcttgt cctgtgtgta tattcagttg agctctctct gtgctgttat    4320
ttcccgaatc ctagtggacc taaacgggca ggttattaca gcacgcacac gtaggcatgt    4380
catgtagcta gtacatacat agcgatgccg atgcaaatgc aatagagaca tgcgttcgag    4440
ttggttccta tctcggcggg ctacggcagg tacacgcggc cgcggcgcgc tctctctagt    4500
ctatccgcgg ccgcgcccag gccgatcgag gcttccgggg gagagttgcg acaagagaac    4560
ggaccgaggg ggtcggctag cggtagcaag ttccctgttg gtttgtggcg ttggagcgtt    4620
gcggagaggc ttgcgcggcg gcggggacgt cgacggggac gtggcgggga gacgatacga    4680
tgggtgccgg gcagggcaac gctttcggcg ggtggccgtg tccaggtgcg cgcggccttg    4740
tcggtttccc cctctcggtg tccatggccg agaaatgggt cgacgaccga gaccgacgct    4800
cggtgcggcg cccatcccgt ctgatccgcc gcgccacgcg agcggcccta tgcgatgccg    4860
cacgggcgcg gagggccgtc gcgcggagta taatgtatag tatatagtac aaggttggtt    4920
ggagtcgggt tgggttggat cgggtcaccg gtacgtggtg gctgctgttg cccccgccgt    4980
ttccgcttgc acttttgtcg cggtttcgct ggcgatccgg cacgcggcgc ccacaccacg    5040
ccggggctcc aaacagctcg ggcccttggc cgtgtgggtg gcaggcactt gcacgcgtcc    5100
ggttgtcgcg gcctggcccg ccgccgggcg caccgcaaca atgagacagc ccgacacgat    5160
gattcttgtg cactgtgcta acccgcatgc catgcaggcc ctgtcgaacg ggaggtacaa    5220
gagctgcctg caccgcgcgg tggtgaacca gcggcgggcg cggcggtcgc tggcctttctt    5280 cctgtgcccg cgcgaggacc gggtggtgcg cccgccggcc agtgctgcgc gcggcgcta    5340 cccggacttc acctgggccg acctcatgcg cttcacgcag cgccactacc gcgccgacac    5400
ccgcacgctg gacgccttca cccgctggct ctcccacggc ccggcccagg cggcggcgcc    5460
tccctgcacc tagcgagccg ggccaaggcc gtctctttcg ccccacgtgc gcgcccagct    5520
gggcaggtgg ccagacacgc ggcccgcggg cccgcgccg ccttgccatt ttttgacgct    5580
ggccctactg ctgtgctact agtgtacata tgcaagagta catatatata tatatatata    5640 cgtatttct atatattata tataaaagca aggcggcccg gtgcccttct cttgttttgt    5700
```

```
ccacaactgt tgatcccat tattctatgg accatggata cttcaatgtt tgtactaaga    5760
ccgtgaacgt gggattcttt tccttcctct gtgttttttc tgagaaaaat taaactgatt    5820
tctgtgaaat ttctttgttt taacaagaaa acagaaaaat tacatgagga aaacgctcca    5880
tttatttcaa caagaaaaaa atacatgaaa cagaaggaga aaaaacgtgt tcgttctatc    5940
attttcacac gagaaaaaaa aacatagaaa acagaaaaac tccccgcgtt cagatgagct    6000
caagaaaatg aacgacacg gacgtcaccc gcgtcttgta gcagtgggcg cacgggtgcc     6060
gaatgtttgc tgggccccca agagaatcgc ttctcctcac gctgaatgaa tgaatcaacg    6120
agggaaacgc tgcaccctga gttccagacg tttccgaatt ccaaacgttt ttgtggcgtg    6180
cgtccatggg gcgcccccaa acttcggacg tttccggcgc tccaacaaat cttctcgctt    6240
cacacgtcac cgtcgtcccg gattcatttg cctcgtcgct ccaccattcg ctgctctcct    6300
ctccacgtac tcttaccctg acctttggga aagaactgaa cattcgagat gcacaacagt    6360
tcaaatataa catatgcagc acaagatcgt tcgactgcta ccgacaagc caacaacgtg     6420 cccagtagaa ctgaatgtac ctgtgatttc cagcactaac ttacagcaac gttgtgaaaa    6480
aacaaaaacg aaaacaaacg gcagaaaaaa cagatgtatt gttctacagt tacaccaaat    6540
attttctggt cctttcagca ccaacaagag ccatacgcat atctagaaga caaaattcct    6600
ctaatttcac ccctacgtgg tagcagttcc tcctcaacac agttcacgtg ctagcgtcga    6660
gttctttggg ccgccacatc gacttctcga cgcagagcag gccctcgctg cccttggtgt    6720
aggtcatccg cacctcccac tgcacggact tggccatgct ctccagctca tttatcgtgt    6780
ccgcggtgtc cctcacgatc agcttgccct gtggcctcag tacacggtcg acctcggcga    6840
aaactgcagc cagtttgcat ctgtaaacag gcaacacaga tttttagtat ctaaaacact    6900
gcaggcaaac gccacaggtt ttagtcgcaa gaagcaataa aagcatgcaa acaatgctac    6960
gtgtacgtat caaaggaaca tgtcaaaact cgttgcatga acgatcattg atgtttcctt    7020
gctgaactag tcacatcagt ctgcttcaac ttctgggttt cactagtaga tataccagaa    7080
gggtagaata atgtgaagag caagaaatac agacctcttt ctgagctttg agaacagatg    7140
gtccgcgtgc agaaggtcat acgttcttgg gtaagtgctg aaagactcgc accagtcatg    7200
gtacatgcca aacaaaccgc gctcgtagat gatgggcagc gtgtctggtg aatcgatcgg    7260
cacgatattc atgacccaga cctttggtc cctcagagct gcagcaaaac tgccatgcaa     7320
caatgtaaag cattagtcaa gaagaaggtg tacagtgcat ttctccttgt caacagtctt    7380
cagtaacaaa aaaaagtgt tatgcttgac tgaatctttc aaagaaatat gcttgatgac     7440
ttatggtgga caagttgcct gttatagtgt tatgttttaa ttaactatgt gccagcttgg    7500
gtaactagta gttatgtagt gtgatctgaa ttaccaaaat ataaataaat aaataaacat    7560
gcccaagaaa ctacgaaaac catttactta ccctccatag acagctctca tgtccatgac    7620
atttctcact ttggaccagt caattcccat gccattcaca tacgatttac ttacaacccg    7680
tttccagtgg gcattatctg cctcaaaatc ttcatttgca ggctttccat agacaccaac    7740
cttggaacca tcaatccaga aagggtctt ctcaagcctt tgcggccata actctggcca     7800
ttttgatcct cggactttg agccaccagg cagtttgtgc atgcatgctt ccaacggtac     7860
attcctgcaa atcaaaaggc tgtgtaagca aagcagagaa gcacttttct ccattgaaaa    7920
tatactcttc tcaaagaacc gaaaccatac caagcagcat ctgcatcatc agattccttg    7980
cacaatggcg ggctgttttc agatctttc tcatagcaaa tattgtccat ggtttctga     8040 tatatgacca taccaacttg gtttaactta tccttagtct tgttgaccat cttccagcac    8100
```

```
atggactttg tcaaagtaga catggctgaa aagggtatgt ggccacatgt tatgttagaa    8160
ataaaattca attttgaaca gttggtccat agcatgtatt ttgaacaaat gcaatccttc    8220
tccatccatg aaagaagttg acccttcata cttaggatta ttcagtactt tcactcatgt    8280
ctgctgaatt tgttctcttg gtagttgcta tacaagaaag ggggaagtac agagtagcta    8340
aacttataca agctatagtc tgatatttgt atgaaacata aattttggta tggatgtctt    8400
attaaaatgg gaggttgtat aatattttc tagcctacct caacttgctt gagactaaaa     8460
ggctttgttg ttgttgttga ggctgtatgg tgctttgact ttacaaatca agttatcagc    8520
taccctactt atggatatac acctctcata aaatgatggt aagaagtttc gatatgtcac    8580
attaacataa gaacttcatt cagttagggt acaacgaagt taagtagtta cggaaatacc    8640
attccaaatc tcaacatcct ctgggagctt ttggtaaaca ggagtggcag accagacaaa    8700
gtaaccacca gggcgtaaca agcggttcaa ttccagcaaa agcatgccac ctaaaagtag    8760
cgagccagca ataagattca gttctatagc aaatcaataa atgaaaggag gacatgtcaa    8820
tatgtaacca gcaggacaaa ccttcgatgt gccaaggga                           8859

<210> SEQ ID NO 6
<211> LENGTH: 1733
<212> TYPE: DNA
<213> ORGANISM: Zea mays

<400> SEQUENCE: 6
atgaggccgc gcctccctcc aaatgttccc tccctgcctt cgtctttgtc gttgctcgca      60
aactccctgt cctcccctgt tacaaatacc cccacccgcc cggacagctt ccctgcatac     120
ttgcagctcg cacatctcat ggtgtcgcag gaacgacaag agccagctgt gcctagcagc     180
agcagcagca gcgccaagcg cgcagccacg tccatggacg ccagcccggc cccgccgctc     240
ctcctccgcg ccccccactcc cagccccagc attgacctcc ccgctggcaa ggacaaggcc    300
gacgcggcgg ccagcaaggc cggcgcggcc gtgttcgacc tgcgccggga gcccaagatc     360
cccgcgccat tcctgtggcc gcaggaagag gcgcggccgt cctcggccgc ggagctggag    420
gtgccgatgg tggacgtggg cgtgctgcgc aatggcgacc gcgcggggct gcggcgcgcc    480
gcggcgcagg tggccgcggc gtgcgcgacg cacgggttct tccaggtgtg cgggcacggc    540
gtggacgcgc cgctggggcg cgccgcgctg acggcgccca cgacttcttt ccggctgccg    600
ctcgccgaga agcagcgcgc ccggcgcgtc cccggcaccg tgtccgggta cacgagcgcg    660
cacgccgacc ggttcgcggc caagctcccc tggaaggaga cctgtcgtt cggctaccac     720 gacggcgccg cgtcgcctgt cgtcgtggac tacttcgtcg gcaccctcgg ccaggatttc    780
gagccaatgg ggtgggtgta ccagaggtac tgcgaggaga tgaaggagct gtcgctgacg    840
atcatggagc tgctggagct gagcctgggc gtggagctgc gcggctacta ccgggagttc    900
ttcgaggaca ccggtccat catgcggtgc aactactacc gccgtgccc ggagccggag     960 cgcacgctgg gcacgggccc gcactgcgac cccacggcgc tcaccatcct cctgcaggac   1020
gacgtgggcg gctggaggt gctggtggac ggtgagtggc ccccgtccg gcccgtcccg    1080 ggcgccatgg tcatcaacat cggcgacacc ttcatggcg tgtcgaacgg gaggtacaag     1140
agctgcctgc accgcgcggt ggtgaaccag cggcgggcgc ggcggtcgct ggccttcttc    1200
ctgtgcccgc gcgaggaccg ggtggtgcgc ccgccggcca gtgctgcgcc gcggcgctac    1260
ccggacttca cctgggccga cctcatgcgc ttcacgcagc gccactaccg cgccgacacc    1320
```

```
cgcacgctgg acgccttcac ccgctggctc tcccacggcc cggcccaggc ggcggcgcct    1380
ccctgcacct agcgagccgg gccaaggccg tctctttcgc cccacgtgcg cgcccagctg    1440
ggcaggtggc cagacacgcg gcccgcgggc cccgcgccgc cttgccattt tttgacgctg    1500
gccctactgc tgtgctacta gtgtacatat gcaagagtac atatatatat atatatatac    1560
gtattttcta tatattatat ataaaagcaa ggcggcccgg tgcccttctc ttgttttgtc    1620
cacaactgtt tgatcccatt attctatgga ccatggatac ttcaatgttt gtactaagac    1680
cgtgaacgtg ggattctttt ccttcctctg tgttttttct gagaaaaatt aaa           1733

<210> SEQ ID NO 7
<211> LENGTH: 1392
<212> TYPE: DNA
<213> ORGANISM: Zea mays

<400> SEQUENCE: 7
atgaggccgc gcctccctcc aaatgttccc tccctgcctt cgtctttgtc gttgctcgca      60
aactccctgt cctcccctgt tacaaatacc cccacccgcc cggacagctt ccctgcatac     120
ttgcagctcg cacatctcat ggtgtcgcag gaacgacaag agccagctgt gcctagcagc     180
agcagcagca gcgccaagcg cgcagccacg tccatggacg ccagcccggc cccgccgctc     240
ctcctccgcg cccccactcc cagccccagc attgacctcc ccgctggcaa ggacaaggcc     300
gacgcggcgg ccagcaaggc cggcgcggcc gtgttcgacc tgcgccggga gcccaagatc     360
cccgcgccat tcctgtggcc gcaggaagag gcgcggccgt cctcggccgc ggagctggag     420
gtgccgatgg tggacgtggg cgtgctgcgc aatggcgacc gcgcggggct gcggcgcgcc     480
gcggcgcagg tggccgcggc gtgcgcgacg cacgggttct tccaggtgtg cgggcacggc     540
gtggacgcgg cgctggggcg cgccgcgctg acggcgccca gcgacttctt ccggctgccg     600
ctcgccgaga agcagcgcgc ccggcgcgtc cccggcaccg tgtccgggta cacgagcgcg     660
cacgccgacc ggttcgcggc caagctcccc tggaaggaga ccctgtcgtt cggctaccac     720
gacggcgccg cgtcgcctgt cgtcgtggac tacttcgtcg gcaccctcgg ccaggatttc     780
gagccaatgg ggtgggtgta ccagaggtac tgcgaggaga tgaaggagct gtcgctgacg     840
atcatggagc tgctggagct gagcctgggc gtggagctgc gcggctacta ccgggagttc     900
ttcgaggaca gccggtccat catgcggtgc aactactacc gccgtgccc ggagccggag      960 cgcacgctgg gcacgggccc gcactgcgac cccacggcgc tcaccatcct cctgcaggac    1020
gacgtgggcg gctggaggt gctggtggac ggtgagtggc ccccgtccg gcccgtcccg      1080 ggcgccatgg tcatcaacat cggcgacacc ttcatggcgc tgtcgaacgg aggtacaag     1140 agctgcctgc accgcgcggt ggtgaaccag cggcgggcgc ggcggtcgct ggccttcttc    1200
ctgtgcccgc gcgaggaccg ggtggtgcgc cgccggcca gtgctgcgcc gcggcgctac     1260
ccggacttca cctgggccga cctcatgcgc ttcacgcagc gccactaccg cgccgacacc    1320
cgcacgctgg acgccttcac ccgctggctc tcccacggcc cggcccaggc ggcggcgcct    1380
ccctgcacct ag                                                         1392

<210> SEQ ID NO 8
<211> LENGTH: 463
<212> TYPE: PRT
<213> ORGANISM: Zea mays

<400> SEQUENCE: 8

Met Arg Pro Arg Leu Pro Pro Asn Val Pro Ser Leu Pro Ser Ser Leu
```

-continued

```
1               5                   10                  15
Ser Leu Leu Ala Asn Ser Leu Ser Ser Pro Val Thr Asn Thr Pro Thr
                20                  25                  30
Arg Pro Asp Ser Phe Pro Ala Tyr Leu Gln Leu Ala His Leu Met Val
                35                  40                  45
Ser Gln Glu Arg Gln Glu Pro Ala Val Pro Ser Ser Ser Ser Ser Ser
        50                  55                  60
Ala Lys Arg Ala Ala Thr Ser Met Asp Ala Ser Pro Ala Pro Pro Leu
65                  70                  75                  80
Leu Leu Arg Ala Pro Thr Pro Ser Pro Ser Ile Asp Leu Pro Ala Gly
                85                  90                  95
Lys Asp Lys Ala Asp Ala Ala Ser Lys Ala Gly Ala Ala Val Phe
                    100                 105                 110
Asp Leu Arg Arg Glu Pro Lys Ile Pro Ala Pro Phe Leu Trp Pro Gln
                115                 120                 125
Glu Glu Ala Arg Pro Ser Ser Ala Ala Glu Leu Glu Val Pro Met Val
            130                 135                 140
Asp Val Gly Val Leu Arg Asn Gly Asp Arg Ala Gly Leu Arg Arg Ala
145                 150                 155                 160
Ala Ala Gln Val Ala Ala Ala Cys Ala Thr His Gly Phe Phe Gln Val
                    165                 170                 175
Cys Gly His Gly Val Asp Ala Ala Leu Gly Arg Ala Ala Leu Asp Gly
                180                 185                 190
Ala Ser Asp Phe Phe Arg Leu Pro Leu Ala Glu Lys Gln Arg Ala Arg
            195                 200                 205
Arg Val Pro Gly Thr Val Ser Gly Tyr Thr Ser Ala His Ala Asp Arg
    210                 215                 220
Phe Ala Ala Lys Leu Pro Trp Lys Glu Thr Leu Ser Phe Gly Tyr His
225                 230                 235                 240
Asp Gly Ala Ala Ser Pro Val Val Val Asp Tyr Phe Val Gly Thr Leu
                    245                 250                 255
Gly Gln Asp Phe Glu Pro Met Gly Trp Val Tyr Gln Arg Tyr Cys Glu
                260                 265                 270
Glu Met Lys Glu Leu Ser Leu Thr Ile Met Glu Leu Leu Glu Leu Ser
            275                 280                 285
Leu Gly Val Glu Leu Arg Gly Tyr Tyr Arg Glu Phe Phe Glu Asp Ser
    290                 295                 300
Arg Ser Ile Met Arg Cys Asn Tyr Tyr Pro Cys Pro Glu Pro Glu
305                 310                 315                 320
Arg Thr Leu Gly Thr Gly Pro His Cys Asp Pro Thr Ala Leu Thr Ile
                    325                 330                 335
Leu Leu Gln Asp Asp Val Gly Gly Leu Glu Val Leu Val Asp Gly Glu
                340                 345                 350
Trp Arg Pro Val Arg Pro Val Pro Gly Ala Met Val Ile Asn Ile Gly
            355                 360                 365
Asp Thr Phe Met Ala Leu Ser Asn Gly Arg Tyr Lys Ser Cys Leu His
    370                 375                 380
Arg Ala Val Val Asn Gln Arg Ala Arg Arg Ser Leu Ala Phe Phe
385                 390                 395                 400
Leu Cys Pro Arg Glu Asp Arg Val Val Arg Pro Ala Ser Ala Ala
                    405                 410                 415
Pro Arg Arg Tyr Pro Asp Phe Thr Trp Ala Asp Leu Met Arg Phe Thr
                420                 425                 430
```

```
Gln Arg His Tyr Arg Ala Asp Thr Arg Thr Leu Asp Ala Phe Thr Arg
        435                 440                 445

Trp Leu Ser His Gly Pro Ala Gln Ala Ala Ala Pro Pro Cys Thr
    450                 455                 460

<210> SEQ ID NO 9
<211> LENGTH: 1229
<212> TYPE: PRT
<213> ORGANISM: Lachnospiraceae bacterium ND2006

<400> SEQUENCE: 9

Ala Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
```

```
                340                 345                 350
Gly Glu Trp Asn Val Ile Arg Asp Lys Trp Asn Ala Glu Tyr Asp Asp
            355                 360                 365
Ile His Leu Lys Lys Lys Ala Val Val Thr Glu Lys Tyr Glu Asp Asp
            370                 375                 380
Arg Arg Lys Ser Phe Lys Lys Ile Gly Ser Phe Ser Leu Glu Gln Leu
385                 390                 395                 400
Gln Glu Tyr Ala Asp Ala Asp Leu Ser Val Val Glu Lys Leu Lys Glu
                405                 410                 415
Ile Ile Ile Gln Lys Val Asp Glu Ile Tyr Lys Val Tyr Gly Ser Ser
                420                 425                 430
Glu Lys Leu Phe Asp Ala Asp Phe Val Leu Glu Lys Ser Leu Lys Lys
            435                 440                 445
Asn Asp Ala Val Val Ala Ile Met Lys Asp Leu Leu Asp Ser Val Lys
            450                 455                 460
Ser Phe Glu Asn Tyr Ile Lys Ala Phe Phe Gly Glu Gly Lys Glu Thr
465                 470                 475                 480
Asn Arg Asp Glu Ser Phe Tyr Gly Asp Phe Val Leu Ala Tyr Asp Ile
                485                 490                 495
Leu Leu Lys Val Asp His Ile Tyr Asp Ala Ile Arg Asn Tyr Val Thr
                500                 505                 510
Gln Lys Pro Tyr Ser Lys Asp Lys Phe Lys Leu Tyr Phe Gln Asn Pro
            515                 520                 525
Gln Phe Met Arg Gly Trp Asp Lys Asp Lys Glu Thr Asp Tyr Arg Ala
            530                 535                 540
Thr Ile Leu Arg Tyr Gly Ser Lys Tyr Tyr Leu Ala Ile Met Asp Lys
545                 550                 555                 560
Lys Tyr Ala Lys Cys Leu Gln Lys Ile Asp Lys Asp Asp Val Asn Gly
                565                 570                 575
Asn Tyr Glu Lys Ile Asn Tyr Lys Leu Leu Pro Gly Pro Asn Lys Met
            580                 585                 590
Leu Pro Arg Val Phe Phe Ser Lys Lys Trp Met Ala Tyr Tyr Asn Pro
            595                 600                 605
Ser Glu Asp Ile Gln Lys Ile Tyr Lys Asn Gly Thr Phe Lys Lys Gly
            610                 615                 620
Asp Met Phe Asn Leu Asn Asp Cys His Lys Leu Ile Asp Phe Phe Lys
625                 630                 635                 640
Asp Ser Ile Ser Arg Tyr Pro Lys Trp Ser Asn Ala Tyr Asp Phe Asn
                645                 650                 655
Phe Ser Glu Thr Glu Lys Tyr Lys Asp Ile Ala Gly Phe Tyr Arg Glu
            660                 665                 670
Val Glu Glu Gln Gly Tyr Lys Val Ser Phe Glu Ser Ala Ser Lys Lys
            675                 680                 685
Glu Val Asp Lys Leu Val Glu Glu Gly Lys Leu Tyr Met Phe Gln Ile
            690                 695                 700
Tyr Asn Lys Asp Phe Ser Asp Lys Ser His Gly Thr Pro Asn Leu His
705                 710                 715                 720
Thr Met Tyr Phe Lys Leu Leu Phe Asp Glu Asn Asn His Gly Gln Ile
                725                 730                 735
Arg Leu Ser Gly Gly Ala Glu Leu Phe Met Arg Arg Ala Ser Leu Lys
            740                 745                 750
Lys Glu Glu Leu Val Val His Pro Ala Asn Ser Pro Ile Ala Asn Lys
            755                 760                 765
```

-continued

Asn Pro Asp Asn Pro Lys Lys Thr Thr Thr Leu Ser Tyr Asp Val Tyr
770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Asp Gly Lys Gly
        835                 840                 845

Asn Ile Val Glu Gln Tyr Ser Leu Asn Glu Ile Ile Asn Asn Phe Asn
850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
            915                 920                 925

Ser Gly Phe Lys Asn Ser Arg Val Lys Val Glu Lys Gln Val Tyr Gln
930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu Thr Ser Lys Ile Asp Pro Ser Thr
            995                 1000                1005

Gly Phe Val Asn Leu Leu Lys Thr Lys Tyr Thr Ser Ile Ala Asp
        1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

```
Ile Leu Pro Lys Asn Ala Asp Ala Asn Gly Ala Tyr Asn Ile Ala
    1175            1180                1185

Arg Lys Val Leu Trp Ala Ile Gly Gln Phe Lys Lys Ala Glu Asp
    1190            1195                1200

Glu Lys Leu Asp Lys Val Lys Ile Ala Ile Ser Asn Lys Glu Trp
    1205            1210                1215

Leu Glu Tyr Ala Gln Thr Ser Val Lys His Ala
    1220            1225
```

```
<210> SEQ ID NO 10
<211> LENGTH: 33
<212> TYPE: DNA
<213> ORGANISM: Solanum tuberosum

<400> SEQUENCE: 10
atgggtagca aaagaggcg tatcaagcag gac                               33

<210> SEQ ID NO 11
<211> LENGTH: 30
<212> TYPE: DNA
<213> ORGANISM: Solanum tuberosum

<400> SEQUENCE: 11
ggatctaaga agcgtaggat caagcaagat                                  30

<210> SEQ ID NO 12
<211> LENGTH: 200
<212> TYPE: DNA
<213> ORGANISM: Zea mays

<400> SEQUENCE: 12
cggcgtatgt gccaaaaact tcgtcacaga gagggccata agaaacatgg cccacggccc    60
aatacgaagc accgcgacga agcccaaaca gcagtccgta ggtggagcaa agcgctgggt   120
aatacgcaaa cgttttgtcc caccttgact aatcacaaga gtggagcgta ccttataaac   180
cgagccgcaa gcaccgaatt                                              200

<210> SEQ ID NO 13
<211> LENGTH: 665
<212> TYPE: DNA
<213> ORGANISM: Zea mays

<400> SEQUENCE: 13
gtcgttgctc gcaaactccc tgtcctcccc tgttacaaat accccaccc gcccggacag     60 cttccctgca tacttgcagc tcgcacatct catggtgtcg caggaacgac aagagccagc   120
tgtgcctagc agcagcagca gcagcgccaa gcgcgcagcc acgtccatgg acgccagccc   180
ggccccgccg ctcctcctcc gcgccccac tcccagcccc agcattgacc tccccgctgg   240
caaggacaag gccgacgcgg cggccagcaa ggccggcgcg gccgtgttcg acctgcgccg   300
ggagcccaag atccccgcgc cattcctgtg gccgcaggaa gaggcgcggc cgtcctcggc   360
cgcggagctg gaggtgccga tggtggacgt gggcgtgctg cgcaatggcg accgcgcggg   420
gctgcggcgc gccgcggcgc aggtggccgc ggcgtgcgcg acgcacgggt tcttccaggt   480
gtgcgggcac ggcgtggacg cggcgctggg gcgcgccgcg ctggacggcg ccagcgactt   540
cttccggctg ccgctcgccg agaagcagcg cgcccggcgc gtccccggca ccgtgtccgg   600
gtacacgagc gcgcacgccg accggttcgc ggccaagctc cctggaagg agaccctgtc   660 gttcg                                                              665
```

```
<210> SEQ ID NO 14
<211> LENGTH: 582
<212> TYPE: DNA
<213> ORGANISM: Zea mays

<400> SEQUENCE: 14
cacatctcat ggtgtcgcag gaacgacaag agccagctgt gcctagcagc agcagcagca    60
gcgccaagcg cgcagccacg tccatggacg ccagcccggc ccgccgctc ctcctccgcg    120 cccccactcc cagccccagc attgacctcc ccgctggcaa ggacaaggcc gacgcggcgg   180
ccagcaaggc cggcgcggcc gtgttcgacc tgcgccggga gcccaagatc cccgcgccat   240
tcctgtggcc gcaggaagag gcgcggccgt cctcggccgc ggagctggag gtgccgatgg   300
tggacgtggg cgtgctgcgc aatggcgacc gcgcggggct gcggcgcgcc gcggcgcagg   360
tggccgcggc gtgcgcgacg cacgggttct tccaggtgtg cgggcacggc gtggacgcgg   420
cgctggggcg cgccgcgctg gacgcgcca gcgacttctt ccggctgccg ctcgccgaga    480
agcagcgcgc ccggcgcgtc cccggcaccg tgtccgggta cacgagcgcg cacgccgacc   540
ggttcgcggc caagctcccc tggaaggaga ccctgtcgtt cg                     582

<210> SEQ ID NO 15
<211> LENGTH: 23
<212> TYPE: DNA
<213> ORGANISM: Zea mays

<400> SEQUENCE: 15
ctggaaggag accctgtcct tcg                                          23

<210> SEQ ID NO 16
<211> LENGTH: 23
<212> TYPE: DNA
<213> ORGANISM: Zea mays

<400> SEQUENCE: 16
ccggcaccct cggccaagat ttc                                          23

<210> SEQ ID NO 17
<211> LENGTH: 23
<212> TYPE: DNA
<213> ORGANISM: Zea mays

<400> SEQUENCE: 17
ctccctgcct tcgtctttgt cgt                                          23

<210> SEQ ID NO 18
<211> LENGTH: 23
<212> TYPE: DNA
<213> ORGANISM: Zea mays

<400> SEQUENCE: 18
ctgcatactt gcagctcgca cat                                          23

<210> SEQ ID NO 19
<211> LENGTH: 23
<212> TYPE: DNA
<213> ORGANISM: Zea mays

<400> SEQUENCE: 19
ctggaaggag accctgtcgt tcg                                          23
```

<210> SEQ ID NO 20
<211> LENGTH: 23
<212> TYPE: DNA
<213> ORGANISM: Glycine max

<400> SEQUENCE: 20
gtaagaagct cttcaccgtt cca                                          23

<210> SEQ ID NO 21
<211> LENGTH: 18
<212> TYPE: DNA
<213> ORGANISM: Artificial Sequence
<220> FEATURE:
<223> OTHER INFORMATION: PCR primer MD2611

<400> SEQUENCE: 21
cacgcccacg tccaccat                                                18

<210> SEQ ID NO 22
<211> LENGTH: 27
<212> TYPE: DNA
<213> ORGANISM: Artificial Sequence
<220> FEATURE:
<223> OTHER INFORMATION: PCR primer MD2615

<400> SEQUENCE: 22
agaactgaat gaatgaatat gcacagc                                      27

<210> SEQ ID NO 23
<211> LENGTH: 19
<212> TYPE: DNA
<213> ORGANISM: Artificial Sequence
<220> FEATURE:
<223> OTHER INFORMATION: PCR primer LR1151

<400> SEQUENCE: 23
acgggttctt ccaggtgtg                                               19

<210> SEQ ID NO 24
<211> LENGTH: 21
<212> TYPE: DNA
<213> ORGANISM: Artificial Sequence
<220> FEATURE:
<223> OTHER INFORMATION: PCR primer LR1148

<400> SEQUENCE: 24
ttcatctcct cgcagtacct c                                            21

<210> SEQ ID NO 25
<211> LENGTH: 877
<212> TYPE: DNA
<213> ORGANISM: Zea mays

<400> SEQUENCE: 25
gtcgtgcccc tctctagaga taaagagcat tgcatgtcta aagtataaaa aattaccaca    60 tattttttg tcacacttat ttgaagtgta gtttatctat ctctatacat atatttaaac    120
ttcactctac aaataatata gtctataata ctaaaataat attagtgttt tagaggatca   180
tataaataaa ctgctagaca tggtctaaag gataattgaa tattttgaca atctacagtt   240
ttatcttttt agtgtgcatg tgatctctct gttttttttg caaatagctt gacctatata   300
atacttcatc catttttatta gtacatccat ttaggattta gggttgatgg tttctataga   360
ctaattttta gtacatccat tttattcttt ttagtctcta aattttttaa aactaaaact   420

```
ctatttttagt tttttattta ataatttaga tataaaatga aataaaataa attgactaca        480
aataaaacaa ataccctta agaaataaaa aaactaagca aacatttttc ttgtttcgag         540
tagataatga caggctgttc aacgccgtcg acgagtctaa cggacaccaa ccagcgaacc        600
agcagcgtcg cgtcgggcca agcgaagcag acggcacgga atctctgtag ctgcctctgg        660 accoctctcg agagttccgc tccaccgttg gacttgctcc gctgtcggca tccagaaatt        720
gcgtggcgga gcggcagacg tgaggcggca cggcaggcgg cctcttcctc ctctcacggc        780
accggcagct acggggatt cctttcccac cgctccttcg cttteccttc ctcgcccgcc        840 gtaataaata gacaccccct ccacaccctc tttcccc                                 877

<210> SEQ ID NO 26
<211> LENGTH: 400
<212> TYPE: DNA
<213> ORGANISM: Zea mays

<400> SEQUENCE: 26
tcccagcccc agcattgacc tccccgctgg caaggacaag gccgacgcgg cggccagcaa         60
ggccggcgcg gccgtgttcg acctgcgccg ggagcccaag atccccgcgc cattcctgtg        120
gccgcaggaa gaggcgcggc cgtcctcggc cgcggagctg gaggtgccga tggtggacgt        180
gggcgtgctg cgcaatggcg accgcgcggg gctgcggcgc gccgcggcgc aggtggccgc        240
ggcgtgcgcg acgcacgggt tcttccaggt gtgcgggcac ggcgtggacg cggcgctggg        300
gcgcgccgcg ctggacggcg ccagcgactt cttccggctg ccgctcgccg agaagcagcg        360
cgcccggcgc gtccccggca ccgtgtccgg gtacacgagc                              400

<210> SEQ ID NO 27
<211> LENGTH: 3042
<212> TYPE: DNA
<213> ORGANISM: Artificial Sequence
<220> FEATURE:
<223> OTHER INFORMATION: genome edited sequence

<400> SEQUENCE: 27
atggacgcca gcccgacccc accgctcccc ctccgcgccc caactcccag cattgacctc         60
cccgctggca aggacagggc cgacgcggcg gctaacaagg ccgcggctgt gttcgacctg        120
cgccgggagc ccaagatccc ggagccattc ctgtggccgc acgaagaggc gcggccgacc        180
tcggccgcgg agctggaggt gccggtggtg gacgtgggcg tgctgcgcaa tggcgacggc        240
gcggggctcc gccgcgccgc ggcgcaagtg cggcggcgcg tgcgcgacgc agggttcttc        300
caggtgtgcg ggcacggcgt ggacgcggcg ctggggcgcg ccgcgctgga cggcgccagc        360
gacttcttcc ggctgccgct ggctgagaag cagcgggccc ggcgcgtccc cggcaccgtg        420
tccgggtaca cgagcgcgca cgccgaccgg ttcgcgtcca agctcccctg gaaggagacc        480
caaggtctcc ttccagggga gcttggccgc gaaccggtcg cgtgcgcgc tcgtgtaccc        540 ggacacggtg ccgggacgc gccgggcgcg ctgcttctcg gcgagcggca gccggaagaa        600
gtcgctggcg ccgtccagcg cggcgcgccc cagcgccgcg tccacgccgt gcccgcacac        660
ctggaagaac ccgtgcgtcg cgcacgccgc ggccacctgc gccgcggcgc gccgcagccc        720
cgcgcggtcg ccattgcgca gcacgcccac gtccaccatc ggcacctcca gctccgcggc        780
cgaggacggc cgcgcctctt cctgcggcca caggaatggc gcggggatct tgggctcccg        840
gcgcaggtcg aacacggccg cgccggcctt gctggccgcc gcgtcggcct tgtccttgcc        900
```

```
agcggggagg tcaatgctgg ggctgggagt gggggcgcgg aggaggagcg gcggggccgg     960
gctggcgtcc atggacgtgg ctgcgcgctt ggcgctgctg ctgctgctgc taggcacagc    1020
tggctcttgt cgttcctgcg acaccatgag gcttccacga cggcgccgcg cgcccgtcg     1080
tcgtggacta cttcaccggc accctcggcc acgagccagt ggggtgagta aagaagaaga    1140
tggcgccgaa tttacattta taagtaggac cagcagaagc ccctgcccct ggggccctta    1200
gcattgcatt cgactgatga atacgcatgg caggcgggtg taccagaggt actgcgagga    1260
gatgaaggag ctgtcgctga cgatcatgga gctgctggag ctgagcctgg gcgtggagcg    1320
cggctactac cgggagttct tcgaggacag ccgctccatc atgcggtgca actactaccc    1380
gccgtgcccg gtgccggagc gcacgctggg cacgggcccg cactgcgacc ccacggcgct    1440
gaccatcctc ctgcaggacg acgtcggcgg gctggaggtc ctggtggacg gcgagtggcg    1500
ccccgtccgg cccgtcccag gcgccatggt catcaacatc ggcgacacct tcatggtaac    1560
gaacgaaagc gccggctcct ctgctttct tggcctcttt gtccctgccc tgtgctgctg     1620
tgcatattca ttcattcagt tctctgtggg gttttttttt tgtttaattt ttttttggga    1680
tcgtatccag tgcacaaggg ccacgccgtg cacaaatgca caaaacgaaa tctggccgtc    1740
cattttccat ccaacgacat gacggcgcgg ggggtttttc acaaaacaga ctcggcaagc    1800
tacggaggtt gcgggagggt tcatctgcat atttacgacg gccgttggat ggaaaatgga    1860
cggccagatt tcgttttgtg tatttgtgca cggcgtggcc cttgtgcact ggatacgatc    1920
ccattttttt ttttgccccg aatcctagtg gacctaactg gacagattac agcacgcaca    1980
cgtaggcatg tcatgtagca gcactgcagt cgggtgcagt ccagtccagt cctgtccagc    2040
cgcgacactg tagtacatag cgatgcaacg gagacacgcg ttggagttgg ttccatctct    2100
tctcggcggc cgtgccgagg cttcgcgggg gaagctgcga caacagaacg gaccgccggg    2160
ggtgggcagg cagcaagctc cctgttggct tgtgccgttg cgcagcggcg ggtaccggac    2220
aacgctttcg gcggcgcgcg gcctcgtcgg cttcccctgt ttttgatgcc gcctctcggt    2280
gtccggggac cgggaggatc gatggggccc gtgccgtctg atccgccacg cgagcggtcc    2340
tatgcgatgc gccgcacgag cgcgggggg ccgtggaaca gtacacagct gggtcactca     2400
ctcactcatc ccgctggttg tggctgcttg gttgcaactt ggctcggctg tctgtctgtt    2460
gcccccgccg cgttttctag ccgtttccgc tttgctcgcg gtttcgctgg cgatccggca    2520
cgcggcgccc acaccgggg ctggcccctt ggccgagtgg gtggcaggca cttgcatgca     2580
tccgccggt ttcccgcgac caagctggcc cgccgcaaca atgagagtga gacgagactt     2640
tgtgtcagtg tgtgtatgta catgtatgtc tgcgcgacag ccctaccgtc cgacacgatg    2700
attcttgtgc actgtactgt actgtactaa ctcccccac ccctccggt atgtaacgca      2760
tgccatatgc aggcgctgtc caacgggcgg tacaagagct gcctgcaccg cgcggtggtg    2820
aaccggcggc aggagcggca atcgctggcc ttcttcctgt gcccgcgcga ggaccgggtg    2880
gtgcgcccgc cggccagcgc cgcgccgcgg cagtaccccgg acttcacctg gccgacctc    2940
atgcgcttca cgcagcgcca ctaccgcgcc gacacccgca cgctggacgc cttcacccgc    3000
tggctctccc acggcccggc ggcggcggct ccctgcacct aa                       3042
```

<210> SEQ ID NO 28  
<211> LENGTH: 569  
<212> TYPE: DNA  
<213> ORGANISM: Artificial Sequence  
<220> FEATURE:  
<223> OTHER INFORMATION: genome edited sequence

<400> SEQUENCE: 28

```
aaggtctcct tccaggggag cttggccgcg aaccggtcgg cgtgcgcgct cgtgtacccg    60
gacacggtgc cggggacgcg ccgggcgcgc tgcttctcgg cgagcggcag ccggaagaag   120
tcgctggcgc cgtccagcgc ggcgcgcccc agcgccgcgt ccacgccgtg cccgcacacc   180
tggaagaacc cgtgcgtcgc gcacgccgcg gccacctgcg ccgcggcgcg ccgcagcccc   240
gcgcggtcgc cattgcgcag cacgcccacg tccaccatcg gcacctccag ctccgcggcc   300
gaggacggcc gcgcctcttc ctgcggccac aggaatggcg cggggatctt gggctcccgg   360
cgcaggtcga acacggccgc gccggccttg ctggccgccg cgtcggcctt gtccttgcca   420
gcggggaggt caatgctggg gctgggagtg ggggcgcgga ggaggagcgg cggggccggg   480
ctggcgtcca tggacgtggc tgcgcgcttg gcgctgctgc tgctgctgct aggcacagct   540
ggctcttgtc gttcctgcga caccatgag                                    569
```

<210> SEQ ID NO 29
<211> LENGTH: 2850
<212> TYPE: DNA
<213> ORGANISM: Artificial Sequence
<220> FEATURE:
<223> OTHER INFORMATION: genome edited sequence

<400> SEQUENCE: 29

```
atggacgcca gcccgacccc accgctcccc ctccgcgccc caactcccag cattgacctc    60
cccgctggca aggacagggc cgacgcggcg gctaacaagg ccgcggctgt gttcgacctg   120
cgccgggagc ccaagatccc ggagccattc ctgtggccgc acgaagaggc gcggccgacc   180
tcggccgcgg agctggaggt gccggtggtg gacgtgggcg tgctgcgcaa tggcgacggc   240
gcggggctcc gccgcgccgc ggcgcaagtg gcggcggcgt gcgcgacgca cgggttcttc   300
caggtgtgcg gcacggcgt ggacgcggcg ctggggcgcg ccgcgctgga cggcgccagc   360
gacttcttcc ggctgccgct ggctgagaag cagcgggccc ggcgcgtccc cggcaccgtg   420
tccgggtaca cgagcgcgca cgccgaccgg ttcgcgtcca agctcccctg gaaggagacg   480
acacggtgcc ggggacgcgc cgggcgcgct gcttctcggc gagcggcagc cggaagaagt   540
cgctggcgcc gtccagcgcg gcgcgcccca gcgccgcgtc cacgccgtgc ccgcacacct   600
ggaagaaccc gtgcgtcgcg cacgccgcgg ccacctgcgc cgcggcgcgc cgcagccccg   660
cgcggtcgcc attgcgcagc acgcccacgt ccaccatcgg cacctccagc tccgcggccg   720
aggacggccg cgcctcttcc tgcggccaca ggaatggcgc ggggatcttg ggctcccggc   780
gcaggtcgaa cacggccgcg ccggccttgc tggccgccgc gtcggccttg tccttgccag   840
cggggaggtc aatgctgggg ctgggatttc acgacggcg ccgcggcgcc cgtcgtcgtg   900
gactacttca ccggcacccct cggccagcca gtggggtgag taaagaagaa gatggcgccg   960
aatttacatt tataagtagg accagcagaa gcccctgccc ctggggggcct tagcattgca  1020
ttcgactgat gaatacgcat ggcaggcggg tgtaccagag gtactgcgag gagatgaagg  1080
agctgtcgct gacgatcatg gagctgctgg agctgagcct gggcgtggag cgcggctact  1140
accgggagtt cttcgaggac agccgctcca tcatgcggtg caactactac ccgccgtgcc  1200
cggtgccgga gcgcacgctg gcacgggcc cgcactgcga ccccacggcg ctgaccatcc  1260
tcctgcagga cgacgtcggc gggctggagg tcctggtgga cggcgagtgg cgccccgtcc  1320
ggcccgtccc aggcgccatg gtcatcaaca tcggcgacac cttcatggta acgaacgaaa  1380
```

| | |
|---|---:|
| gcgccggctc ctctgctttt cttggcctct ttgtccctgc cctgtgctgc tgtgcatatt | 1440 |
| cattcattca gttctctgtg gggttttttt tttgtttaat tttttttttgg gatcgtatcc | 1500 |
| agtgcacaag ggccacgccg tgcacaaatg cacaaaacga aatctggccg tccattttcc | 1560 |
| atccaacgac atgacggcgc gggggttttt cacaaaacag actcggcaag ctacggaggt | 1620 |
| tgcgggaggg ttcatctgca tatttacgac ggccgttgga tggaaaatgg acggccagat | 1680 |
| ttcgttttgt gtatttgtgc acggcgtggc ccttgtgcac tggatacgat cccattttt | 1740 |
| tttttgcccc gaatcctagt ggacctaact ggacagatta cagcacgcac acgtaggcat | 1800 |
| gtcatgtagc agcactgcag tcgggtgcag tccagtccag tcctgtccag ccgcgacact | 1860 |
| gtagtacata gcgatgcaac ggagacacgc gttggagttg gttccatctc ttctcggcgg | 1920 |
| ccgtgccgag gcttccgcgg ggaagctgcg acaacagaac ggaccgccgg gggtgggcag | 1980 |
| gcagcaagct ccctgttggc ttgtgccgtt gcgcagcggc gggtaccgga caacgctttc | 2040 |
| ggcggcgcgc ggcctcgtcg gcttcccctg tttttgatgc cgcctctcgg tgtccgggga | 2100 |
| ccgggaggat cgatggggcc cgtgccgtct gatccgccac gcgagcggtc ctatgcgatg | 2160 |
| cgccgcacga gcgcgggggg gccgtggaac agtacacagc tgggtcactc actcactcat | 2220 |
| cccgctggtt gtggctgctt ggttgcaact tggctcggct gtctgtctgt tgccccgccg | 2280 |
| cgttttctag ccgtttccgc tttgctcgcg gtttcgctgg cgatccggca cgcggcgccc | 2340 |
| acacccgggg ctggccccctt ggccgagtgg gtggcaggca cttgcatgca tccggccggt | 2400 |
| ttcccgcgac caagctggcc cgccgcaaca atgagagtga acgagactt tgtgtcagtg | 2460 |
| tgtgtatgta catgtatgtc tgcgcgacag ccctaccgtc cgacacgatg attcttgtgc | 2520 |
| actgtactgt actgtactaa ctcccccccc cctccggtat gtaacgcatg ccatatgcag | 2580 |
| gcgctgtcca acgggcggta caagagctgc ctgcaccgcg cggtggtgaa ccggcggcag | 2640 |
| gagcggcaat cgctggccctt cttcctgtgc ccgcgcgagg accgggtggt gcgcccgccg | 2700 |
| gccagcgccg cgccgcggca gtacccggac ttcacctggg ccgacctcat gcgcttcacg | 2760 |
| cagcgccact accgcgccga cacccgcacg ctggacgcct tcacccgctg gctctcccac | 2820 |
| ggcccggcgg cggcggctcc ctgcacctaa | 2850 |

<210> SEQ ID NO 30
<211> LENGTH: 387
<212> TYPE: DNA
<213> ORGANISM: Artificial Sequence
<220> FEATURE:
<223> OTHER INFORMATION: genome edited sequence

<400> SEQUENCE: 30

| | |
|---|---:|
| tcccagcccc agcattgacc tccccgctgg caaggacaag gccgacgcgg cggccagcaa | 60 |
| ggccggcgcg gccgtgttcg acctgcgccg ggagcccaag atccccgcgc cattcctgtg | 120 |
| gccgcaggaa gaggcgcggc cgtcctcggc cgcggagctg gaggtgccga tggtggacgt | 180 |
| gggcgtgctg cgcaatggcg accgcgcggg gctgcgcgcg ccgcggcgc aggtggccgc | 240 |
| ggcgtgcgcg acgcacgggt tcttccaggt gtgcgggcac ggcgtggacg cggcgctggg | 300 |
| gcgcgccgcg ctggacggcg ccagcgactt cttccggctg ccgctcgccg agaagcagcg | 360 |
| cgcccggcgc gtccccggca ccgtgtc | 387 |

<210> SEQ ID NO 31
<211> LENGTH: 3010
<212> TYPE: DNA
<213> ORGANISM: Artificial Sequence
<220> FEATURE:
<223> OTHER INFORMATION: genome edited sequence

<400> SEQUENCE: 31

| | | | | | |
|---|---|---|---|---|---|
| atggacgcca | gcccgacccc | accgctcccc | ctccgcgccc | caactcccag | cattgacctc | 60 |
| cccgctggca | aggacagggc | cgacgcgcg | gctaacaagg | ccgcggctgt | gttcgacctg | 120 |
| cgccgggagc | ccaagatccc | ggagccattc | ctgtggccgc | acgaagaggc | gcggccgacc | 180 |
| tcggccgcgg | agctggaggt | gccggtggtg | gacgtgggcg | tgctgcgcaa | tggcgacggc | 240 |
| gcggggctcc | gccgcgccgc | ggcgcaagtg | gcggcggcgt | gcgcgacgca | cgggttcttc | 300 |
| caggtgtgcg | gcacggcgt | ggacgcggcg | ctggggcgcg | ccgcgctgga | cggcgccagc | 360 |
| gacttcttcc | ggctgccgct | ggctgagaag | cagcgggccc | ggcgcgtccc | cggcaccgtg | 420 |
| tccgggtaca | cgagcgcgca | cgccgaccgg | ttcgcgtcca | agctcccctg | gaaggagacc | 480 |
| ctggcttcca | cgacggcgcc | gcggcgcccg | tcgtcgtgga | ctacttcacc | ggcacgcgaa | 540 |
| ccggtcggcg | tgcgcgctcg | tgtacccgga | cacggtgccg | ggacgcgcc | gggcgcgctg | 600 |
| cttctcggcg | agcggcagcc | ggaagaagtc | gctggcgccg | tccagcgcgg | cgcgcccag | 660 |
| cgccgcgtcc | acgccgtgcc | cgcacacctg | gaagaacccg | tgcgtcgcgc | acgccgcggc | 720 |
| cacctgcgcc | gcggcgcgcc | gcagccccgc | gcggtcgcca | ttgcgcagca | cgcccacgtc | 780 |
| caccatcggc | acctccagct | ccgcggccga | ggacggccgc | gcctcttcct | gcggccacag | 840 |
| gaatggcgcg | gggatcttgg | gctcccggcg | caggtcgaac | acggccgcgc | cggccttgct | 900 |
| ggccgccgcg | tcggccttgt | ccttgccagc | ggggaggtca | atgctgggc | tgggagtggg | 960 |
| ggcgcggagg | aggagcggcg | gggccgggct | ggcgtccatg | acgtggctg | cgcgcttggc | 1020 |
| gctgctgctg | ctgctgctag | gcacagctgg | ctcttgtcgt | tcctgcgaca | ccatgagttc | 1080 |
| gagccagtgg | ggtgagtaaa | aagaagatg | gcgccgaatt | tacatttata | agtaggacca | 1140 |
| gcagaagccc | ctgccctgg | gggcttagc | attgcattcg | actgatgaat | acgcatggca | 1200 |
| ggcgggtgta | ccagaggtac | tgcgaggaga | tgaaggagct | gtcgctgacg | atcatggagc | 1260 |
| tgctggagct | gagcctgggc | gtggagcgcg | gctactaccg | ggagttcttc | gaggacagcc | 1320 |
| gctccatcat | gcggtgcaac | tactacccgc | cgtgcccggt | gccggagcgc | acgctgggca | 1380 |
| cgggcccgca | ctgcgacccc | acggcgctga | ccatcctcct | gcaggacgac | gtcggcgggc | 1440 |
| tggaggtcct | ggtggacggc | gagtggcgcc | cgtccggcc | cgtcccaggc | gccatggtca | 1500 |
| tcaacatcgg | cgacaccttc | atggtaacga | acgaaagcgc | cggctcctct | gcttttcttg | 1560 |
| gcctctttgt | ccctgccctg | tgctgctgt | catattcatt | cattcagttc | tctgtggggt | 1620 |
| ttttttttg | tttaattttt | ttttgggatc | gtatccagtg | cacaagggcc | acgccgtgca | 1680 |
| caaatgcaca | aaacgaaatc | tggccgtcca | ttttccatcc | aacgacatga | cggcgcgggg | 1740 |
| ggtttttcac | aaaacagact | cggcaagcta | cggaggttgc | gggagggttc | atctgcatat | 1800 |
| ttacgacggc | cgttggatgg | aaaatggacg | gccagatttc | gttttgtgta | tttgtgcacg | 1860 |
| gcgtggccct | tgtgcactgg | atacgatccc | atttttttt | ttgccccgaa | tcctagtgga | 1920 |
| cctaactgga | cagattacag | cacgcacacg | taggcatgtc | atgtagcagc | actgcagtcg | 1980 |
| ggtgcagtcc | agtccagtcc | tgtccagccg | cgacactgta | gtacatagcg | atgcaacgga | 2040 |
| gacacgcgtt | ggagttggtt | ccatctcttc | tcggcggccg | tgccgaggct | tccgcgggga | 2100 |
| agctgcgaca | acagaacgga | ccgccggggg | tgggcaggca | gcaagctccc | tgttggcttg | 2160 |
| tgccgttgcg | cagcggcggg | taccggacaa | cgctttcggc | ggcgcgcggc | ctcgtcggct | 2220 |

```
tccccctgttt ttgatgccgc ctctcggtgt ccggggaccg ggaggatcga tggggcccgt    2280
gccgtctgat ccgccacgcg agcggtccta tgcgatgcgc cgcacgagcg cggggggggcc    2340 gtggaacagt acacagctgg gtcactcact cactcatccc gctggttgtg gctgcttggt    2400
tgcaacttgg ctcggctgtc tgtctgttgc ccccgccgcg ttttctagcc gtttccgctt    2460
tgctcgcggt ttcgctggcg atccggcacg cggcgcccac acccgggct ggccccttgg    2520 ccgagtgggt ggcaggcact tgcatgcatc cggccggttt cccgcgacca agctggcccg    2580
ccgcaacaat gagagtgaga cgagactttg tgtcagtgtg tgtatgtaca tgtatgtctg    2640
cgcgacagcc ctaccgtccg acacgatgat tcttgtgcac tgtactgtac tgtactaact    2700
ccccccaccc cctccggtat gtaacgcatg ccatatgcag gcgctgtcca acgggcggta    2760
caagagctgc ctgcaccgcg cggtggtgaa ccggcggcag gagcggcaat cgctggcctt    2820
cttcctgtgc ccgcgcgagg accgggtggt gcgcccgccg ccagcgccg cgccgcggca    2880 gtacccggac ttcacctggg ccgacctcat gcgcttcacg cagcgccact accgcgcccga    2940 cacccgcacg ctggacgcct tcacccgctg gctctcccac ggcccggcgg cggcggctcc    3000
ctgcacctaa                                                            3010

<210> SEQ ID NO 32
<211> LENGTH: 542
<212> TYPE: DNA
<213> ORGANISM: Artificial Sequence
<220> FEATURE:
<223> OTHER INFORMATION: genome edited sequence

<400> SEQUENCE: 32
ctcatggtgt cgcaggaacg acaagagcca gctgtgccta gcagcagcag cagcagcgcc      60
aagcgcgcag ccacgtccat ggacgccagc ccggcccccgc cgctcctcct ccgcgccccc    120
actcccagcc ccagcattga cctccccgct ggcaaggaca aggccgacgc ggcggccagc    180
aaggccggcg cggccgtgtt cgacctgcgc cgggagccca agatccccgc gccattcctg    240
tggccgcagg aagaggcgcg gccgtcctcg gccgcggagc tggaggtgcc gatggtggac    300
gtgggcgtgc tgcgcaatgg cgaccgcgcg gggctgcggc gcgccgcggc gcaggtggcc    360
gcggcgtgcg cgacgcacgg gttcttccag gtgtgcgggc acggcgtgga cgcggcgctg    420
gggcgcgccg cgctggacgg cgccagcgac ttcttccggc tgccgctcgc cgagaagcag    480
cgcgcccggc gcgtccccgg caccgtgtcc gggtacacga gcgcgcacgc cgaccggttc    540
gc                                                                    542

<210> SEQ ID NO 33
<211> LENGTH: 3037
<212> TYPE: DNA
<213> ORGANISM: Artificial Sequence
<220> FEATURE:
<223> OTHER INFORMATION: genome edited sequence

<400> SEQUENCE: 33
atggacgcca gcccgacccc accgctcccc ctccgcgccc caactcccag cattgacctc      60
cccgctggca aggacagggc cgacgcggcg gctaacaagg ccgcggctgt gttcgacctg    120 cgccggggagc ccaagatccc ggagccattc ctgtggccgc acgaagaggc gcggccgacc    180
tcggccgcgg agctggaggt gccggtggtg gacgtgggcg tgctgcgcaa tggcgacggc    240
gcggggctcc gccgcgccgc ggcgcaaagtg cggcggcgt gcgcgacgca cgggttcttc    300
caggtgtgcg ggcacggcgt ggacgcggcg ctggggcgcg ccgcgctgga cggcgccagc    360
```

```
gacttcttcc ggctgccgct ggctgagaag cagcgggccc ggcgcgtccc cggcaccgtg    420
tccgggtaca cgagcgcgca cgccgaccgg ttcgcgtcca agctcccctg gaaggagacc    480
ctcggcttcc acgacggcgc cgcggcgccc gtcgtcgtgg actacttcac cggcaccctc    540
ggccgagggt ctccttccag gggagcttgg ccgcgaaccg gtcggcgtgc gcgctcgtgt    600
acccggacac ggtgccgggg acgcgccggg cgcgctgctt ctcggcgagc ggcagccgga    660
agaagtcgct ggcgccgtcc agcgcggcgc gccccagcgc cgcgtccacg ccgtgcccgc    720
acacctggaa gaacccgtgc gtcgcgcacg ccgcggccac ctgcgccgcg gcgcgccgca    780
gccccgcgcg gtcgccattg cgcagcacgc ccacgtccac catcggcacc tccagctccg    840
cggccgagga cggccgcgcc tcttcctgcg gccacaggaa tggcgcgggg atcttgggct    900 cccgcgcag gtcgaacacg gccgcgccgg ccttgctggc cgccgcgtcg gccttgtcct    960
tgccagcggg gaggtcaatg ctggggctgg gagtgggggc gcggaggagg agcggcgggg    1020
ccgggctggc gtccatggac gtggctgcgc gcttggcgct gctgctgctg ctgctaggca    1080
cagctggctc ttgtcgttcc tgcgaccgag ccagtggggt gagtaaagaa gaagatggcg    1140
ccgaatttac atttataagt aggaccagca gaagcccctg cccctggggg ccttagcatt    1200
gcattcgact gatgaatacg catggcaggc gggtgtacca gaggtactgc gaggagatga    1260
aggagctgtc gctgacgatc atggagctgc tggagctgag cctgggcgtg gagcgcggct    1320
actaccggga gttcttcgag gacagccgct ccatcatgcg gtgcaactac tacccgccgt    1380
gcccggtgcc ggagcgcacg ctgggcacgg gcccgcactg cgaccccacg cgcctgacca    1440
tcctcctgca ggacgacgtc ggcgggctgg aggtcctggt ggacggcgag tggcgccccg    1500 tccggccccgt cccaggcgcc atggtcatca acatcggcga caccttcatg gtaacgaacg    1560
aaagcgccgg ctcctctgct tttcttggcc tctttgtccc tgccctgtgc tgctgtgcat    1620
attcattcat tcagttctct gtggggttttt tttttttgttt aattttttttt tgggatcgta    1680 tccagtgcac aagggccacg ccgtgcacaa atgcacaaaa cgaaatctgg ccgtccattt    1740
tccatccaac gacatgacgg cgcggggggt ttttcacaaa acagactcgg caagctacgg    1800
aggttgcggg agggttcatc tgcatattta cgacggccgt tggatggaaa atggacggcc    1860
agatttcgtt ttgtgtattt gtgcacggcg tggcccttgt gcactggata cgatcccatt    1920
tttttttttg ccccgaatcc tagtggacct aactggacag attacagcac gcacacgtag    1980
gcatgtcatg tagcagcact gcagtcgggt gcagtccagt ccagtcctgt ccagccgcga    2040
cactgtagta catagcgatg caacggagac acgcgttgga gttggttcca tctcttctcg    2100
gcggccgtgc cgaggcttcc gcggggaagc tgcgacaaca gaacggaccg ccggggtgg    2160 gcaggcagca agctccctgt tggcttgtgc cgttgcgcag cggcgggtac cggacaacgc    2220
tttcggcggc gcgcggcctc gtcggcttcc cctgtttttg atgccgcctc tcggtgtccg    2280
gggaccggga ggatcgatgg ggcccgtgcc gtctgatccg ccacgcgagc ggtcctatgc    2340
gatgcgccgc acgagcgcgg gggggccgtg aacagtaca cagctgggtc actcactcac    2400
tcatcccgct ggttgtggct gcttggttgc aacttggctc ggctgtctgt ctgttgcccc    2460
cgccgcgttt tctagccgtt tccgctttgc tcgcggtttc gctggcgatc cggcacgcgg    2520
cgcccacacc cggggctggc cccttggccg agtgggtggc aggcacttgc atgcatccgg    2580
ccggtttccc gcgaccaagc tggcccgccg caacaatgag agtgagacga ctttgtgt     2640 cagtgtgtgt atgtacatgt atgtctgcgc gacagcccta ccgtccgaca cgatgattct    2700
```

| | |
|---|---|
| tgtgcactgt actgtactgt actaactccc cccaccccct ccggtatgta acgcatgcca | 2760 |
| tatgcaggcg ctgtccaacg ggcggtacaa gagctgcctg caccgcgcgg tggtgaaccg | 2820 |
| gcggcaggag cggcaatcgc tggccttctt cctgtgcccg cgcgaggacc gggtggtgcg | 2880 |
| cccgccggcc agcgccgcgc cgcggcagta cccggacttc acctgggccg acctcatgcg | 2940 |
| cttcacgcag cgccactacc gcgccgacac ccgcacgctg gacgccttca cccgctggct | 3000 |
| ctcccacggc ccggcggcgg cggctccctg cacctaa | 3037 |

```
<210> SEQ ID NO 34
<211> LENGTH: 562
<212> TYPE: DNA
<213> ORGANISM: Artificial Sequence
<220> FEATURE:
<223> OTHER INFORMATION: genome edited sequence

<400> SEQUENCE: 34
```

| | |
|---|---|
| gtcgcaggaa cgacaagagc cagctgtgcc tagcagcagc agcagcagcg ccaagcgcgc | 60 |
| agccacgtcc atggacgcca gcccggcccc ccgctcctc ctccgcgccc ccactcccag | 120 |
| ccccagcatt gacctccccg ctggcaagga caaggccgac gcggcggcca gcaaggccgg | 180 |
| cgcggccgtg ttcgacctgc gccgggagcc caagatcccc gcgccattcc tgtggccgca | 240 |
| ggaagaggcg cggccgtcct cggccgcgga gctggaggtg ccgatggtgg acgtgggcgt | 300 |
| gctgcgcaat ggcgaccgcg cggggctgcg gcgcgccgcg gcgcaggtgg ccgcggcgtg | 360 |
| cgcgacgcac gggttcttcc aggtgtgcgg gcacggcgtg gacgcggcgc tggggcgcgc | 420 |
| cgcgctggac ggcgccagcg acttcttccg gctgccgctc gccgagaagc agcgcgcccg | 480 |
| gcgcgtcccc ggcaccgtgt ccgggtacac gagcgcgcac gccgaccggt tcgcggccaa | 540 |
| gctcccctgg aaggagaccc tc | 562 |

```
<210> SEQ ID NO 35
<211> LENGTH: 3044
<212> TYPE: DNA
<213> ORGANISM: Artificial Sequence
<220> FEATURE:
<223> OTHER INFORMATION: genome edited sequence

<400> SEQUENCE: 35
```

| | |
|---|---|
| atggacgcca gcccgacccc accgctcccc ctccgcgccc caactcccag cattgacctc | 60 |
| cccgctggca aggacagggc cgacgcggcg gctaacaagg ccgcggctgt gttcgacctg | 120 |
| cgccgggagc ccaagatccc ggagccattc ctgtggccgc acgaagaggc gcggccgacc | 180 |
| tcggccgcgg agctggaggt gccggtggtg acgtgggcg tgctgcgcaa tggcgacggc | 240 |
| gcggggctcc gccgcgccgc ggcgcaagtg gcggcggcgt gcgcgacgca cgggttcttc | 300 |
| caggtgtgcg ggcacggcgt ggacgcggcg ctggggcgcg ccgcgctgga cggcgccagc | 360 |
| gacttcttcc ggctgccgct ggctgagaag cagcgggccc ggcgcgtccc cggcaccgtg | 420 |
| tccgggtaca cgagcgcgca cgccgaccgg ttcgcgtcca agctcccctg gaaggagacc | 480 |
| cgtctccttc caggggagct tggccgcgaa ccggtcggcg tgcgcgctcg tgtacccgga | 540 |
| cacggtgccg gggacgcgcc gggcgcgctg cttctcggcg agcggcagcc ggaagaagtc | 600 |
| gctggcgccg tccagcgcgg cgcgcccag cgccgcgtcc acgccgtgcc cgcacacctg | 660 |
| gaagaacccg tgcgtcgcgc acgccgcggc cacctgcgcc gcggcgcgcc gcagcccgc | 720 |
| gcggtcgcca ttgcgcagca cgcccacgtc caccatcggc acctccagct ccgcggccga | 780 |
| ggacggccgc gcctcttcct gcggccacag gaatggcgcg gggatcttgg gctcccggcg | 840 |

-continued

```
caggtcgaac acggccgcgc cggccttgct ggccgccgcg tcggccttgt ccttgccagc    900
ggggaggtca atgctggggc tgggagtggg ggcgcggagg aggagcggcg gggccgggct    960
ggcgtccatg gacgtggctg cgcgcttggc gctgctgctg ctgctgctag gcacagctgg   1020
ctcttgtcgt tcctgcgaca ccttcggctt ccacgacggc gccgcggcgc ccgtcgtcgt   1080
ggactacttc accggcaccc tcggccaaga tttcgagcca gtggggtgag taagaagaa    1140
gatggcgccg aatttacatt tataagtagg accagcagaa gccctgccc ctgggggcct   1200
tagcattgca ttcgactgat gaatacgcat ggcaggcggg tgtaccagag gtactgcgag   1260
gagatgaagg agctgtcgct gacgatcatg gagctgctgg agctgagcct gggcgtggag   1320
cgcggctact accgggagtt cttcgaggac agccgctcca tcatgcggtg caactactac   1380
ccgccgtgcc cggtgccgga gcgcacgctg ggcacgggcc cgcactgcga ccccacggcg   1440
ctgaccatcc tcctgcagga cgacgtcggc gggctggagg tcctggtgga cggcgagtgg   1500
cgccccgtcc ggcccgtccc aggcgccatg gtcatcaaca tcggcgacac cttcatggta   1560
acgaacgaaa gcgccggctc ctctgctttt cttggcctct ttgtccctgc cctgtgctgc   1620
tgtgcatatt cattcattca gttctctgtg gggtttttttt tttgtttaat tttttttgg   1680
gatcgtatcc agtgcacaag ggccacgccg tgcacaaatg cacaaaacga aatctggccg   1740
tccattttcc atccaacgac atgacggcgc ggggggtttt tcacaaaaca gactcggcaa   1800
gctacggagg ttgcgggagg gttcatctgc atatttacga cggccgttgg atggaaaatg   1860
gacggccaga tttcgttttg tgtatttgtg cacggcgtgg cccttgtgca ctggatacga   1920
tcccattttt ttttttgccc cgaatcctag tggacctaac tggacagatt acagcacgca   1980
cacgtaggca tgtcatgtag cagcactgca gtcgggtgca gtccagtcca gtcctgtcca   2040
gccgcgacac tgtagtacat agcgatgcaa cggagacacg cgttggagtt ggttccatct   2100
cttctcggcg gccgtgccga ggcttccgcg gggaagctgc gacaacagaa cggaccgccg   2160
ggggtgggca ggcagcaagc tccctgttgg cttgtgccgt tgcgcagcgg cgggtaccgg   2220
acaacgcttt cggcggcgcg cggcctcgtc ggcttcccct gtttttgatg ccgcctctcg   2280
gtgtccgggg accgggagga tcgatggggc ccgtgccgtc tgatccgcca cgcgagcggt   2340
cctatgcgat gcgccgcacg agcgcggggg ggccgtggaa cagtacacag ctgggtcact   2400
cactcactca tcccgctggt tgtggctgct tggttgcaac ttggctcggc tgtctgtctg   2460
ttgccccgc cgcgttttct agccgtttcc gctttgctcg cggtttcgct ggcgatccgg   2520
cacgcggcgc ccacacccgg ggctggcccc ttggccgagt gggtggcagg cacttgcatg   2580
catccggccg gtttcccgcg accaagctgg cccgccgcaa caatgagagt gagacgagac   2640
tttgtgtcag tgtgtgtatg tacatgtatg tctgcgcgac agccctaccg tccgacacga   2700
tgattcttgt gcactgtact gtactgtact aactccccc accccctccg gtatgtaacg   2760
catgccatat gcaggcgctg tccaacgggc ggtacaagag ctgcctgcac cgcgcggtgg   2820
tgaaccggcg gcaggagcgg caatcgctgg ccttcttcct gtgcccgcgc gaggaccggg   2880
tggtgcgccc gccggccagc gccgcgccgc ggcagtaccc ggacttcacc tgggccgacc   2940
tcatgcgctt cacgcagcgc cactaccgcg ccgacacccg cacgctggac gccttcaccc   3000
gctggctctc ccacggcccg gcggcggcgg ctccctgcac ctaa                   3044
```

<210> SEQ ID NO 36
<211> LENGTH: 559
<212> TYPE: DNA

```
<213> ORGANISM: Artificial Sequence
<220> FEATURE:
<223> OTHER INFORMATION: genome edited sequence

<400> SEQUENCE: 36
gtctccttcc aggggagctt ggccgcgaac cggtcggcgt gcgcgctcgt gtacccggac        60
acggtgccgg ggacgcgccg ggcgcgctgc ttctcggcga gcggcagccg gaagaagtcg       120
ctggcgccgt ccagcgcggc gcgcccagc gccgcgtcca cgccgtgccc gcacacctgg        180 aagaaccgt gcgtcgcgca cgccgcggcc acctgcgccg cggcgcgccg cagccccgcg        240
cggtcgccat tgcgcagcac gcccacgtcc accatcggca cctccagctc cgcggccgag       300
gacggccgcg cctcttcctg cggccacagg aatggcgcgg ggatcttggg ctcccggcgc       360
aggtcgaaca cggccgcgcc ggccttgctg gccgccgcgt cggccttgtc cttgccagcg       420
gggaggtcaa tgctggggct gggagtgggg gcgcggagga ggagcggcgg ggccgggctg       480
gcgtccatgg acgtggctgc gcgcttggcg ctgctgctgc tgctgctagg cacagctggc       540
tcttgtcgtt cctgcgaca                                                   559
```

METHODS AND COMPOSITIONS FOR GENERATING DOMINANT SHORT STATURE ALLELES USING GENOME EDITING

CROSS-REFERENCE TO RELATED APPLICATIONS AND INCORPORATION OF SEQUENCE LISTING

This application is a U.S. National Stage of International Application No. PCT/US2020/034993, filed May 28, 2020, which claims the benefit of U.S. Provisional Application No. 62/854,142, filed May 29, 2019, and U.S. Provisional Application No. 62/886,726, filed Aug. 14, 2019, all of which are incorporated by reference in their entireties herein. A sequence listing contained in the file named "P34745US01_SL.TXT" which is 80,022 bytes (measured in MS-Windows®) and created on Nov. 22, 2021, is filed electronically herewith and incorporated by reference in its entirety.

FIELD

The present disclosure relates to methods and compositions for generating dominant alleles of GA oxidase genes via targeted editing of genomes.

BACKGROUND

Gibberellins (gibberellic acids or GAs) are plant hormones that regulate a number of major plant growth and developmental processes. Manipulation of GA levels in semi-dwarf wheat, rice and sorghum plant varieties led to increased yield and reduced lodging in these cereal crops during the 20$^{th}$ century, which was largely responsible for the Green Revolution. However, successful yield gains in other cereal crops, such as corn, through manipulation of the GA pathway, have been challenging. There continues to be a need in the art for the development of monocot or cereal crop plants, such as corn, having increased yield and/or resistance to lodging.

SUMMARY

In an aspect, this disclosure provides a modified corn plant, or plant part thereof, comprising a mutant allele of the endogenous GA20 oxidase_3 locus, wherein the mutant allele comprises a DNA segment inserted into the endogenous GA20 oxidase_3 locus, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_3 locus produces a RNA transcript comprising the antisense RNA sequence.

In an aspect, this disclosure provides a method for producing a mutant allele of the endogenous GA20 oxidase_3 locus, the method comprising: (a) generating a first double-stranded break in the endogenous GA20 oxidase_3 locus in a corn cell using a targeted editing technique; (b) inserting at the first double-stranded break a DNA segment, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_3 locus produces a RNA transcript comprising the antisense RNA sequence.

In an aspect, this disclosure provides a method for producing a mutant allele of the endogenous GA20 oxidase_3 locus, the method comprising: (a) generating a first double-stranded break and a second double strand break in the endogenous GA20 oxidase_3 locus in a corn cell using a targeted editing technique; (b) inserting a DNA segment between the first double-stranded break and the second double-stranded break, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_3 locus produces a RNA transcript comprising the antisense RNA sequence.

In an aspect, this disclosure provides a modified corn plant, or plant part thereof, comprising a mutant allele of the endogenous GA20 oxidase_5 locus, wherein the mutant allele comprises a DNA segment inserted into the endogenous GA20 oxidase_5 locus, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_5 locus produces a RNA transcript comprising the antisense RNA sequence.

In an aspect, this disclosure provides a method for producing a mutant allele of the endogenous GA20 oxidase_5 locus, the method comprising: (a) generating a double-stranded break (DSB) in the endogenous GA20 oxidase_5 locus in a corn cell using a targeted editing technique; (b) inserting at the DSB a DNA segment using a targeted editing technique, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_5 locus produces a RNA transcript comprising the antisense RNA sequence.

In an aspect, this disclosure provides a method for producing a mutant allele of the endogenous GA20 oxidase_5 locus, the method comprising: (a) generating a first double-stranded break and a second double strand break in the endogenous GA20 oxidase_5 locus in a corn cell using a targeted editing technique; (b) inserting a DNA segment between the first double-stranded break and the second double-stranded break, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_5 locus produces a RNA transcript comprising the antisense RNA sequence.

In an aspect, this disclosure provides a method for generating a corn plant comprising: (a) fertilizing at least one female corn plant with pollen from a male corn plant, wherein said the at least one female corn plant and/or the male corn plant comprise(s) a mutant allele of an endogenous GA20 oxidase locus, wherein the mutant allele comprises a DNA segment inserted into the endogenous GA20 oxidase locus, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 or 5-7, and wherein the mutant allele of the endogenous GA20 oxidase locus produces a RNA transcript comprising the antisense RNA sequence; and (b) obtaining at least one seed produced by said fertilizing of step (a).

In an aspect, this disclosure provides a modified corn plant part, corn cell, or corn tissue comprising a mutant allele of the endogenous GA20 oxidase_3 locus, wherein the mutant allele comprises a DNA segment inserted into the endogenous GA20 oxidase_3 locus, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_3 locus produces a RNA transcript comprising the antisense RNA sequence.

In an aspect, this disclosure provides a modified corn plant part, corn cell, or corn tissue comprising a mutant allele of the endogenous GA20 oxidase_5 locus, wherein the mutant allele comprises a DNA segment inserted into the endogenous GA20 oxidase_5 locus, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_5 locus produces a RNA transcript comprising the antisense RNA sequence.

DETAILED DESCRIPTION

Figure 1:
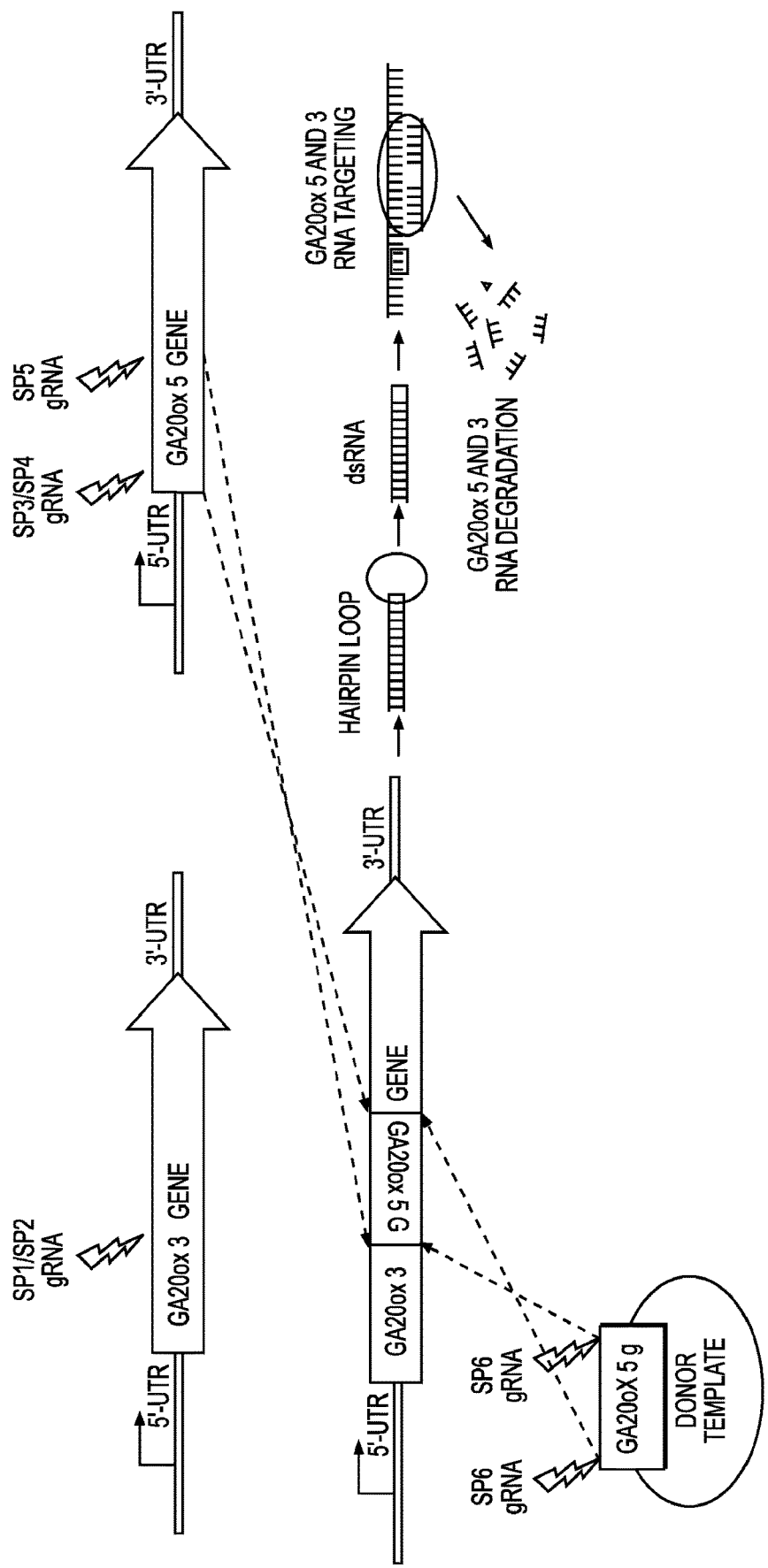
FIG. 1 provides illustrative examples for the production of a genomic modification of the Zm.GA20ox3 locus to encode a RNA transcript with an inverted sequence that can hybridize to a corresponding sequence of the RNA transcript to produce a stem-loop structure, to cause the suppression of one or both copies or alleles at the endogenous Zm.GA20ox3 and Zm.GA20ox5 loci.

Unless defined otherwise herein, terms are to be understood according to their conventional usage by those of ordinary skill in the relevant art. To facilitate understanding of the disclosure, several terms and abbreviations as used herein are defined below as follows:

The term "and/or" when used in a list of two or more items, means that any one of the listed items can be employed by itself or in combination with any one or more of the listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

The term "about" as used herein, is intended to qualify the numerical values that it modifies, denoting such a value as variable within a margin of error. When no particular margin of error, such as a standard deviation to a mean value, is recited, the term "about" should be understood to mean that range which would encompass the recited value and the range which would be included by rounding up or down to that figure, taking into account significant figures.

As used herein, a "plant" includes an explant, plant part, seedling, plantlet or whole plant at any stage of regeneration or development. The term "cereal plant" as used herein refers a monocotyledonous (monocot) crop plant that is in the Poaceae or Gramineae family of grasses and is typically harvested for its seed, including, for example, wheat, corn, rice, millet, barley, sorghum, oat and rye. As commonly understood, a "corn plant" or "maize plant" refers to any plant of species *Zea mays* and includes all plant varieties that can be bred with corn, including wild maize species.

As used herein, a "plant part" can refer to any organ or intact tissue of a plant, such as a meristem, shoot organ/ structure (e.g., leaf, stem or node), root, flower or floral organ/structure (e.g., bract, sepal, petal, stamen, carpel, anther and ovule), seed, embryo, endosperm, seed coat, fruit, the mature ovary, propagule, or other plant tissues (e.g., vascular tissue, dermal tissue, ground tissue, and the like), or any portion thereof. Plant parts of the present disclosure can be viable, nonviable, regenerable, and/or non-regenerable. A "propagule" can include any plant part that can grow into an entire plant.

As used herein, a "locus" is a chromosomal locus or region where a polymorphic nucleic acid, trait determinant, gene, or marker is located. A "locus" can be shared by two homologous chromosomes to refer to their corresponding locus or region.

As used herein, an "allele" refers to an alternative nucleic acid sequence of a gene or at a particular locus (e.g., a nucleic acid sequence of a gene or locus that is different than other alleles for the same gene or locus). Such an allele can be considered (i) wild-type or (ii) mutant if one or more mutations or edits are present in the nucleic acid sequence of the mutant allele relative to the wild-type allele. A mutant or edited allele for a gene may have a reduced or eliminated activity or expression level for the gene relative to the wild-type allele. According to present embodiments, a mutant or edited allele for a gene may have an inversion or antisense sequence that may be complementary to another portion of the gene and/or a coding sequence of another copy or allele of the gene and/or another gene. For diploid organisms such as corn, a first allele can occur on one chromosome, and a second allele can occur at the same locus on a second homologous chromosome. If one allele at a locus on one chromosome of a plant is a mutant or edited allele and the other corresponding allele on the homologous chromosome of the plant is wild-type, then the plant is described as being heterozygous for the mutant or edited allele. However, if both alleles at a locus are mutant or edited alleles, then the plant is described as being homozygous for the mutant or edited alleles. A plant homozygous for mutant alleles at a locus may comprise the same mutant or edited allele or different mutant or edited alleles if heteroallelic or biallelic.

As used herein, an "endogenous locus" refers to a locus at its natural and original chromosomal location. As used herein, the "endogenous GA20 oxidase_3 locus" refers to the GA20 oxidase_3 genic locus at its original chromosomal location. As used herein, the "endogenous GA20 oxidase_5 locus" refers to the GA20 oxidase_5 genic locus at its original chromosomal location.

As used herein, a "gene" refers to a nucleic acid sequence forming a genetic and functional unit and coding for one or more sequence-related RNA and/or polypeptide molecules. A gene generally contains a coding region operably linked to appropriate regulatory sequences that regulate the expression of a gene product (e.g., a polypeptide or a functional RNA). A gene can have various sequence elements, including, but not limited to, a promoter, an untranslated region (UTR), exons, introns, and other upstream or downstream regulatory sequences.

As used herein, in the context of a protein-coding gene, an "exon" refers to a segment of a DNA or RNA molecule containing information coding for a protein or polypeptide sequence.

As used herein, an "intron" of a gene refers to a segment of a DNA or RNA molecule, which does not contain information coding for a protein or polypeptide, and which is first transcribed into a RNA sequence but then spliced out from a mature RNA molecule.

As used herein, an "untranslated region (UTR)" of a gene refers to a segment of a RNA molecule or sequence (e.g., a mRNA molecule) expressed from a gene (or transgene), but excluding the exon and intron sequences of the RNA molecule. An "untranslated region (UTR)" also refers a DNA segment or sequence encoding such a UTR segment of a RNA molecule. An untranslated region can be a 5'-UTR or a 3'-UTR depending on whether it is located at the 5' or 3' end of a DNA or RNA molecule or sequence relative to a coding region of the DNA or RNA molecule or sequence (i.e., upstream or downstream of the exon and intron sequences, respectively).

As used herein, the term "expression" refers to the biosynthesis of a gene product, and typically the transcription and/or translation of a nucleotide sequence, such as an endogenous gene, a heterologous gene, a transgene or a RNA and/or protein coding sequence, in a cell, tissue, organ, or organism, such as a plant, plant part or plant cell, tissue or organ.

As used herein, a "stem-loop structure" refers to a secondary structure in a RNA molecule having a double stranded region (e.g., stem) made up by two annealing RNA strands, sequences or segments of the RNA molecule, connected by a single stranded intervening RNA sequence of the RNA molecule (e.g., a loop or hairpin). A "stem-loop structure" of a RNA molecule can have a more complicated secondary RNA structure, for example, comprising self-annealing double stranded RNA sequences having internal mismatches, bulges and/or loops.

As used herein, a "native sequence" refers to a nucleic acid sequence naturally present in its original chromosomal location.

As used herein, a "wild-type gene" or "wild-type allele" refers to a gene or allele having a sequence or genotype that is most common in a particular plant species or another sequence or genotype having only natural variations, polymorphisms, or other silent mutations relative to the most common sequence or genotype that do not significantly impact the expression and activity of the gene or allele. Indeed, a "wild-type" gene or allele contains no variation, polymorphism, or any other type of mutation that substantially affects the normal function, activity, expression, or phenotypic consequence of the gene or allele relative to the most common sequence or genotype.

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. For purposes of calculating "percent identity" between DNA and RNA sequences, a uracil (U) of a RNA sequence is considered identical to a thymine (T) of a DNA sequence. If the window of comparison is defined as a region of alignment between two or more sequences (i.e., excluding nucleotides at the 5' and 3' ends of aligned polynucleotide sequences, or amino acids at the N-terminus and C-terminus of aligned protein sequences, that are not identical between the compared sequences), then the "percent identity" may also be referred to as a "percent alignment identity". If the "percent identity" is being calculated in relation to a reference sequence without a particular comparison window being specified, then the percent identity is determined by dividing the number of matched positions over the region of alignment by the total length of the reference sequence. Accordingly, for purposes of the present disclosure, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

For optimal alignment of sequences to calculate their percent identity, various pair-wise or multiple sequence alignment algorithms and programs are known in the art, such as ClustalW, or Basic Local Alignment Search Tool® (BLAST®), etc., that may be used to compare the sequence identity or similarity between two or more nucleotide or protein sequences. Although other alignment and comparison methods are known in the art, the alignment between two sequences (including the percent identity ranges described above) may be as determined by the ClustalW or BLAST® algorithm, see, e.g., Chenna R. et al., "Multiple sequence alignment with the Clustal series of programs," *Nucleic Acids Research* 31: 3497-3500 (2003); Thompson J D et al., "Clustal W: Improving the sensitivity of progressive multiple sequence alignment through sequence weighting, position-specific gap penalties and weight matrix choice," *Nucleic Acids Research* 22: 4673-4680 (1994); and Larkin M A et al., "Clustal W and Clustal X version 2.0*,*" *Bioinformatics* 23: 2947-48 (2007); and Altschul, S. F., Gish, W., Miller, W., Myers, E. W. & Lipman, D. J. (1990) "Basic local alignment search tool." *J. Mol. Biol.* 215:403-410 (1990), the entire contents and disclosures of which are incorporated herein by reference.

The terms "percent complementarity" or "percent complementary", as used herein in reference to two nucleotide sequences, is similar to the concept of percent identity but refers to the percentage of nucleotides of a query sequence that optimally base-pair or hybridize to nucleotides of a subject sequence when the query and subject sequences are linearly arranged and optimally base paired without secondary folding structures, such as loops, stems or hairpins. Such a percent complementarity may be between two DNA strands, two RNA strands, or a DNA strand and a RNA strand. The "percent complementarity" is calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences may be determined based on the known pairings of nucleotide bases, such as G-C, A-T, and A-U, through hydrogen bonding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present disclosure, when two sequences (query and subject) are optimally base-paired (with allowance for mismatches or non-base-paired nucleotides but without folding or secondary structures), the "percent complementarity" for the query sequence is equal to the number of base-paired positions between the two sequences divided by the total number of positions in the query sequence over its length (or by the number of positions in the query sequence over a comparison window), which is then multiplied by 100%.

As used herein, with respective to a given sequence, a "complement", a "complementary sequence" and a "reverse complement" are used interchangeably. All three terms refer to the inversely complementary sequence of a nucleotide sequence, i.e. to a sequence complementary to a given sequence in reverse order of the nucleotides. As an example, the reverse complement of a nucleotide sequence having the sequence 5'-atggttc-3' is 5'-gaaccat-3'.

As used herein, the term "antisense" refers to DNA or RNA sequences that are complementary to a specific DNA or RNA sequence. Antisense RNA molecules are single-stranded nucleic acids which can combine with a sense RNA strand or sequence or mRNA to form duplexes due to complementarity of the sequences. The term "antisense strand" refers to a nucleic acid strand that is complementary to the "sense" strand. The "sense strand" of a gene or locus is the strand of DNA or RNA that has the same sequence as a RNA molecule transcribed from the gene or locus (with the exception of Uracil in RNA and Thymine in DNA).

As used herein, an "inverted genomic fragment" refers to a genomic segment that is inverted in the genome such that the original sense strand and antisense strand sequences are reversed or switched in the opposite orientation for the entire genomic segment.

As used herein, in the context of a "corresponding endogenous sequence" or a "corresponding endogenous DNA segment," an endogenous sequence or endogenous DNA segment is considered to correspond to another sequence or DNA segment (e.g., an non-endogenous, introduced or inserted sequence or DNA segment) when the sequences or DNA segments share sufficient sequence homology, identity, or complementarity.

As used herein, unless specified otherwise, the relative location of two sequence elements of a genic locus, when expressed as "upstream," "downstream," "at the 5' end," or "at the 3' end," is determined based on the direction of the transcription activity associated with that genic locus. For example, for two transcribed genomic DNA elements, their relative location is based on their sense strand where the first genomic DNA element is upstream or at the 5' end of the second genomic DNA element when the first genomic DNA element is transcribed first.

The term "operably linked" refers to a functional linkage between a promoter or other regulatory element and an associated transcribable DNA sequence or coding sequence of a gene (or transgene), such that the promoter, etc., operates or functions to initiate, assist, affect, cause, and/or promote the transcription and expression of the associated transcribable DNA sequence or coding sequence, at least in certain cell(s), tissue(s), developmental stage(s), and/or condition(s). Two transcribable DNA sequences can also be "operably linked" to each other if their transcription is subject to the control of a common promoter or other regulatory element.

As used herein, an "encoding region" or "coding region" refers to a portion of a polynucleotide that encodes a functional unit or molecule (e.g., without being limiting, a mRNA, protein, or non-coding RNA sequence or molecule). An "encoding region" or "coding region" can contain, for example, one or more exons, one or more introns, a 5'-UTR, a 3'-UTR, or any combination thereof.

As used herein, "adjacent" refers to a nucleic acid sequence that is in close proximity, or next to another nucleic acid sequence. In one aspect, adjacent nucleic acid sequences are physically linked. In another aspect, adjacent nucleic acid sequences or genes are immediately next to each other such that there are no intervening nucleotides between a first nucleic acid sequence and a second nucleic acid sequence. In an aspect, a first gene and a second gene are adjacent to each other if they are separated by less than 50,000, less than 25,000, less than 10,000, less than 9000, less than 8000, less than 7000, less than 6000, less than 5000, less than 4000, less than 3000, less than 2500, less than 2000, less than 1750, less than 1500, less than 1250, less than 1000, less than 900, less than 800, less than 700, less than 600, less than 500, less than 400, less than 300, less than 200, less than 100, less than 75, less than 50, less than 25, less than 20, less than 10, less than 5, less than 4, less than 3, less than 2, or less than 1 nucleotide.

As used herein, a "targeted genome editing technique" refers to any method, protocol, or technique that allows the precise and/or targeted editing of a specific location in a genome of a plant (i.e., the editing is largely or completely non-random) using a site-specific nuclease, such as a meganuclease, a zinc-finger nuclease (ZFN), an RNA-guided endonuclease (e.g., the CRISPR/Cas9 system), a TALE (transcription activator-like effector)-endonuclease (TALEN), a recombinase, or a transposase. As used herein, "editing" or "genome editing" refers to generating a targeted mutation, deletion, inversion or substitution of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides of an endogenous plant genome nucleic acid sequence. As used herein, "editing" or "genome editing" also encompasses the targeted insertion or site-directed integration of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 750, at least 1000, at least 1500, at least 2000, at least 2500, at least 3000, at least 4000, at least 5000, at least 10,000, or at least 25,000 nucleotides into the endogenous genome of a plant. An "edit" or "genomic edit" in the singular refers to one such targeted mutation, deletion, inversion, substitution or insertion, whereas "edits" or "genomic edits" refers to two or more targeted mutation(s), deletion(s), inversion(s), substitution(s) and/or insertion(s), with each "edit" being introduced via a targeted genome editing technique.

As used herein, "modified" in the context of a plant, plant seed, plant part, plant cell, and/or plant genome, refers to a plant, plant seed, plant part, plant cell, and/or plant genome comprising an engineered change in the expression level and/or coding sequence of one or more genes of interest relative to a wild-type or control plant, plant seed, plant part, plant cell, and/or plant genome. Indeed, the term "modified" may further refer to a plant, plant seed, plant part, plant cell, and/or plant genome having one or more inversions, deletions, antisense insertions, or combinations thereof affecting expression of one or more endogenous GA oxidase genes, such as one or more endogenous GA20 oxidase genes, introduced through chemical mutagenesis, transposon insertion or excision, or any other known mutagenesis technique, or introduced through genome editing. In an aspect, a modified plant, plant seed, plant part, plant cell, and/or plant genome can comprise one or more transgenes. For clarity, therefore, a modified plant, plant seed, plant part, plant cell, and/or plant genome includes a mutated, edited and/or transgenic plant, plant seed, plant part, plant cell, and/or plant genome having a modified expression level, expression pattern, and/or coding sequence of one or more GA oxidase gene(s) relative to a wild-type or control plant, plant seed, plant part, plant cell, and/or plant genome. Modified plants can be homozygous or heterozygous for any given mutation or edit, and/or may be bi-allelic or heteroallelic at a GA oxidase gene locus. A modified plant is bi-allelic or heteroallelic for a GA oxidase gene if each copy of the GA oxidase gene is a different allele (i.e., comprises different mutation(s) and/or edit(s)), wherein each allele lowers the expression level and/or activity of the GA oxidase gene. Modified plants, plant parts, seeds, etc., may have been subjected to mutagenesis, genome editing or site-directed integration (e.g., without being limiting, via methods using site-specific nucleases), genetic transformation (e.g., without being limiting, via methods of *Agrobacterium* transformation or microprojectile bombardment), or a combination thereof. Such "modified" plants, plant seeds, plant parts, and plant cells include plants, plant seeds, plant parts, and plant cells that are offspring or derived from "modified" plants, plant seeds, plant parts, and plant cells that retain the molecular change (e.g., change in expression level and/or activity) to the one or more GA oxidase genes. A modified seed provided herein may give rise to a modified plant provided herein. A modified plant, plant seed, plant part, plant cell, or plant genome provided herein may comprise a recombinant DNA construct or vector or genome edit as provided herein. A "modified plant product" may be any product made from a modified plant, plant part, plant cell, or plant chromosome provided herein, or any portion or component thereof.

As used herein, the term "control plant" (or likewise a "control" plant seed, plant part, plant cell and/or plant genome) refers to a plant (or plant seed, plant part, plant cell and/or plant genome) that is used for comparison to a modified plant (or modified plant seed, plant part, plant cell and/or plant genome) and has the same or similar genetic background (e.g., same parental lines, hybrid cross, inbred line, testers, etc.) as the modified plant (or plant seed, plant part, plant cell and/or plant genome), except for a transgenic event and/or genome edit(s) (e.g., an inversion or antisense insertion) affecting one or more GA oxidase genes. For example, a control plant may be an inbred line that is the same as the inbred line used to make the modified plant, or a control plant may be the product of the same hybrid cross of inbred parental lines as the modified plant, except for the absence in the control plant of any transgenic or genome edit(s) affecting one or more GA oxidase genes. Similarly, an unmodified control plant refers to a plant that shares a substantially similar or essentially identical genetic background as a modified plant, but without the one or more engineered changes to the genome (e.g., transgene, mutation or edit) of the modified plant. For purposes of comparison to a modified plant, plant seed, plant part, plant cell and/or plant genome, a "wild-type plant" (or likewise a "wild-type" plant seed, plant part, plant cell and/or plant genome) refers to a non-transgenic and non-genome edited control plant, plant seed, plant part, plant cell and/or plant genome. As used herein, a "control" plant, plant seed, plant part, plant cell and/or plant genome may also be a plant, plant seed, plant part, plant cell and/or plant genome having a similar (but not the same or identical) genetic background to a modified plant, plant seed, plant part, plant cell and/or plant genome, if deemed sufficiently similar for comparison of the characteristics or traits to be analyzed.

As used herein, a "target site" for genome editing refers to the location of a polynucleotide sequence within a plant genome that is bound and cleaved by a site-specific nuclease introducing a double stranded break (or single-stranded nick) into the nucleic acid backbone of the polynucleotide sequence and/or its complementary DNA strand. A target site may comprise at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides. A "target site" for a RNA-guided nuclease may comprise the sequence of either complementary strand of a double-stranded nucleic acid (DNA) molecule or chromosome at the target site. A site-specific nuclease may bind to a target site, such as via a non-coding guide RNA (e.g., without being limiting, a CRISPR RNA (crRNA) or a single-guide RNA (sgRNA) as described further below). A non-coding guide RNA provided herein may be complementary to a target site (e.g., complementary to either strand of a double-stranded nucleic acid molecule or chromosome at the target site). It will be appreciated that perfect identity or complementarity may not be required for a non-coding guide RNA to bind or hybridize to a target site. For example, at least 1, at least 2, at least 3, at least 4, at least 5, at least 6, at least 7, or at least 8 mismatches (or more) between a target site and a non-coding RNA may be tolerated. A "target site" also refers to the location of a polynucleotide sequence within a plant genome that is bound and cleaved by another site-specific nuclease that may not be guided by a non-coding RNA molecule, such as a meganuclease, zinc finger nuclease (ZFN), or a transcription activator-like effector nuclease (TALEN), to introduce a double stranded break (or single-stranded nick) into the polynucleotide sequence and/or its complementary DNA strand. As used herein, a "target region" or a "targeted region" refers to a polynucleotide sequence or region that is flanked by two or more target sites. Without being limiting, in some embodiments a target region may be subjected to a mutation, deletion, insertion or inversion. As used herein, "flanked" when used to describe a target region of a polynucleotide sequence or molecule, refers to two or more target sites of the polynucleotide sequence or molecule surrounding the target region, with one target site on each side of the target region.

As used herein, a "donor template", which may be a recombinant DNA donor template, is defined as a nucleic acid molecule having a nucleic acid template or insertion sequence for site-directed, targeted insertion or recombination into the genome of a plant cell via repair of a nick or double-stranded DNA break in the genome of a plant cell. For example, a "donor template" may be used for site-directed integration of a DNA segment encoding an antisense sequence of interest, or as a template to introduce a mutation, such as an insertion, deletion, etc., into a target site within the genome of a plant. A targeted genome editing technique provided herein may comprise the use of one or more, two or more, three or more, four or more, or five or more donor templates. A "donor template" may be a single-stranded or double-stranded DNA or RNA molecule or plasmid. An "insertion sequence" of a donor template is a sequence designed for targeted insertion into the genome of a plant cell, which may be of any suitable length. For example, the insertion sequence of a donor template may be between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000, between 20 and 10,000, between 50 and 250, between 50 and 500, between 50 and 1000, between 50 and 5000, between 50 and 10,000, between 100 and 250, between 100 and 500, between 100 and 1000, between 100 and 5000, between 100 and 10,000, between 250 and 500, between 250 and 1000, between 250 and 5000, or between 250 and 10,000 nucleotides or base pairs in length. A donor template may also have at least one homology sequence or homology arm, such as two homology arms, to direct the integration of a mutation or insertion sequence into a target site within the genome of a plant via homologous recombination, wherein the homology sequence or homology arm(s) are identical or complementary, or have a percent identity or percent complementarity, to a sequence at or near the target site within the genome of the plant. When a donor template comprises homology arm(s) and an insertion sequence, the homology arm(s) will flank or surround the insertion sequence of the donor template.

A donor template may be linear or circular and may be single-stranded or double-stranded. A donor template may be delivered to the cell as a naked nucleic acid (e.g., via particle bombardment), as a complex with one or more delivery agents (e.g., liposomes, proteins, poloxamers, T-strand encapsulated with proteins, etc.), or contained in a bacterial or viral delivery vehicle, such as, for example, *Agrobacterium tumefaciens* or a geminivirus, respectively. An insertion sequence of a donor template or insertion sequence provided herein may comprise a transcribable DNA sequence or segment that may be transcribed into all or a portion of an RNA molecule, such as an antisense sequence or portion of a RNA molecule.

As used herein, the terms "suppress," "suppression," "inhibit," "inhibition," "inhibiting", and "downregulation" refer to a lowering, reduction or elimination of the expression level of a mRNA and/or protein encoded by a target gene in a plant, plant cell or plant tissue at one or more stage(s) of plant development, as compared to the expression level of such target mRNA and/or protein in a wild-type or control plant, cell or tissue at the same stage(s) of plant development. A target gene may be suppressed in a plant or plant tissue through one or more different mechanisms as provided herein. According to some embodiments, a modified plant is provided having a GA20 oxidase gene expression level, such as a GA20 oxidase 3 and/or GA20 oxidase 5 gene expression level(s), that is/are reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant. According to some embodiments, a modified plant is provided having a GA20 oxidase gene expression level, such as a GA20 oxidase 3 and/or GA20 oxidase 5 gene expression level(s), that is/are reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant.

According to some embodiments, a modified plant is provided having a GA20 oxidase mRNA level, such as a GA20 oxidase 3 and/or GA20 oxidase 5 mRNA level(s), that is/are reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant. According to some embodiments, a modified plant is provided having a GA20 oxidase mRNA expression level, such as a GA20 oxidase 3 and/or GA20 oxidase 5 mRNA level(s), that is/are reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant. According to some embodiments, a modified plant is provided having a GA20 oxidase protein expression level, such as a GA20 oxidase 3 and/or GA20 oxidase 5 protein level(s), that is/are reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant. According to some embodiments, a modified plant is provided having a GA20 oxidase protein expression level, such as a GA20 oxidase 3 and/or GA20 oxidase 5 protein level(s), that is/are reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant.

As used herein, an "intervening region" or "intervening sequence" refers to a polynucleotide sequence between a physically linked first polynucleotide sequence and second polynucleotide sequence. The intervening sequence may form a loop, and the first and second sequences may hybridize to form a stem, of a stem-loop structure. In one aspect, an intervening region or intervening sequence comprises at least 1, at least 2, at least 3, at least 4, at least 5, at least 10, at least 25, at least 50, at least 100, at least 150, at least 200, at least 250, at least 500, at least 1000, at least 1250, at least 1500, at least 1750, at least 2000, at least 2500, at least 3000, at least 4000, at least 5000, at least 6000, at least 7000, at least 8000, at least 9000, at least 10,000, at least 15,000, at least 20,000, at least 25,000, or at least 50,000 nucleotides. In one aspect, an intervening region or intervening sequence comprises a DNA sequence. In one aspect, an intervening region or intervening sequence comprises an RNA sequence. In one aspect, an intervening region or intervening sequences comprises an endogenous or native nucleic acid sequence. In another aspect, an intervening region or intervening sequences comprises a transgenic or exogenous nucleic acid sequence. In one aspect, an intervening region or intervening sequences comprises an endogenous or native nucleic acid sequence and a transgenic or exogenous nucleic acid sequence.

GA oxidases in cereal plants consist of a family of related GA oxidase genes. For example, corn has a family of at least nine GA20 oxidase genes that includes GA20 oxidase_1, GA20 oxidase 2, GA20 oxidase 3, GA20 oxidase 4, GA20 oxidase 5, GA20 oxidase_6, GA20 oxidase_7, GA20 oxidase_8, and GA20 oxidase_9. The DNA and protein sequences by SEQ ID NOs for each of GA20 oxidase_3 and GA20 oxidase_5 are provided in Table 1.

For the GA20 oxidase_3 gene, SEQ ID NO: 1 provides 3000 nucleotides upstream of the GA20 oxidase_3 5'-UTR; nucleotides 3001-3096 correspond to the 5'-UTR; nucleotides 3097-3665 correspond to the first exon; nucleotides 3666-3775 correspond to the first intron; nucleotides 3776-4097 correspond to the second exon; nucleotides 4098-5314 correspond to the second intron; nucleotides 5315-5584 correspond to the third exon; and nucleotides 5585-5800 correspond to the 3'-UTR. SEQ ID NO: 1 also provides 3000 nucleotides downstream of the end of the 3'-UTR (nucleotides 5801-8800).

For the GA20 oxidase_5 gene, SEQ ID NO: 5 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 5 also provides 3000 nucleotides downstream of the end of the 3'-UTR (nucleotides 5860-8859).

It was previously shown that suppression of GA20 oxidase gene(s) and/or targeting of a subset of one or more GA oxidase genes via transgenic suppression (e.g., an artificial microRNA-mediated suppression of both GA20 oxidase_3 and GA20 oxidase_5 genes) can be effective in achieving a short stature, semi-dwarf phenotype with increased resistance to lodging, but without reproductive off-types in the ear. See PCT Application No. PCT/US2017/047405 and U.S. application Ser. No. 15/679,699, both filed on Aug. 17, 2017, and published as WO/2018/035354 and US20180051295, respectively. Furthermore, knocking out GA20 oxidase_3, GA20 oxidase_5, or both genes via genome editing also can cause reduced plant height and increased lodging resistance, and impacts GA hormonal levels. See PCT Application Nos. PCT/US2019/018128, PCT/US2019/018131, and PCT/US2019/018133, all filed on Feb. 15, 2019.

Dominant alleles are alleles that mask the contribution of a second allele (e.g., a wild-type allele) at the same locus (e.g., a second allele of the same gene). A dominant allele may be referred to as semi-dominant if the masking effect is partial or incomplete. Sometimes, a dominant allele of one locus or gene can also have dominant effects over another locus or gene. Dominant negative alleles, or antimorphs, are alleles that produce altered gene products acting in opposition to wild-type allelic function. For example, a dominant negative allele can abrogate or suppress the normal function of a wild-type allele or gene product in a heterozygous state.

Creation of dominant alleles that work in a heterozygous state, can speed up effective trait development, deployment,

TABLE 1

DNA and protein sequences by sequence identifier for GA20 oxidase_3 and GA20 oxidase_5 genes in corn.

| GA20 oxidase Gene | Genomic DNA | cDNA | Coding Sequence (CDS) | Protein |
| --- | --- | --- | --- | --- |
| GA20 oxidase_3 | SEQ ID NO: 1 | SEQ ID NO: 2 | SEQ ID NO: 3 | SEQ ID NO: 4 |
| GA20 oxidase_5 | SEQ ID NO: 5 | SEQ ID NO: 6 | SEQ ID NO: 7 | SEQ ID NO: 8 |

A wild-type genomic DNA sequence of the GA20 oxidase_3 locus from a reference genome is provided in SEQ ID NO: 1, and a wild-type genomic DNA sequence of the GA20 oxidase_5 locus from a reference genome is provided in SEQ ID NO: 5.

and launch of gene editing-derive products in hybrid crops such as corn. Dominant negative alleles have the potential advantage of providing a positive or beneficial plant trait in a heterozygous state—e.g., when present in a single copy. As a result, the dominant negative mutant allele can be introduced through crossing into a progeny plant from a single parent without having to introduce the allele from both parent plants as with a recessive allele. The present disclosure provides methods and compositions to selectively edit a genome of a corn plant to create a dominant allele that produces a beneficial trait in a plant.

In an aspect, this disclosure provides a modified corn plant or a method for producing such modified corn plant, where the modified corn plant has a dominant allele (for example, a semi-dominant allele) at the endogenous GA20 oxidase_3 locus or the endogenous GA20 oxidase_5 locus, such dominant allele suppressing or opposing the expression or function of one or more wide-type alleles of the endogenous GA20 oxidase_3 locus, the endogenous GA20 oxidase_5 locus, or both.

In an aspect, this disclosure provides a modified corn plant, or plant part thereof, comprising a mutant allele at one or both of the endogenous GA20 oxidase_3 and the endogenous GA20 oxidase_5 loci, wherein the mutant allele comprises a DNA insertion encoding an antisense RNA sequence, wherein the mutant allele produces a RNA transcript comprising the antisense RNA sequence and is able to suppress or oppose the expression of a wild-type allele of the GA20 oxidase_3 locus or gene, GA20 oxidase_5 locus or gene, or both. In an aspect, an antisense RNA sequence encoded by the DNA insertion is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7. In an aspect, a first mutant allele at one or both of the endogenous GA20 oxidase_3 and the endogenous GA20 oxidase_5 loci is able to suppress or oppose the expression of a second mutant allele of the GA20 oxidase_3 locus or gene, GA20 oxidase_5 locus or gene, or both.

In another aspect, this disclosure provides a modified corn plant, or plant part thereof, comprising a single mutant allele at only one of the endogenous GA20 oxidase_3 and endogenous GA20 oxidase_5 loci, wherein the single mutant allele comprises a DNA segment encoding an antisense RNA sequence, and wherein the mutant allele encodes a RNA (mRNA) molecule comprising the antisense RNA sequence that is able to suppress or oppose the expression of one or both wild-type allele(s) of the GA20 oxidase_3 and/or GA20 oxidase_5 locus/loci or gene(s) in the modified corn plant, or plant part thereof. In an aspect, a DNA insertion is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7.

Further provided herein are methods of generating dominant alleles of genes or gene regions using targeted genome editing techniques. Also provided herein are cells, tissues or explants generated by such methods and compositions used in such methods. The instant description further provides modified plants regenerated from cells, tissues or explants subjected to the methods provided herein any their progeny, and any plant parts thereof. In one aspect, a dominant allele of a gene provided herein is able to suppress the expression of a wild-type and/or mutant allele(s) of the same and/or different locus/loci or gene(s) in a heterozygous state.

According to aspects of the present disclosure, a mutant or edited allele of the endogenous GA20 oxidase_3 (GA20ox3) or endogenous GA20 oxidase_5 (GA20 ox5) gene or locus is provided comprising a DNA segment encoding an antisense RNA sequence. It is contemplated that a RNA transcript expressed from such an edited GA20ox3 or GA20ox5 allele comprising the antisense RNA sequence may affect the expression level(s) of the GA20 oxidase_3 and/or endogenous GA20 oxidase_5 gene(s) through different mechanisms, such as nonsense mediated decay, non-stop decay, no-go decay, DNA or histone methylation or other epigenetic changes, inhibition or decreased efficiency of transcription and/or translation, ribosomal interference, interference with mRNA processing or splicing, and/or ubiquitin-mediated protein degradation via the proteasome. See, e.g., Nickless, A. et al., "Control of gene expression through the nonsense-mediated RNA decay pathway", *Cell Biosci* 7:26 (2017); Karamyshev, A. et al., "Lost in Translation: Ribosome-Associated mRNA and Protein Quality Controls", *Frontiers in Genetics* 9:431 (2018); Inada, T., "Quality controls induced by aberrant translation", *Nucleic Acids Res* 48:3 (2020); and Szadeczky-Kardoss, I. et al., "The nonstop decay and the RNA silencing systems operate cooperatively in plants", *Nucleic Acids Res* 46:9 (2018), the entire contents and disclosures of which are incorporated herein by reference. Each of these different mechanisms may act alternatively or in addition to RNA interference (RNAi), transcriptional gene silencing, and/or post transcriptional gene silencing (PTGS) mechanisms. See, e.g., Wilson, R. C. et al., "Molecular Mechanisms of RNA Interference", *Annu Rev Biophysics* 42:217-39 (2013); and Guo, Q. et al., "RNA Silencing in Plants: Mechanism, Technologies and Applications in Horticulture Crops", *Current Genomics* 17:476-489 (2016), the entire contents and disclosures of which is incorporated herein by reference. Some of the above mechanisms may reduce expression of the edited allele itself, while others may also reduce the expression of other copy/-ies or allele(s) of the endogenous GA20 oxidase_3 and/or GA20 oxidase_5 locus/loci or gene(s). Indeed, it is envisioned that the presence of an antisense or inversion sequence, such as a DNA segment encoding an antisense RNA sequence, in an edited endogenous GA20 oxidase_3 or GA20 oxidase_5 gene, locus or allele may not only reduce or eliminate its own expression and/or activity level, but may also have a dominant or semi-dominant effect(s) on the other copy/-ies or allele(s) of the endogenous GA20 oxidase_3 and/or GA20 oxidase_5 locus/loci or gene(s). Such dominant or semi-dominant effect(s) on the GA20 oxidase_3 and/or GA20 oxidase_5 gene(s) may operate through non-canonical suppression mechanisms that do not involve RNAi and/or formation of targeted small RNAs at a significant or detectable level, provided however that the data in Example 5 below do support the formation of small RNA molecules.

In an aspect, the present disclosure provides a modified corn plant, or plant part thereof, comprising a mutant allele of the endogenous GA20 oxidase_3 locus or gene, wherein the mutant allele comprises a DNA segment inserted into the endogenous GA20 oxidase_3 locus or gene, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and where the mutant allele produces a RNA transcript comprising the antisense RNA sequence. In an aspect, a GA20 oxidase_3 mutant allele is able to suppress the expression of a wild-type (or mutant) allele of the endogenous GA20 oxidase_3 locus or gene, a wild-type (or mutant) allele of the endogenous GA20 oxidase_5 locus or gene, or both. In another aspect, a GA20 oxidase_3 mutant allele suppresses the expression of a wild-type (or mutant) allele of the endogenous GA20 oxidase_3 locus or gene, a wild-type (or mutant) allele of the endogenous GA20 oxidase_5 locus or gene, or both. In a further aspect, a RNA transcript produced by a GA20 oxidase_3 mutant allele provided herein, further comprises one or more sequence elements of the endogenous GA20 oxidase_3 locus or gene selected from the group consisting of 5' UTR, $1^{st}$ exon, $1^{st}$ intron, 2nd exon, $2^{nd}$ intron, $3^{rd}$ exon, 3' UTR, and any portion thereof.

In an aspect, an inserted DNA segment in a GA20 oxidase_3 mutant allele comprises a nucleotide sequence originating from the endogenous GA20 oxidase_3 locus. In another aspect, an inserted DNA segment in a GA20 oxidase_3 mutant allele corresponds to an inverted genomic fragment of the endogenous GA20 oxidase_3 locus. In an aspect, an inserted DNA segment in a GA20 oxidase_3 mutant allele comprises a nucleotide sequence originating from the endogenous GA20 oxidase_5 locus. In another aspect, an inserted DNA segment in a GA20 oxidase_3 mutant allele corresponds to an inverted genomic fragment of the endogenous GA20 oxidase_5 locus.

In an aspect, at least a portion of the antisense RNA sequence in a RNA transcript produced by a GA20 oxidase_3 mutant allele, is at least 70%, at least 75%, at least 80%, at least 85%, at least 90%, at least 95%, at least 96%, at least 97%, at least 98%, at least 99%, or 100% complementary to a corresponding endogenous sequence of the RNA transcript. In another aspect, a corresponding endogenous sequence of the RNA transcript is at least 85%, at least 90%, at least 95%, at least 96%, at least 97%, at least 98%, at least 99%, or 100% identical to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7. In a further aspect, an antisense RNA sequence encoded by an inserted DNA segment in a GA20 oxidase_3 mutant allele hybridizes to the corresponding endogenous sequence of a RNA transcript produced by the GA20 oxidase_3 mutant allele. In a further aspect, a RNA transcript produced by the GA20 oxidase_3 mutant allele comprises a hairpin or stem-loop structure comprising an antisense RNA sequence hybridized to a corresponding endogenous sequence of the RNA transcript.

In an aspect, a GA20 oxidase_3 mutant allele provided here comprises an inserted DNA segment having a length of at least 15, 16, 17, 18, 19, 20, 21, 22, 23, 24, 25, 30, 35, 40, 45, 50, 75, 100, 125, 150, 175, 200, 250, 300, 400, 500, 750, 1000, 1500, 2000, 2500, or 3000 nucleotides. In another aspect, a GA20 oxidase_3 mutant allele comprises an inserted DNA segment having a length of at most, less than or less than or equal to 25, 50, 100, 150, 200, 250, 300, 400, 500, 750, 1000, 1500, 2000, 2500, or 3000 nucleotides. In another aspect, a GA20 oxidase_3 mutant allele comprises an inserted DNA segment having a length of between 20 and 25, between 20 and 30, between 20 and 35, between 20 and 40, between 20 and 50, between 50 and 100, between 100 and 200, between 200 and 300, between 300 and 400, between 400 and 500, between 500 and 750, between 750 and 1000, between 1000 and 1500, between 1500 and 2000, between 2000 and 3000, or between 3000 and 4000 nucleotides. In another aspect, a GA20 oxidase_3 mutant allele comprises an inserted DNA segment having a length between 20 and 4000, between 50 and 4000, between 100 and 4000, between 200 and 4000, between 300 and 4000, between 400 and 4000, between 500 and 4000, between 750 and 4000, between 1000 and 4000, between 1500 and 4000, or between 2000 and 4000 nucleotides. In another aspect, a GA20 oxidase_3 mutant allele comprises an inserted DNA segment having a length between 20 and 100, between 20 and 200, between 20 and 300, between 20 and 400, between 20 and 500, between 20 and 750, between 20 and 1000, between 20 and 1500, between 20 and 2000, between 20 and 3000, or between 20 and 4000 nucleotides. In another aspect, a GA20 oxidase_3 mutant allele comprises an inserted DNA segment having a length between 20 and 3000, between 50 and 2000, between 100 and 1500, between 200 and 1000, between 300 and 750, or between 400 and 750 nucleotides.

In an aspect, a GA20 oxidase_3 mutant allele comprises a DNA segment inserted near or adjacent to a corresponding endogenous DNA segment of the endogenous GA20 oxidase_3 locus or gene. In another aspect, an antisense RNA sequence encoded by an inserted DNA segment hybridizes to a corresponding endogenous sequence of the RNA transcript encoded by the corresponding endogenous DNA segment. In a further aspect, an antisense RNA sequence forms a stem-loop structure with the corresponding endogenous sequence of the RNA transcript.

In an aspect, a GA20 oxidase_3 mutant allele comprises an inserted DNA segment and a corresponding endogenous DNA segment separated by an intervening DNA sequence. In another aspect, an intervening DNA sequence has a length of at least 1, 2, 3, 4, 5, 6, 7, 8, 9, 10, 11, 12, 13, 14, 15, 20, 25, 30, 40, 50, 75, 100, 150, 200, 250, 300, 400, 500, 750, 1000, 1500, 2000, 3000, or 4000 consecutive nucleotides. In a further aspect, an intervening sequence has at most, less than or less than or equal to 1, 2, 3, 4, 5, 6, 7, 8, 9, 10, 11, 12, 13, 14, 15, 20, 25, 30, 40, 50, 75, 100, 150, 200, 250, 300, 400, 500, 750, 1000, 1500, 2000, 3000, or 4000 consecutive nucleotides. In another aspect, an intervening DNA sequence has a length between 2 and 10, between 10 and 20, between 20 and 50, between 50 and 100, between 100 and 200, between 200 and 300, between 300 and 400, between 400 and 500, between 500 and 750, between 750 and 1000, between 1000 and 1500, between 1500 and 2000, between 2000 and 3000, or between 3000 and 4000 nucleotides. In another aspect, an intervening DNA sequence has a length between 2 and 4000, between 10 and 4000, between 20 and 4000, between 50 and 4000, between 100 and 4000, between 200 and 4000, between 300 and 4000, between 400 and 4000, between 500 and 4000, between 750 and 4000, between 1000 and 4000, between 1500 and 4000, or between 2000 and 4000 nucleotides. In another aspect, an intervening DNA sequence has a length between 10 and 20, between 10 and 50, between 10 and 100, between 10 and 200, between 10 and 300, between 10 and 400, between 10 and 500, between 10 and 750, between 10 and 1000, between 10 and 1500, between 10 and 2000, between 10 and 3000, or between 10 and 4000 nucleotides. In another aspect, an intervening DNA sequence has a length between 20 and 3000, between 50 and 2000, between 100 and 1500, between 200 and 1000, between 300 and 750, or between 400 and 750 nucleotides.

In a further aspect, an intervening DNA sequence encodes an intervening RNA sequence between the antisense RNA sequence and the corresponding endogenous sequence of the RNA transcript. In an aspect, an intervening RNA sequence forms the loop portion of a stem-loop structure of a RNA transcript produced by a GA20 oxidase_3 mutant allele. In another aspect, a stem-loop secondary structure contains a near-perfect-complement stem with mismatches. In a further aspect, a stem-loop secondary structure contains a perfect-complement stem with no mismatch. In another aspect, an intervening DNA sequence comprises a native sequence of the endogenous GA20 oxidase_3 locus or gene. In an aspect, an intervening DNA sequence comprises an exogenous sequence inserted into the endogenous GA20 oxidase_3 locus or gene. In another aspect, an intervening DNA sequence comprises an intron sequence. In a further aspect, an intervening DNA sequence does not contain an intron sequence.

In an aspect, a GA20 oxidase_3 mutant allele comprises an inserted DNA segment located upstream (5') of the corresponding endogenous DNA segment. In another aspect, a GA20 oxidase_3 mutant allele comprises an inserted DNA segment is located downstream (3') of the corresponding endogenous DNA segment.

In an aspect, a GA20 oxidase_3 mutant allele comprises an inserted DNA segment within a region selected from the group consisting of 5' untranslated region (UTR), $1^{st}$ exon, $1^{st}$ intron, $2^{nd}$ exon, $2^{nd}$ intron, $3^{rd}$ exon and 3' UTR of the endogenous GA20 oxidase_3 locus or gene, and a combination thereof. In an aspect, a GA20 oxidase_3 mutant allele comprises an inserted DNA segment at a genomic site recognized by a targeted editing technique to create a double-stranded break (DSB). In an aspect, a GA20 oxidase_3 mutant allele further comprises a deletion of at least one portion or sequence of the endogenous GA20 oxidase_3 locus or gene.

In an aspect, a GA20 oxidase_3 mutant allele comprises an inserted DNA segment, where the sense strand of the inserted DNA segment comprises a sequence that is at least 70%, at least 75%, at least 80%, at least 85%, at least 90%, at least 95%, at least 96%, at least 97%, at least 98%, at least 99%, or 100% complementary to an exon sequence, or a portion thereof, of the endogenous GA20 oxidase_3 or GA20 oxidase_5 locus or gene. In an aspect, a GA20 oxidase_3 mutant allele comprises an inserted DNA segment, where the sense strand of the inserted DNA segment comprises a sequence that is at least 70%, at least 75%, at least 80%, at least 85%, at least 90%, at least 95%, at least 96%, at least 97%, at least 98%, at least 99%, or 100% complementary to an intron sequence, or a portion thereof, of the endogenous GA20 oxidase_3 or GA20 oxidase_5 locus or gene. In another aspect, a GA20 oxidase_3 mutant allele comprises an inserted DNA segment, where the sense strand of the inserted DNA segment comprises a sequence that is at least 70%, at least 75%, at least 80%, at least 85%, at least 90%, at least 95%, at least 96%, at least 97%, at least 98%, at least 99%, or 100% complementary to an untranslated region (UTR) sequence, or a portion thereof, of the endogenous GA20 oxidase_3 or GA20 oxidase_5 locus or gene. In a further aspect, a GA20 oxidase_3 mutant allele comprises an inserted DNA segment, where the sense strand of the inserted DNA segment comprises a sequence that is at least 70%, at least 75%, at least 80%, at least 85%, at least 90%, at least 95%, at least 96%, at least 97%, at least 98%, at least 99%, or 100% complementary to at least a portion of an exon sequence and at least a portion of an intron sequence of the endogenous GA20 oxidase_3 or GA20 oxidase_5 locus or gene, the exon sequence and the intron sequence being contiguous within the endogenous locus or gene.

In an aspect, a GA20 oxidase_3 mutant allele comprises an inserted DNA segment comprising a sequence having at least 70%, at least 75%, at least 80%, at least 85%, at least 90%, at least 95%, at least 96%, at least 97%, at least 98%, at least 99%, or 100% identity or complementarity to one or more of SEQ ID NOs: 13, 14, 26, 28, 30, 32 and 36.

In an aspect, a modified corn plant, or plant part thereof, is homozygous for a mutant allele(s) at the endogenous GA20 oxidase_3 locus, the endogenous GA20 oxidase_5 locus, or both. In another aspect, a modified corn plant, or plant part thereof, is heterozygous for a mutant allele(s) at the endogenous GA20 oxidase_3 locus, the endogenous GA20 oxidase_5 locus, or both. In another aspect, a modified corn plant, or plant part thereof, is trans-heterozygous for allele(s) at the endogenous GA20 oxidase_3 locus, the endogenous GA20 oxidase_5 locus, or both. In a further aspect, a modified corn plant, or plant part thereof, is heterozygous for a first mutant allele at one of the endogenous GA20 oxidase_3 locus and the endogenous GA20 oxidase_5 locus, and homozygous for a second mutant allele at the other locus of the endogenous GA20 oxidase_3 locus and the endogenous GA20 oxidase_5 locus.

In an aspect, the present disclosure provides a modified corn plant, or plant part thereof, comprising a mutant allele of the endogenous GA20 oxidase_5 locus or gene, wherein the mutant allele comprises a DNA segment inserted into the endogenous GA20 oxidase_5 locus or gene, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and where the mutant allele produces a RNA transcript comprising the antisense RNA sequence. In an aspect, a GA20 oxidase_5 mutant allele is able to suppress the expression of a wild-type (or mutant) allele of the endogenous GA20 oxidase_3 locus or gene, a wild-type (or mutant) allele of the endogenous GA20 oxidase_5 locus or gene, or both. In another aspect, a GA20 oxidase_5 mutant allele suppresses the expression of a wild-type (or mutant) allele of the endogenous GA20 oxidase_3 locus or gene, a wild-type (or mutant) allele of the endogenous GA20 oxidase_5 locus or gene, or both. In a further aspect, a RNA transcript produced by a GA20 oxidase_5 mutant allele provided herein, further comprises one or more sequence elements of the endogenous GA20 oxidase_5 locus or gene selected from the group consisting of 5' UTR, $1^{st}$ exon, $1^{st}$ intron, $2^{nd}$ exon, $2^{nd}$ intron, $3^{rd}$ exon, 3' UTR, and any portion thereof.

In an aspect, a DNA segment inserted into the endogenous GA20 oxidase_5 locus or gene comprises a nucleotide sequence originating from the endogenous GA20 oxidase_3 locus or gene. In another aspect, an inserted DNA segment in a GA20 oxidase_5 mutant allele corresponds to an inverted genomic fragment of the endogenous GA20 oxidase_3 locus or gene. In an aspect, an inserted DNA segment in a GA20 oxidase_5 mutant allele comprises a nucleotide sequence originating from the endogenous GA20 oxidase_5 locus or gene. In another aspect, an inserted DNA segment in a GA20 oxidase_5 mutant allele corresponds to an inverted genomic fragment of the endogenous GA20 oxidase_5 locus or gene.

In an aspect, at least a portion of the antisense RNA sequence in a RNA transcript produced by a GA20 oxidase_5 mutant allele, is at least 70%, at least 75%, at least 80%, at least 85%, at least 90%, at least 95%, at least 96%, at least 97%, at least 98%, at least 99%, or 100% complementary to a corresponding endogenous sequence of the RNA transcript. In another aspect, a corresponding endogenous sequence of the RNA transcript is at least 85%, at least 90%, at least 95%, at least 96%, at least 97%, at least 98%, at least 99%, or 100% identical to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7. In a further aspect, an antisense RNA sequence encoded by an inserted DNA segment in a GA20 oxidase_5 mutant allele hybridizes to the corresponding endogenous sequence of a RNA transcript produced by the GA20 oxidase_5 mutant allele. In a further aspect, a RNA transcript produced by the GA20 oxidase_3 mutant allele comprises a hairpin or stem-loop structure comprising an antisense RNA sequence hybridized to a corresponding endogenous sequence of the RNA transcript.

In an aspect, a GA20 oxidase_5 mutant allele provided here comprises an inserted DNA segment having a length of at least 15, 16, 17, 18, 19, 20, 21, 22, 23, 24, 25, 30, 35, 40, 45, 50, 75, 100, 125, 150, 175, 200, 250, 300, 400, 500, 750, 1000, 1500, 2000, 2500, or 3000 nucleotides. In another aspect, a GA20 oxidase_5 mutant allele comprises an inserted DNA segment having a length of at most, less than or less than or equal to 25, 50, 100, 150, 200, 250, 300, 400, 500, 750, 1000, 1500, 2000, 2500, or 3000 nucleotides. In another aspect, a GA20 oxidase_5 mutant allele comprises an inserted DNA segment having a length of between 20 and 25, between 20 and 30, between 20 and 35, between 20 and 40, between 20 and 50, between 50 and 100, between 100 and 200, between 200 and 300, between 300 and 400, between 400 and 500, between 500 and 750, between 750 and 1000, between 1000 and 1500, between 1500 and 2000, between 2000 and 3000, or between 3000 and 4000 nucleotides. In another aspect, a GA20 oxidase_5 mutant allele comprises an inserted DNA segment having a length between 20 and 4000, between 50 and 4000, between 100 and 4000, between 200 and 4000, between 300 and 4000, between 400 and 4000, between 500 and 4000, between 750 and 4000, between 1000 and 4000, between 1500 and 4000, or between 2000 and 4000 nucleotides. In another aspect, a GA20 oxidase_5 mutant allele comprises an inserted DNA segment having a length between 20 and 100, between 20 and 200, between 20 and 300, between 20 and 400, between 20 and 500, between 20 and 750, between 20 and 1000, between 20 and 1500, between 20 and 2000, between 20 and 3000, or between 20 and 4000 nucleotides. In another aspect, a GA20 oxidase_5 mutant allele comprises an inserted DNA segment having a length between 20 and 3000, between 50 and 2000, between 100 and 1500, between 200 and 1000, between 300 and 750, or between 400 and 750 nucleotides.

In an aspect, a GA20 oxidase_5 mutant allele comprises a DNA segment inserted near or adjacent to a corresponding endogenous DNA segment of the endogenous GA20 oxidase_5 locus or gene. In another aspect, an antisense RNA sequence encoded by an inserted DNA segment hybridizes to a corresponding endogenous sequence of the RNA transcript encoded by the corresponding endogenous DNA segment. In a further aspect, an antisense RNA sequence forms a stem-loop structure with the corresponding endogenous sequence of the RNA transcript.

In an aspect, a GA20 oxidase_5 mutant allele comprises an inserted DNA segment and a corresponding endogenous DNA segment separated by an intervening DNA sequence. In another aspect, an intervening DNA sequence has a length of at least 1, 2, 3, 4, 5, 6, 7, 8, 9, 10, 11, 12, 13, 14, 15, 20, 25, 30, 40, 50, 75, 100, 150, 200, 250, 300, 400, 500, 750, 1000, 1500, 2000, 3000, or 4000 consecutive nucleotides. In a further aspect, an intervening sequence has at most, less than or less than or equal to 1, 2, 3, 4, 5, 6, 7, 8, 9, 10, 11, 12, 13, 14, 15, 20, 25, 30, 40, 50, 75, 100, 150, 200, 250, 300, 400, 500, 750, 1000, 1500, 2000, 3000, or 4000 consecutive nucleotides. In another aspect, an intervening DNA sequence has a length between 2 and 10, between 10 and 20, between 20 and 50, between 50 and 100, between 100 and 200, between 200 and 300, between 300 and 400, between 400 and 500, between 500 and 750, between 750 and 1000, between 1000 and 1500, between 1500 and 2000, between 2000 and 3000, or between 3000 and 4000 nucleotides. In another aspect, an intervening DNA sequence has a length between 2 and 4000, between 10 and 4000, between 20 and 4000, between 50 and 4000, between 100 and 4000, between 200 and 4000, between 300 and 4000, between 400 and 4000, between 500 and 4000, between 750 and 4000, between 1000 and 4000, between 1500 and 4000, or between 2000 and 4000 nucleotides. In another aspect, an intervening DNA sequence has a length between 10 and 20, between 10 and 50, between 10 and 100, between 10 and 200, between 10 and 300, between 10 and 400, between 10 and 500, between 10 and 750, between 10 and 1000, between 10 and 1500, between 10 and 2000, between 10 and 3000, or between 10 and 4000 nucleotides. In another aspect, an intervening DNA sequence has a length between 20 and 3000, between 50 and 2000, between 100 and 1500, between 200 and 1000, between 300 and 750, or between 400 and 750 nucleotides.

In a further aspect, an intervening DNA sequence encodes an intervening RNA sequence between the antisense RNA sequence and the corresponding endogenous sequence of the RNA transcript. In an aspect, an intervening RNA sequence forms the loop portion of a stem-loop structure of a RNA transcript produced by a GA20 oxidase_5 mutant allele. In another aspect, a stem-loop secondary structure contains a near-perfect-complement stem with mismatches. In a further aspect, a stem-loop secondary structure contains a perfect-complement stem with no mismatch. In another aspect, an intervening DNA sequence comprises a native sequence of the endogenous GA20 oxidase_5 locus or gene. In an aspect, an intervening DNA sequence comprises an exogenous sequence inserted into the endogenous GA20 oxidase_5 locus or gene. In another aspect, an intervening DNA sequence comprises an intron sequence. In a further aspect, an intervening DNA sequence does not contain an intron sequence.

In an aspect, a GA20 oxidase_5 mutant allele comprises an inserted DNA segment located upstream (5') of the corresponding endogenous DNA segment. In another aspect, a GA20 oxidase_5 mutant allele comprises an inserted DNA segment is located downstream (3') of the corresponding endogenous DNA segment.

In an aspect, a GA20 oxidase_5 mutant allele comprises an inserted DNA segment within a region selected from the group consisting of 5' untranslated region (UTR), $1^{st}$ exon, $1^{st}$ intron, $2^{nd}$ exon, $2^{nd}$ intron, $3^{rd}$ exon and 3' UTR of the endogenous GA20 oxidase_5 locus or gene, and a combination thereof. In an aspect, a GA20 oxidase_5 mutant allele comprises an inserted DNA segment at a genomic site recognized by a targeted editing technique to create a double-stranded break (DSB). In an aspect, a GA20 oxidase_5 mutant allele further comprises a deletion of at least one portion or sequence of the endogenous GA20 oxidase_5 locus or gene.

In an aspect, a GA20 oxidase_5 mutant allele comprises an inserted DNA segment, where the sense strand of the inserted DNA segment comprises a sequence that is at least 70%, at least 75%, at least 80%, at least 85%, at least 90%, at least 95%, at least 96%, at least 97%, at least 98%, at least 99%, or 100% complementary to an exon sequence, or a portion thereof, of the endogenous GA20 oxidase_3 or GA20 oxidase_5 locus or gene. In an aspect, a GA20 oxidase_5 mutant allele comprises an inserted DNA segment, where the sense strand of the inserted DNA segment comprises a sequence that is at least 70%, at least 75%, at least 80%, at least 85%, at least 90%, at least 95%, at least 96%, at least 97%, at least 98%, at least 99%, or 100% complementary to an intron sequence, or a portion thereof, of the endogenous GA20 oxidase_3 or GA20 oxidase_5 locus or gene. In another aspect, a GA20 oxidase_5 mutant allele comprises an inserted DNA segment, where the sense strand of the inserted DNA segment comprises a sequence that is at least 70%, at least 75%, at least 80%, at least 85%, at least 90%, at least 95%, at least 96%, at least 97%, at least 98%, at least 99%, or 100% complementary to an untranslated region (UTR) sequence, or a portion thereof, of the endogenous GA20 oxidase_3 or GA20 oxidase_5 locus or gene. In a further aspect, a GA20 oxidase_5 mutant allele comprises an inserted DNA segment, where the sense strand of the inserted DNA segment comprises a sequence that is at least 70%, at least 75%, at least 80%, at least 85%, at least 90%, at least 95%, at least 96%, at least 97%, at least 98%, at least 99%, or 100% complementary to at least a portion of an exon sequence and at least a portion of an intron sequence of the endogenous GA20 oxidase_3 or GA20 oxidase_5 locus or gene, the exon sequence and the intron sequence being contiguous within the endogenous locus or gene.

In an aspect, a GA20 oxidase_5 mutant allele comprises an inserted DNA segment comprising a sequence having at least 70%, at least 75%, at least 80%, at least 85%, at least 90%, at least 95%, at least 96%, at least 97%, at least 98%, at least 99%, or 100% identity or complementarity to one or more of SEQ ID NOs: 13, 14, 26, 28, 30, 32 and 36.

In an aspect, the present disclosure provides a method for producing a mutant allele of the endogenous GA20 oxidase_3 or GA20 oxidase_5 locus or gene, the method comprising: (a) generating a double-stranded break (DSB) in the endogenous GA20 oxidase_3 or GA20 oxidase_5 locus or gene in a corn cell using a targeted editing technique; and (b) inserting a DNA segment into the endogenous GA20 oxidase_3 or GA20 oxidase_5 locus or gene at the DSB, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_3 locus or gene produces a RNA transcript comprising the antisense RNA sequence. In another aspect, a method further comprises regenerating or developing a corn plant from the corn cell.

In an aspect, the present disclosure provides a method for producing a mutant allele of the endogenous GA20 oxidase_5 locus, the method comprising: (a) generating a first double-stranded break and a second double strand break in the endogenous GA20 oxidase_5 locus in a corn cell using a targeted editing technique; (b) inserting a DNA segment between the first double-stranded break and the second double-stranded break, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_5 locus produces a RNA transcript comprising the antisense RNA sequence.

In an aspect, the present disclosure provides a method for producing a mutant allele of the endogenous GA20 oxidase_3 locus, the method comprising: (a) generating a first double-stranded break and a second double strand break in the endogenous GA20 oxidase_3 locus in a corn cell using a targeted editing technique; (b) inserting a DNA segment between the first double-stranded break and the second double-stranded break, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_3 locus produces a RNA transcript comprising the antisense RNA sequence.

In an aspect, a targeted editing technique used herein comprises the use of at least one site-specific nuclease. In an aspect, a site-specific nuclease is selected from the group consisting of a zinc-finger nuclease, a meganuclease, an RNA-guided nuclease, a TALE-nuclease, a recombinase, a transposase, and any combination thereof. In another aspect, a site-specific nuclease is a RNA-guided nuclease selected from the group consisting of a Cas9 nuclease or a variant thereof, and a Cpf1 nuclease or a variant thereof.

In an aspect, a method provided herein inserts into an endogenous GA20 oxidase_3 or GA20 oxidase_5 locus or gene a DNA segment originating from the endogenous GA20 oxidase_3 locus or gene or the endogenous GA20 oxidase_5 locus or gene. In another aspect, an inserted DNA segment is provided in a donor template. In a further aspect, an inserted DNA segment is provided by excising the DNA segment from another chromosomal location (e.g., transfragment template).

According to further embodiments, methods are provided for transforming a plant cell, tissue or explant with a recombinant DNA molecule or construct encoding one or more molecules required for targeted genome editing (e.g., guide RNA(s) and/or site-directed nuclease(s)). Numerous methods for transforming chromosomes or plastids in a plant cell with a recombinant DNA molecule or construct are known in the art, which may be used according to method embodiments of the present invention to produce a transgenic plant cell and plant. Any suitable method or technique for transformation of a plant cell known in the art may be used according to present methods. Effective methods for transformation of plants include bacterially mediated transformation, such as *Agrobacterium*-mediated or *Rhizobium*-mediated transformation, and microprojectile or particle bombardment-mediated transformation. A variety of methods are known in the art for transforming explants with a transformation vector via bacterially mediated transformation or microprojectile or particle bombardment and then subsequently culturing, etc., those explants to regenerate or develop transgenic plants. Other methods for plant transformation, such as microinjection, electroporation, vacuum infiltration, pressure, sonication, silicon carbide fiber agitation, PEG-mediated transformation, etc., are also known in the art.

Methods of transforming plant cells and explants are well known by persons of ordinary skill in the art. Methods for transforming plant cells by microprojectile bombardment with particles coated with recombinant DNA are provided, for example, in U.S. Pat. Nos. 5,550,318; 5,538,880, 6,160, 208; 6,399,861; and 6,153,812, and *Agrobacterium*-mediated transformation is described, for example, in U.S. Pat. Nos. 5,159,135; 5,824,877; 5,591,616; 6,384,301; 5,750, 871; 5,463,174; and 5,188,958, all of which are incorporated herein by reference. Additional methods for transforming plants can be found in, for example, Compendium of Transgenic Crop Plants (2009) Blackwell Publishing. Any suitable method of plant transformation known or later developed in the art can be used to transform a plant cell or explant with any of the nucleic acid molecules, constructs or vectors provided herein.

Recipient cell(s) or explant or cellular targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, a callus cell, a chloroplast, a stomatal cell, a trichome cell, a root hair cell, a storage root cell, or a vascular tissue cell, a seed, embryo, meristem, cotyledon, hypocotyl, endosperm, root, shoot, stem, node, callus, cell suspension, protoplast, flower, leaf, pollen, anther, ovary, ovule, pericarp, bud, and/or vascular tissue, or any transformable portion of any of the foregoing. For plant transformation, any target cell(s), tissue(s), explant(s), etc., that may be used to receive a recombinant DNA transformation vector or molecule of the present disclosure may be collectively be referred to as an "explant" for transformation. Preferably, a transformable or transformed explant cell or tissue may be further developed or regenerated into a plant. Any cell or explant from which a fertile plant can be grown or regenerated is contemplated as a useful recipient cell or explant for practice of this disclosure (i.e., as a target explant for transformation). Callus can be initiated or created from various tissue sources, including, but not limited to, embryos or parts of embryos, non-embryonic seed tissues, seedling apical meristems, microspores, and the like. Any cells that are capable of proliferating as callus may serve as recipient cells for transformation. Transformation methods and materials for making transgenic plants (e.g., various media and recipient target cells or explants and methods of transformation and subsequent regeneration of into transgenic plants) are known in the art.

Transformation or editing of a target plant material or explant may be practiced in tissue culture on nutrient media, for example a mixture of nutrients that allow cells to grow in vitro or cell culture. Modified explants, cells or tissues may be subjected to additional culturing steps, such as callus induction, selection, regeneration, etc., as known in the art. Transformation or editing may also be carried out without creation or use of a callus tissue. Transformed or edited cells, tissues or explants containing a DNA sequence insertion or edit may be grown, developed or regenerated into transgenic plants in culture, plugs, or soil according to methods known in the art. Modified plants may be further crossed to themselves or other plants to produce modified plant seeds and progeny. A modified plant may also be prepared by crossing a first plant comprising a DNA sequence or construct or an edit (e.g., an antisense sequence or inversion) with a second plant lacking the insertion. For example, a DNA sequence or inversion may be introduced into a first plant line that is amenable to transformation or editing, which may then be crossed with a second plant line to introgress the DNA sequence or edit (e.g., inversion) into the second plant line. Progeny of these crosses can be further back crossed into the desirable line multiple times, such as through 6 to 8 generations or back crosses, to produce a progeny plant with substantially the same genotype as the original parental line, but for the introduction of the DNA sequence or edit.

In an aspect, this disclosure provides a method for generating a corn plant comprising: (a) fertilizing at least one female corn plant with pollen from a male corn plant, wherein the female corn plant and/or the male corn plant comprises a mutant (e.g., edited) allele of an endogenous GA20 oxidase locus or gene as provided herein, wherein the mutant allele comprises a DNA segment inserted into the endogenous GA20 oxidase locus, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 or 5-7, and wherein the mutant allele of the endogenous GA20 oxidase locus produces a RNA transcript comprising the antisense RNA sequence; and (b) obtaining at least one seed produced by said fertilizing of step (a). According to an aspect, the at least one seed in step (b) comprises the mutant allele of the endogenous GA20 oxidase locus or gene from the female corn plant. In another aspect, the method further comprises (c) growing the at least one seed obtained in step (b) to generate at least one progeny corn plant comprising said mutant allele. In an aspect, the at least one progeny corn plant obtained in step (c) is heterozygous or homozygous for the mutant allele. According to some aspects, such methods may comprise (d) selecting at least on progeny corn plant that comprises the mutant allele, which may comprise selecting at least on progeny corn plant that is homozygous or heterozygous for the mutant allele.

In an aspect, the female corn plant is homozygous for a mutant allele. In another aspect, the female corn plant is heterozygous for the mutant allele. In an aspect, the male corn plant lacks the mutant allele. In an aspect, the male corn plant is heterozygous for the mutant allele. In an aspect, the male corn plant is homozygous for the mutant allele. In an aspect, the at least one progeny corn plant has a shorter plant height and/or improved lodging resistance relative to a control plant lacking the mutant allele. In an aspect, the at least one progeny corn plant has a shorter plant height and/or improved lodging resistance relative to the male or female corn plant. In an aspect, the female corn plant is an inbred corn plant. In an aspect, the female corn plant is a hybrid corn plant. In an aspect, the male corn plant is an inbred corn plant. In an aspect, the male corn plant is a hybrid corn plant. In an aspect, the female corn plant is an elite corn plant line. In an aspect, the male corn plant is an elite corn plant line.

In an aspect, the female corn plant is a first inbred corn line or variety, and the male corn plant is a different, second inbred corn line or variety. In an aspect, the female corn plant and the male corn plant are grown in a greenhouse or growth chamber. In an aspect, the female corn plant and the male corn plant are grown outdoors or in a field. In an aspect, the female corn plant has been detasseled. In an aspect, the female corn plant is a cytoplasmically male sterile corn plant.

As used herein, "detasseled" corn refers to corn where the pollen-producing flowers, or tassels, have been removed. Detasseling is typically performed before the tassel can shed pollen. Detasseling can be accomplished via machine detasseling, manual detasseling, or a combination of both machine and manual detasseling. Detasseling can remove the uppermost leaves of the corn plant along with the developing tassel. Detasseled corn plants retain their female flowers, which may be pollinated by pollen from another corn plant and eventually produce kernels on the ear. In an aspect, a corn plant provided herein is a detasseled corn plant.

As an alternative to chemical treatment, corn plants (or female corn plants) can be made male sterile through genetic crosses and inheritance causing cytoplasmic male sterility. As used herein, the term "cytoplasmic male sterility" or "CMS" refers to a condition where a corn plant is partially or fully incapable of producing functional pollen. As known in the art, cytoplasmic male sterility is a maternally inherited trait that is commonly associated with unusual open reading frames within the mitochondrial genome which cause cytoplasmic dysfunction. In an aspect, a corn plant or female corn plant provided herein is a cytoplasmic male sterile corn plant.

A modified plant, plant part, cell, or explant provided herein may be of an elite variety or an elite line. An elite variety or an elite line refers to a variety that has resulted from breeding and selection for superior agronomic performance. A modified (e.g., edited) plant, cell, or explant provided herein may be a hybrid plant, cell, or explant. As used herein, a "hybrid" is created by crossing two plants from different varieties, lines, inbreds, or species, such that the progeny comprises genetic material from each parent. Skilled artisans recognize that higher order hybrids can be generated as well. For example, a first hybrid can be made by crossing Variety A with Variety B to create a A×B hybrid, and a second hybrid can be made by crossing Variety C with Variety D to create an C×D hybrid. The first and second hybrids can be further crossed to create the higher order hybrid (A×B)×(C×D) comprising genetic information from all four parent varieties.

A plant selectable marker transgene in a transformation vector or construct of the present disclosure may be used to assist in the selection of transformed cells or tissue due to the presence of a selection agent, such as an antibiotic or herbicide, wherein the plant selectable marker transgene provides tolerance or resistance to the selection agent. Thus, the selection agent may bias or favor the survival, development, growth, proliferation, etc., of transformed cells expressing the plant selectable marker gene, such as to increase the proportion of transformed cells or tissues in the $R_0$ plant. Commonly used plant selectable marker genes include, for example, those conferring tolerance or resistance to antibiotics, such as kanamycin and paromomycin (npt/l), hygromycin B (aph IV), streptomycin or spectinomycin (aadA) and gentamycin (aac3 and aacC4), or those conferring tolerance or resistance to herbicides such as glufosinate (bar or pat), dicamba (DMO) and glyphosate (aroA or EPSPS). Plant screenable marker genes may also be used, which provide an ability to visually screen for transformants, such as luciferase or green fluorescent protein (GFP), or a gene expressing a beta glucuronidase or uidA gene (GUS) for which various chromogenic substrates are known. In some embodiments, a vector or polynucleotide provided herein comprises at least one selectable marker gene selected from the group consisting of npt/II, aph IV, aadA, aac3, aacC4, bar, pat, DMO, EPSPS, aroA, GFP, and GUS. Plant transformation may also be carried out in the absence of selection during one or more steps or stages of culturing, developing or regenerating transformed explants, tissues, plants and/or plant parts.

According to present embodiments, methods for transforming a plant cell, tissue or explant with a recombinant DNA molecule or construct may further include site-directed or targeted integration. According to these methods, a portion of a recombinant DNA donor template molecule (i.e., an insertion sequence) may be inserted or integrated at a desired site or locus within the plant genome. The insertion sequence of the donor template may comprise a transgene or construct, such as a transgene or transcribable DNA sequence of interest that encodes an anti-sense RNA sequence targeting an endogenous GA oxidase gene for suppression. The donor template may also have one or two homology arms flanking the insertion sequence to promote the targeted insertion event through homologous recombination and/or homology-directed repair. Each homology arm may be at least 70%, at least 75%, at least 80%, at least 85%, at least 90%, at least 95%, at least 96%, at least 97%, at least 99% or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence within the genome of a monocot or cereal plant (e.g., a corn plant). Thus, a recombinant DNA molecule of the present disclosure may comprise a donor template for site-directed or targeted integration of a transgene or construct, such as a transgene or transcribable DNA sequence of interest that encodes an anti-sense RNA sequence targeting an endogenous GA oxidase gene for suppression, into the genome of a plant. In an aspect, this disclosure provides a recombinant DNA construct comprising one or more donor templates. In an aspect, a recombinant DNA construct comprising a one or more donor templates can be introduced to a plant cell, plant tissue or plant part provided herein using any plant transformation technique known in the art.

Any site or locus within the genome of a plant may potentially be chosen for site-directed integration of a transgene, construct or transcribable DNA sequence provided herein. For site-directed integration, a double-strand break (DSB) or nick may first be made at a selected genomic locus with a site-specific nuclease, such as, for example, a zinc-finger nuclease, an engineered or native meganuclease, a TALE-endonuclease, or an RNA-guided endonuclease (e.g., Cas9 or Cpf1). Any method known in the art for site-directed integration may be used. In the presence of a donor template molecule with an insertion sequence, the DSB or nick may then be repaired by homologous recombination between homology arm(s) of the donor template and the plant genome, or by non-homologous end joining (NHEJ), resulting in site-directed integration of the insertion sequence into the plant genome to create the targeted insertion event at the site of the DSB or nick. Thus, site-specific insertion or integration of a transgene, construct or sequence may be achieved.

A site-specific nuclease provided herein may be selected from the group consisting of a zinc-finger nuclease (ZFN), a meganuclease, an RNA-guided endonuclease, a TALE-endonuclease (TALEN), a recombinase, a transposase, or any combination thereof. See, e.g., Khandagale, K. et al., "Genome editing for targeted improvement in plants," *Plant Biotechnol Rep* 10: 327-343 (2016); and Gaj, T. et al., "ZFN, TALEN and CRISPR/Cas-based methods for genome engineering," *Trends Biotechnol*. 31(7): 397-405 (2013), the contents and disclosures of which are incorporated herein by reference. A recombinase may be a serine recombinase attached to a DNA recognition motif, a tyrosine recombinase attached to a DNA recognition motif or other recombinase enzyme known in the art. A recombinase or transposase may be a DNA transposase or recombinase attached to a DNA binding domain. A tyrosine recombinase attached to a DNA recognition motif may be selected from the group consisting of a Cre recombinase, a Flp recombinase, and a Tnp1 recombinase. According to some embodiments, a Cre recombinase or a Gin recombinase provided herein is tethered to a zinc-finger DNA binding domain. In another embodiment, a serine recombinase attached to a DNA recognition motif provided herein is selected from the group consisting of a PhiC31 integrase, an R4 integrase, and a TP-901 integrase. In another embodiment, a DNA transposase attached to a DNA binding domain provided herein is selected from the group consisting of a TALE-piggyBac and TALE-Mutator.

According to embodiments of the present disclosure, an RNA-guided endonuclease may be selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, and homologs or modified versions thereof, Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo) and homologs or modified versions thereof. According to some embodiments, an RNA-guided endonuclease may be a Cas9 or Cpf1 (or Cas12a) enzyme.

In an aspect, a site-specific nuclease provided herein is selected from the group consisting of a zinc-finger nuclease, a meganuclease, an RNA-guided nuclease, a TALE-nuclease, a recombinase, a transposase, or any combination thereof. In another aspect, a site-specific nuclease provided herein is selected from the group consisting of a Cas9 or a Cpf1 (or Cas12a). In another aspect, a site-specific nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, CasX, CasY, a homolog thereof, or a modified version thereof. In another aspect, an RNA-guided nuclease provided herein is selected from the group consisting of a Cas9 or a Cpf1 (or Cas12a). In another aspect, an RNA guided nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, CasX, CasY, a homolog thereof, or a modified version thereof. In another aspect, a method and/or a composition provided herein comprises at least one, at least two, at least three, at least four, at least five, at least six, at least seven, at least eight, at least nine, or at least ten site-specific nucleases. In yet another aspect, a method and/or a composition provided herein comprises at least one, at least two, at least three, at least four, at least five, at least six, at least seven, at least eight, at least nine, or at least ten polynucleotides encoding at least one, at least two, at least three, at least four, at least five, at least six, at least seven, at least eight, at least nine, or at least ten site-specific nucleases.

For RNA-guided endonucleases, a guide RNA (gRNA) molecule is further provided to direct the endonuclease to a target site in the genome of the plant via base-pairing or hybridization to cause a DSB or nick at or near the target site. The gRNA may be transformed or introduced into a plant cell or tissue (perhaps along with a nuclease, or nuclease-encoding DNA molecule, construct or vector) as a gRNA molecule, or as a recombinant DNA molecule, construct or vector comprising a transcribable DNA sequence encoding the guide RNA operably linked to a plant-expressible promoter. As understood in the art, a "guide RNA" may comprise, for example, a CRISPR RNA (crRNA), a single-chain guide RNA (sgRNA), or any other RNA molecule that may guide or direct an endonuclease to a specific target site in the genome. A "single-chain guide RNA" (or "sgRNA") is a RNA molecule comprising a crRNA covalently linked a tracrRNA by a linker sequence, which may be expressed as a single RNA transcript or molecule. The guide RNA comprises a guide or targeting sequence that is identical or complementary to a target site within the plant genome, such as at or near a GA oxidase gene. A protospacer-adjacent motif (PAM) may be present in the genome immediately adjacent and upstream to the 5' end of the genomic target site sequence complementary to the targeting sequence of the guide RNA—i.e., immediately downstream (3') to the sense (+) strand of the genomic target site (relative to the targeting sequence of the guide RNA) as known in the art. See, e.g., Wu, X. et al., "Target specificity of the CRISPR-Cas9 system," *Quant Biol*. 2(2): 59-70 (2014), the content and disclosure of which is incorporated herein by reference. The genomic PAM sequence on the sense (+) strand adjacent to the target site (relative to the targeting sequence of the guide RNA) may comprise 5'-NGG-3'. However, the corresponding sequence of the guide RNA (i.e., immediately downstream (3') to the targeting sequence of the guide RNA) may generally not be complementary to the genomic PAM sequence. The guide RNA may typically be anon-coding RNA molecule that does not encode a protein. The guide sequence of the guide RNA may be at least 10 nucleotides in length, such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or about 12, 13, 14, 15, 16, 17, 18, 19, 20, 21, 22, 23, 24, 25 or more nucleotides in length. The guide sequence may be at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of a DNA sequence at the genomic target site.

According to some embodiments, a recombinant DNA construct or vector may comprise a first polynucleotide sequence encoding a site-specific nuclease and a second polynucleotide sequence encoding a guide RNA that may be introduced into a plant cell together via plant transformation techniques. Alternatively, two recombinant DNA constructs or vectors may be provided including a first recombinant DNA construct or vector and a second DNA construct or vector that may be introduced into a plant cell together or sequentially via plant transformation techniques, wherein the first recombinant DNA construct or vector comprises a polynucleotide sequence encoding a site-specific nuclease and the second recombinant DNA construct or vector comprises a polynucleotide sequence encoding a guide RNA. According to some embodiments, a recombinant DNA construct or vector comprising a polynucleotide sequence encoding a site-specific nuclease may be introduced via plant transformation techniques into a plant cell that already comprises (or is transformed with) a recombinant DNA construct or vector comprising a polynucleotide sequence encoding a guide RNA. Alternatively, a recombinant DNA construct or vector comprising a polynucleotide sequence encoding a guide RNA may be introduced via plant transformation techniques into a plant cell that already comprises (or is transformed with) a recombinant DNA construct or vector comprising a polynucleotide sequence encoding a site-specific nuclease. According to yet further embodiments, a first plant comprising (or transformed with) a recombinant DNA construct or vector comprising a polynucleotide sequence encoding a site-specific nuclease may be crossed with a second plant comprising (or transformed with) a recombinant DNA construct or vector comprising a polynucleotide sequence encoding a guide RNA. In an aspect, recombinant DNA constructs or vectors may be transiently transformed into a plant cell or stably transformed or integrated into the genome of a plant cell.

In an aspect, vectors comprising polynucleotides encoding a site-specific nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In an aspect, vectors comprising polynucleotides encoding a Cas9 nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

Several site-specific nucleases, such as recombinases, zinc finger nucleases (ZFNs), meganucleases, and TALENs, are not RNA-guided and instead rely on their protein structure to determine their target site for causing the DSB or nick, or they are fused, tethered or attached to a DNA-binding protein domain or motif. The protein structure of the site-specific nuclease (or the fused/attached/tethered DNA binding domain) may target the site-specific nuclease to the target site. According to many of these embodiments, non-RNA-guided site-specific nucleases, such as recombinases, zinc finger nucleases (ZFNs), meganucleases, and TALENs, may be designed, engineered and constructed according to known methods to target and bind to a target site at or near the genomic locus of an endogenous GA oxidase gene of a corn plant, such as the GA20 oxidase_3 gene or the GA20 oxidase_5 gene in corn, to create a DSB or nick at such genomic locus to knockout or knockdown expression of the GA oxidase gene via repair of the DSB or nick. For example, an engineered site-specific nuclease, such as a recombinase, zinc finger nuclease (ZFN), meganuclease, or TALEN, may be designed to target and bind to (i) a target site within the genome of a plant corresponding to a sequence within SEQ ID NO: 1, or its complementary sequence, to create a DSB or nick at the genomic locus for the GA20 oxidase_3 gene, or (ii) a target site within the genome of a plant corresponding to a sequence within SEQ ID NO: 5, or its complementary sequence, to create a DSB or nick at the genomic locus for the GA20 oxidase_5 gene, which may then lead to the creation of a mutation or insertion of a sequence at the site of the DSB or nick, through cellular repair mechanisms, which may be guided by a donor molecule or template.

In an aspect, a targeted genome editing technique described herein may comprise the use of a recombinase. In some embodiments, a tyrosine recombinase attached, etc., to a DNA recognition domain or motif may be selected from the group consisting of a Cre recombinase, a Flp recombinase, and a Tnp1 recombinase. In an aspect, a Cre recombinase or a Gin recombinase provided herein may be tethered to a zinc-finger DNA binding domain. The Flp-FRT site-directed recombination system may come from the 2p plasmid from the baker's yeast *Saccharomyces cerevisiae*. In this system, Flp recombinase (flippase) may recombine sequences between flippase recognition target (FRT) sites. FRT sites comprise 34 nucleotides. Flp may bind to the "arms" of the FRT sites (one arm is in reverse orientation) and cleaves the FRT site at either end of an intervening nucleic acid sequence. After cleavage, Flp may recombine nucleic acid sequences between two FRT sites. Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase may recombine a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete. In another aspect, a lox site provided herein is a loxP, lox 2272, loxN, lox 511, lox 5171, lox71, lox66, M2, M3, M7, or M11 site.

ZFNs are synthetic proteins consisting of an engineered zinc finger DNA-binding domain fused to a cleavage domain (or a cleavage half-domain), which may be derived from a restriction endonuclease (e.g., FokI). The DNA binding domain may be canonical (C2H2) or non-canonical (e.g., C3H or C4). The DNA-binding domain can comprise one or more zinc fingers (e.g., 2, 3, 4, 5, 6, 7, 8, 9 or more zinc fingers) depending on the target site. Multiple zinc fingers in a DNA-binding domain may be separated by linker sequence(s). ZFNs can be designed to cleave almost any stretch of double-stranded DNA by modification of the zinc finger DNA-binding domain. ZFNs form dimers from monomers composed of a non-specific DNA cleavage domain (e.g., derived from the FokI nuclease) fused to a DNA-binding domain comprising a zinc finger array engineered to bind a target site DNA sequence. The DNA-binding domain of a ZFN may typically be composed of 3-4 (or more) zinc-fingers. The amino acids at positions −1, +2, +3, and +6 relative to the start of the zinc finger α-helix, which contribute to site-specific binding to the target site, can be changed and customized to fit specific target sequences. The other amino acids may form a consensus backbone to generate ZFNs with different sequence specificities. Methods and rules for designing ZFNs for targeting and binding to specific target sequences are known in the art. See, e.g., US Patent App. Nos. 2005/0064474, 2009/0117617, and 2012/0142062, the contents and disclosures of which are incorporated herein by reference. The FokI nuclease domain may require dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. A ZFN, as used herein, is broad and includes a monomeric ZFN that can cleave double stranded DNA without assistance from another ZFN. The term ZFN may also be used to refer to one or both members of a pair of ZFNs that are engineered to work together to cleave DNA at the same site.

Without being limited by any scientific theory, because the DNA-binding specificities of zinc finger domains can be re-engineered using one of various methods, customized ZFNs can theoretically be constructed to target nearly any target sequence (e.g., at or near a GA oxidase gene in a plant genome). Publicly available methods for engineering zinc finger domains include Context-dependent Assembly (CoDA), Oligomerized Pool Engineering (OPEN), and Modular Assembly. In an aspect, a method and/or composition provided herein comprises one or more, two or more, three or more, four or more, or five or more ZFNs. In another aspect, a ZFN provided herein is capable of generating a targeted DSB or nick. In an aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection, or Agrobacterium-mediated transformation). The ZFNs may be introduced as ZFN proteins, as polynucleotides encoding ZFN proteins, and/or as combinations of proteins and protein-encoding polynucleotides.

Meganucleases, which are commonly identified in microbes, such as the LAGLIDADG family of homing endonucleases, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). According to some embodiments, a meganuclease may comprise a scaffold or base enzyme selected from the group consisting of I-CreI, I-CeuI, I-Msof, I-SceI, I-Ani, and I-DmoI. The engineering of meganucleases can be more challenging than ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity. Thus, a meganuclease may be selected or engineered to bind to a genomic target sequence in a plant, such as at or near the genomic locus of a GA oxidase gene. In an aspect, a method and/or composition provided herein comprises one or more, two or more, three or more, four or more, or five or more meganucleases. In another aspect, a meganuclease provided herein is capable of generating a targeted DSB. In an aspect, vectors comprising polynucleotides encoding one or more, two or more, three or more, four or more, or five or more meganucleases are provided to a cell by transformation methods known in the art (e.g., without being limiting, viral transfection, particle bombardment, PEG-mediated protoplast transfection or Agrobacterium-mediated transformation).

TALENs are artificial restriction enzymes generated by fusing the transcription activator-like effector (TALE) DNA binding domain to a nuclease domain (e.g., FokI). When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the transcription activator-like effector (TALE) DNA binding domain to a nuclease domain. In some aspects, the nuclease is selected from a group consisting of PvuII, MutH, TevI, FokI, AlwI, MlyI, SbfI, SdaI, StsI, CleDORF, Clo051, and Pept071. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN is also refers to one or both members of a pair of TALENs that work together to cleave DNA at the same site.

Transcription activator-like effectors (TALEs) can be engineered to bind practically any DNA sequence, such as at or near the genomic locus of a GA oxidase gene in a plant. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

PvuII, MutH, and TevI cleavage domains are useful alternatives to FokI and FokI variants for use with TALEs. PvuII functions as a highly specific cleavage domain when coupled to a TALE (see Yank et al. 2013. *PLoS One.* 8: e82539). MutH is capable of introducing strand-specific nicks in DNA (see Gabsalilow et al. 2013. *Nucleic Acids Research.* 41: e83). TevI introduces double-stranded breaks in DNA at targeted sites (see Beurdeley et al., 2013. *Nature Communications.* 4: 1762).

The relationship between amino acid sequence and DNA recognition of the TALE binding domain allows for designable proteins. Software programs such as DNAWorks can be used to design TALE constructs. Other methods of designing TALE constructs are known to those of skill in the art. See Doyle et al., *Nucleic Acids Research* (2012) 40: W117-122; Cermak et al., *Nucleic Acids Research* (2011). 39:e82; and tale-nt.cac.cornell.edu/about. In an aspect, a method and/or composition provided herein comprises one or more, two or more, three or more, four or more, or five or more TALENs. In another aspect, a TALEN provided herein is capable of generating a targeted DSB. In an aspect, vectors comprising polynucleotides encoding one or more, two or more, three or more, four or more, or five or more TALENs are provided to a cell by transformation methods known in the art (e.g., without being limiting, viral transfection, particle bombardment, PEG-mediated protoplast transfection or *Agrobacterium*-mediated transformation). See, e.g., US Patent App. Nos. 2011/0145940, 2011/0301073, and 2013/0117869, the contents and disclosures of which are incorporated herein by reference.

Embodiments of the present disclosure further include methods for making or producing modified plants described herein, such as by transformation, genome editing, mutating, crossing, etc., wherein the method comprises introducing a recombinant DNA molecule, construct or sequence of interest into a plant cell, or editing or mutating the genomic locus of an endogenous GA oxidase gene, and then regenerating or developing the modified plant from the transformed or edited plant cell, which may be performed under selection pressure. Such methods may comprise transforming a plant cell with a recombinant DNA molecule, construct or sequence of interest, and selecting for a plant having one or more altered phenotypes or traits, such as one or more of the following traits at one or more stages of development: shorter or semi-dwarf stature or plant height, shorter internode length in one or more internode(s), increased stalk/stem diameter, improved lodging resistance, reduced green snap, deeper roots, increased leaf area, earlier canopy closure, increased foliar water content and/or higher stomatal conductance under water limiting conditions, reduced anthocyanin content and/or area in leaves under normal or nitrogen or water limiting stress conditions, improved yield-related traits including a larger female reproductive organ or ear, an increase in ear weight, harvest index, yield, seed or kernel number, and/or seed or kernel weight, increased stress tolerance, such as increased drought tolerance, increased nitrogen utilization, and/or increased tolerance to high density planting, as compared to a wild type or control plant.

According to another aspect of the present disclosure, methods are provided for planting a modified plant(s) provided herein at a normal/standard or high density in field. According to some embodiments, the yield of a crop plant per acre (or per land area) may be increased by planting a modified plant of the present disclosure at a higher density in the field. As described herein, modified plants having a genome-edited GA oxidase gene, may have reduced plant height, shorter internode(s), increased stalk/stem diameter, and/or increased lodging resistance. It is proposed that modified plants may tolerate high density planting conditions since an increase in stem diameter may resist lodging and the shorter plant height may allow for increased light penetrance to the lower leaves under high density planting conditions. Thus, modified plants provided herein may be planted at a higher density to increase the yield per acre (or land area) in the field. For row crops, higher density may be achieved by planting a greater number of seeds/plants per row length and/or by decreasing the spacing between rows.

According to some embodiments, a modified crop plant may be planted at a density in the field (plants per land/field area) that is at least 5%, 10%, 15%, 20%, 25%, 50%, 75%, 100%, 125%, 150%, 175%, 200%, 225%, or 250% higher than the normal planting density for that crop plant according to standard agronomic practices. A modified crop plant may be planted at a density in the field of at least 38,000 plants per acre, at least 40,000 plants per acre, at least 42,000 plants per acre, at least 44,000 plants per acre, at least 45,000 plants per acre, at least 46,000 plants per acre, at least 48,000 plants per acre, 50,000 plants per acre, at least 52,000 plants per acre, at least 54,000 per acre, or at least 56,000 plants per acre. As an example, corn plants may be planted at a higher density, such as in a range from about 38,000 plants per acre to about 60,000 plants per acre, or about 40,000 plants per acre to about 58,000 plants per acre, or about 42,000 plants per acre to about 58,000 plants per acre, or about 40,000 plants per acre to about 45,000 plants per acre, or about 45,000 plants per acre to about 50,000 plants per acre, or about 50,000 plants per acre to about 58,000 plants per acre, or about 52,000 plants per acre to about 56,000 plants per acre, or about 38,000 plants per acre, about 42,000 plant per acre, about 46,000 plant per acre, or about 48,000 plants per acre, about 50,000 plants per acre, or about 52,000 plants per acre, or about 54,000 plant per acre, as opposed to a standard density range, such as about 18,000 plants per acre to about 38,000 plants per acre.

The height of a corn plant can be measured using a variety of methods known in the art, which may be based on a variety of anatomical locations on a corn plant. In an aspect, the height of a corn plant is measured as the distance between the soil or ground and the ligule (or collar) of the uppermost fully-expanded leaf of the corn plant. As used herein, a "fully-expanded leaf" is a leaf where the leaf blade is exposed and both the ligule and auricle are visible at the blade/sheath boundary. In another aspect, the height of a corn plant is measured as the distance between the soil or ground and the upper leaf surface of the leaf farthest from the soil or ground. In another aspect, the height of a corn plant is measured as the distance between the soil or ground and the arch of the highest corn leaf that is at least 50% developed. As used herein, an "arch of the highest corn leaf" is the highest point of the arch of the uppermost leaf of the corn plant that is curving downward. In another aspect, the height of a corn plant is measured at the first reproductive (R1) stage. Exemplary, non-limiting methods of measuring plant height include comparing photographs of corn plants to a height reference, or physically measuring individual corn plants with a suitable ruler, stick or measuring device. Unless otherwise specified, corn plant heights are mature or full growth plant heights measured at a reproductive or late vegetative stage. Those in the art recognize that, when comparing a modified corn plant to a control corn plant, the measurements must be made at the same stage of growth. It would be improper, as a non-limiting example, to compare the height of a modified corn plant at R3 stage to the height of a control corn plant at V6 stage, even if both plants had been growing for the same amount of time. Unless otherwise specified, plant height is measured at R2 growth stage from the soil level to the base of the uppermost fully expanded leaf.

As used herein, the term "ground" or "ground level" used in relation to a corn plant, such as to measure plant height, refers to the top or uppermost surface of the growth medium or soil (e.g., earth) from which the corn plant grows.

Corn plant height varies depending on the line or variety grown, whether the plant is a hybrid or inbred, and environmental conditions. Although hybrid corn plants can reach a height of over 3.6 meters tall by maturity, a height of around 2.0-2.5 meters by maturity for hybrid plants is more common. Modified corn plants provided herein have a reduced plant height compared to a control plant, such as less than 2.0 meters, less than 1.9 meters, less than 1.8 meters, less than 1.7 meters, less than 1.6 meters, or less than 1.5 meters.

According to embodiments of the present disclosure, a modified corn plant(s) is/are provided that comprise (i) a plant height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm, and/or (ii) an average stem or stalk diameter of at least 18 mm, at least 18.5 mm, at least 19 mm, at least 19.5 mm, at least 20 mm, at least 20.5 mm, at least 21 mm, at least 21.5 mm, or at least 22 mm. Stated a different way, a modified corn plant(s) is/are provided that comprise a plant height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm, and/or an average stem or stalk diameter that is greater than 18 mm, greater than 18.5 mm, greater than 19 mm, greater than 19.5 mm, greater than 20 mm, greater than 20.5 mm, greater than 21 mm, greater than 21.5 mm, or greater than 22 mm. Any such plant height trait or range that is expressed in millimeters (mm) may be converted into a different unit of measurement based on known conversions (e.g., one inch is equal to 2.54 cm or 25.4 millimeters, and millimeters (mm), centimeters (cm) and meters (m) only differ by one or more powers of ten). Thus, any measurement provided herein is further described in terms of any other comparable units of measurement according to known and established conversions. However, the exact plant height and/or stem diameter of a modified corn plant may depend on the environment and genetic background. Thus, the change in plant height and/or stem diameter of a modified corn plant may instead be described in terms of a minimum difference or percent change relative to a control plant. In an aspect, a modified corn plant does not have any significant off-types in at least one female organ or ear. A modified corn plant may further comprise at least one ear that is substantially free of male reproductive tissues or structures or other off-types. In an aspect, a modified corn plant exhibits essentially no reproductive abnormality or off-type—i.e., no significant or observable reproductive abnormality or off-type. In a further aspect, an off-type or reproductive abnormality is selected from the group consisting of male (tassel or anther) sterility, reduced kernel or seed number, and the presence of one or more masculinized or male (or male-like) reproductive structures in the female organ or ear (e.g., anther ear).

According to embodiments of the present disclosure, modified corn plants are provided that comprise a plant height during late vegetative and/or reproductive stages of development (e.g., at R3 stage) of between 1000 mm and 1800 mm, between 1000 mm and 1700 mm, between 1050 mm and 1700 mm, between 1100 mm and 1700 mm, between 1150 mm and 1700 mm, between 1200 mm and 1700 mm, between 1250 mm and 1700 mm, between 1300 mm and 1700 mm, between 1350 mm and 1700 mm, between 1400 mm and 1700 mm, between 1450 mm and 1700 mm, between 1000 mm and 1500 mm, between 1050 mm and 1500 mm, between 1100 mm and 1500 mm, between 1150 mm and 1500 mm, between 1200 mm and 1500 mm, between 1250 mm and 1500 mm, between 1300 mm and 1500 mm, between 1350 mm and 1500 mm, between 1400 mm and 1500 mm, between 1450 mm and 1500 mm, between 1000 mm and 1600 mm, between 1100 mm and 1600 mm, between 1200 mm and 1600 mm, between 1300 mm and 1600 mm, between 1350 mm and 1600 mm, between 1400 mm and 1600 mm, between 1450 mm and 1600 mm, of between 1000 mm and 2000 mm, between 1200 mm and 2000 mm, between 1200 mm and 1800 mm, between 1300 mm and 1700 mm, between 1400 mm and 1700 mm, between 1400 mm and 1600 mm, between 1400 mm and 1700 mm, between 1400 mm and 1800 mm, between 1400 mm and 1900 mm, between 1400 mm and 2000 mm, or between 1200 mm and 2500 mm, and/or an average stem diameter of between 17.5 mm and 22 mm, between 18 mm and 22 mm, between 18.5 and 22 mm, between 19 mm and 22 mm, between 19.5 mm and 22 mm, between 20 mm and 22 mm, between 20.5 mm and 22 mm, between 21 mm and 22 mm, between 21.5 mm and 22 mm, between 17.5 mm and 21 mm, between 17.5 mm and 20 mm, between 17.5 mm and 19 mm, between 17.5 mm and 18 mm, between 18 mm and 21 mm, between 18 mm and 20 mm, or between 18 mm and 19 mm. A modified corn plant may be substantially free of off-types, such as male reproductive tissues or structures in one or more ears of the modified corn plant.

According to embodiments of the present disclosure, modified corn plants are provided that have (i) a plant height that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the height of a wild-type or control plant, and/or (ii) a stem or stalk diameter that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the stem diameter of the wild-type or control plant. According to embodiments of the present disclosure, a modified corn plant may have a reduced plant height that is no more than 20%, 25%, 30%, 35%, 40%, 45%, 50%, 55%, or 60% shorter than the height of a wild-type or control plant, and/or a stem or stalk diameter that is less than (or not more than) 10%, 15%, 20%, 25%, 30%, 35%, 40%, 45%, 50%, 55%, 60%, 65%, 70%, 75%, 80%, 85%, 90%, 95%, or 100% greater than the stem or stalk diameter of a wild-type or control plant. For example, a modified plant may have (i) a plant height that is at least 10%, at least 15%, or at least 20% less or shorter (i.e., greater than or equal to 10%, 15%, or 20% shorter), but not greater or more than 50% shorter, than a wild type or control plant, and/or (ii) a stem or stalk diameter that is that is at least 5%, at least 10%, or at least 15% greater, but not more than 30%, 35%, or 40% greater, than a wild type or control plant. For clarity, the phrases "at least 20% shorter" and "greater than or equal to 20% shorter" would exclude, for example, 10% shorter. Likewise for clarity, the phrases "not greater than 50% shorter", "no more than 50% shorter" and "not more than 50% shorter" would exclude 60% shorter; the phrase "at least 5% greater" would exclude 2% greater; and the phrases "not more than 30% greater" and "no more than 30% greater" would exclude 40% greater.

According to embodiments of the present disclosure, modified corn plants are provided that comprise a height between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 45%, or between 30% and 45% less than the height of a wild-type or control plant, and/or a stem or stalk diameter that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, between 50% and 75%, between 8% and 20%, or between 8% and 15% greater than the stem or stalk diameter of the wild-type or control plant.

As used herein, "internode length" refers to the distance between two consecutive internodes on the stem of a plant. According to embodiments of the present disclosure, modified corn plants are provided that comprise an average internode length (or a minus-2 internode length and/or minus-4 internode length relative to the position of the ear) that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the same or average internode length of a wild-type or control plant. The "minus-2 internode" of a corn plant refers to the second internode below the ear of the plant, and the "minus-4 internode" of a corn plant refers to the fourth internode below the ear of the plant According to many embodiments, modified corn plants are provided that have an average internode length (or a minus-2 internode length and/or minus-4 internode length relative to the position of the ear) that is between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 50%, or between 30% and 45% less than the same or average internode length of a wild-type or control plant.

According to embodiments of the present disclosure, modified corn plants are provided that comprise an ear weight (individually or on average) that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the ear weight of a wild-type or control plant. A modified corn plant provided herein may comprise an ear weight that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 25% and 75%, between 25% and 50%, or between 50% and 75% greater than the ear weight of a wild-type or control plant.

According to embodiments of the present disclosure, modified corn plants are provided that have a harvest index of at least 0.57, at least 0.58, at least 0.59, at least 0.60, at least 0.61, at least 0.62, at least 0.63, at least 0.64, or at least 0.65 (or greater). A modified corn plant may comprise a harvest index of between 0.57 and 0.65, between 0.57 and 0.64, between 0.57 and 0.63, between 0.57 and 0.62, between 0.57 and 0.61, between 0.57 and 0.60, between 0.57 and 0.59, between 0.57 and 0.58, between 0.58 and 0.65, between 0.59 and 0.65, or between 0.60 and 0.65. A modified corn plant may have a harvest index that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, or at least 50% greater than the harvest index of a wild-type or control plant. A modified corn plant may have a harvest index that is between 1% and 45%, between 1% and 40%, between 1% and 35%, between 1% and 30%, between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 30%, or between 5% and 40% greater than the harvest index of a wild-type or control plant.

According to embodiments of the present disclosure, modified corn plants are provided that have an increase in harvestable yield of at least 1 bushel per acre, at least 2 bushels per acre, at least 3 bushels per acre, at least 4 bushels per acre, at least 5 bushels per acre, at least 6 bushels per acre, at least 7 bushels per acre, at least 8 bushels per acre, at least 9 bushels per acre, or at least bushels per acre, relative to a wild-type or control plant. A modified corn plant may have an increase in harvestable yield between 1 and 10, between 1 and 8, between 2 and 8, between 2 and 6, between 2 and 5, between 2.5 and 4.5, or between 3 and 4 bushels per acre. A modified corn plant may have an increase in harvestable yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, or at least 25% greater than the harvestable yield of a wild-type or control plant. A modified corn plant may have a harvestable yield that is between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 25%, between 2% and 10%, between 2% and 9%, between 2% and 8%, between 2% and 7%, between 2% and 6%, between 2% and 5%, or between 2% and 4% greater than the harvestable yield of a wild-type or control plant.

According to embodiments of the present disclosure, a modified corn plant is provided that has a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less or lower than a wild-type or control plant. A modified corn plant may have a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, or between 50% and 75% less or lower than a wild-type or control plant. Further provided are populations of corn plants having increased lodging resistance and a reduced lodging frequency. Populations of modified corn plants are provided having a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less or lower than a population of wild-type or control plants. A population of modified corn plants may comprise a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, or between 50% and 75% less or lower than a population of wild-type or control plants, which may be expressed as an average over a specified number of plants or crop area of equal density.

According to embodiments of the present disclosure, modified corn plants are provided having a significantly reduced or decreased plant height (e.g., 2000 mm or less) and a significantly increased stem diameter (e.g., 18 mm or more), relative to a wild-type or control plant. According to these embodiments, the decrease or reduction in plant height and increase in stem diameter may be within any of the height, diameter or percentage ranges recited herein. Such modified corn plants having a reduced plant height and increased stem diameter relative to a wild-type or control plant may be transformed with a transcribable DNA sequence encoding a non-coding RNA molecule that targets at least one GA20 oxidase gene and/or at least one GA3 oxidase gene for suppression. Modified corn plants having a significantly reduced plant height and/or a significantly increased stem diameter relative to a wild-type or control plant may further have at least one ear that is substantially free of male reproductive tissues or structures and/or other off-types. Modified corn plants having a significantly reduced plant height and/or an increased stem diameter relative to a wild-type or control plant may have reduced activity of one or more GA20 oxidase and/or GA3 oxidase gene(s) in one or more tissue(s) of the plant, such as one or more vascular and/or leaf tissue(s) of the plant, relative to the same tissue(s) of the wild-type or control plant. According to many embodiments, modified corn plants may comprise at least one polynucleotide or transcribable DNA sequence encoding a non-coding RNA molecule operably linked to a promoter, which may be a constitutive, tissue-specific or tissue-preferred promoter, wherein the non-coding RNA molecule targets at least one GA20 oxidase and/or GA3 oxidase gene(s) for suppression as provided herein. The non-coding RNA molecule may be a miRNA, siRNA, or miRNA or siRNA precursor molecule. According to some embodiments, modified corn plants having a significantly reduced plant height and/or an increased stem diameter relative to a wild-type or control plant may further have an increased harvest index and/or increased lodging resistance relative to the wild-type or control plant.

According to embodiments of the present invention, modified corn plants are provided having a reduced gibberellin content (in active form) in at least the stem and internode tissue(s), such as the stem, internode, leaf and/or vascular tissue(s), as compared to the same tissue(s) of wild-type or control plants. According to many embodiments, modified corn plants are provided having a significantly reduced plant height and/or a significantly increased stem diameter relative to wild-type or control plants, wherein the modified corn plants further have significantly reduced or decreased level(s) of active gibberellins or active GAs (e.g., one or more of GA1, GA3, GA4, and/or GA7) in one or more stem, internode, leaf and/or vascular tissue(s), relative to the same tissue(s) of the wild-type or control plants. For example, the level of one or more active GAs in the stem, internode, leaf and/or vascular tissue(s) of a modified corn plant may be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% less or lower than in the same tissue(s) of a wild-type or control corn plant.

According to some embodiments, a modified corn plant may comprise an active gibberellin (GA) level(s) (e.g., one or more of GA1, GA3, GA4, and/or GA7) in one or more stem, internode, leaf and/or vascular tissue(s) that is between 5% and 50%, between 10% and 100%, between 20% and 100%, between 30% and 100%, between 40% and 100%, between 50% and 100%, between 60% and 100%, between 70% and 100%, between 80% and 100%, between 80% and 90%, between 10% and 90%, between 10% and 80%, between 10% and 70%, between 10% and 60%, between 10% and 50%, between 10% and 40%, between 10% and 30%, between 10% and 20%, between 50% and 100%, between 20% and 90%, between 20% and 80%, between 20% and 70%, between 20% and 60%, between 20% and 50%, between 20% and 40%, between 20% and 40%, between 20% and 30%, between 30% and 90%, between 30% and 80%, between 30% and 70%, between 30% and 60%, between 30% and 50%, between 30% and 40%, between 40% and 90% between 40% and 80%, between 40% and 70%, between 40% and 60%, between 40% and 50%, between 50% and 90%, between 50% and 80%, between 50% and 70%, between 50% and 60%, between 60% and 90%, between 60% and 80%, between 60% and 70%, between 70% and 90%, or between 70% and 80% less or (or lower) than in the same tissue(s) of a wild-type or control corn plant. A modified corn plant having a reduced active gibberellin (GA) level(s) in one or more stem, internode, leaf and/or vascular tissue(s) may further be substantially free of off-types, such as male reproductive tissues or structures and/or other off-types in at least one ear of a modified corn plant.

According to embodiments of the present disclosure, modified corn plants are provided having a significantly reduced or eliminated expression level of one or more GA3 oxidase and/or GA20 oxidase gene transcript(s) and/or protein(s) in one or more tissue(s), such as one or more stem, internode, leaf and/or vascular tissue(s), of the modified plants, as compared to the same tissue(s) of wild-type or control plants. According to many embodiments, a modified corn plant is provided comprising a significantly reduced plant height and/or a significantly increased stem diameter relative to wild-type or control plants, wherein the modified corn plant has a significantly reduced or eliminated expression level of one or more GA20 oxidase and/or GA3 oxidase gene transcript(s) and/or protein(s) in one or more tissues, such as one or more stem, internode, leaf and/or vascular tissue(s), of the modified plant, as compared to the same tissue(s) of a wild-type or control corn plant. For example, a modified corn plant has a significantly reduced or eliminated expression level of a GA20 oxidase_3 and/or GA20 oxidase_5 gene transcript(s) and/or protein(s), in the whole modified plant, or in one or more stem, internode, leaf and/or vascular tissue(s) of the modified plant, as compared to the same tissue(s) of a wild-type or control plant. For example, the level of one or more GA20 oxidase gene transcript(s) and/or protein(s), or one or more GA oxidase (or GA oxidase-like) gene transcript(s) and/or protein(s), in one or more stem, internode, leaf and/or vascular tissue(s) of a modified corn plant may be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% less or lower than in the same tissue(s) of a wild-type or control corn plant.

According to some embodiments, a modified corn plant may comprise level(s) of one or more GA20 oxidase gene transcript(s) and/or protein(s), or one or more GA oxidase (or GA oxidase-like) gene transcript(s) and/or protein(s), in the whole plant, or in one or more stem, internode, leaf and/or vascular tissue(s), that is between 5% and 50%, between 10% and 100%, between 20% and 100%, between 30% and 100%, between 40% and 100%, between 50% and 100%, between 60% and 100%, between 70% and 100%, between 80% and 100%, between 80% and 90%, between 10% and 90%, between 10% and 80%, between 10% and 70%, between 10% and 60%, between 10% and 50%, between 10% and 40%, between 10% and 30%, between 10% and 20%, between 50% and 100%, between 20% and 90%, between 20% and 80%, between 20% and 70%, between 20% and 60%, between 20% and 50%, between 20% and 40%, between 20% and 40%, between 20% and 30%, between 30% and 90%, between 30% and 80%, between 30% and 70%, between 30% and 60%, between 30% and 50%, between 30% and 40%, between 40% and 90% between 40% and 80%, between 40% and 70%, between 40% and 60%, between 40% and 50%, between 50% and 90%, between 50% and 80%, between 50% and 70%, between 50% and 60%, between 60% and 90%, between 60% and 80%, between 60% and 70%, between 70% and 90%, or between 70% and 80% less or lower than in the same tissue(s) of a wild-type or control corn plant. A modified corn plant having a reduced or eliminated expression level of at least one GA20 oxidase gene(s) in one or more tissue(s), may also be substantially free of off-types, such as male reproductive tissues or structures and/or other off-types in at least one ear of the modified corn plant.

Methods and techniques are provided for screening for, and/or identifying, cells or plants, etc., for the presence of targeted edits or transgenes, and selecting cells or plants comprising targeted edits or transgenes, which may be based on one or more phenotypes or traits, or on the presence or absence of a molecular marker or polynucleotide or protein sequence in the cells or plants. Nucleic acids can be isolated and detected using techniques known in the art. For example, nucleic acids can be isolated and detected using, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis. Any method known in the art may be used to screen for, and/or identify, cells, plants, etc., having a transgene or genome edit in its genome, which may be based on any suitable form of visual observation, selection, molecular technique, etc.

In some embodiments, methods are provided for detecting recombinant nucleic acids and/or polypeptides in plant cells. For example, nucleic acids may be detected using hybridization probes or through production of amplicons using PCR with primers as known in the art. Hybridization between nucleic acids is discussed in Sambrook et al. (1989, Molecular Cloning: A Laboratory Manual, 2nd Ed., Cold Spring Harbor Laboratory Press, Cold Spring Harbor, NY). Polypeptides can be detected using antibodies. Techniques for detecting polypeptides using antibodies include enzyme linked immunosorbent assays (ELISAs), Western blots, immunoprecipitations, immunofluorescence, and the like. An antibody provided herein may be a polyclonal antibody or a monoclonal antibody. An antibody having specific binding affinity for a polypeptide provided herein can be generated using methods known in the art. An antibody or hybridization probe may be attached to a solid support, such as a tube, plate or well, using methods known in the art.

Detection (e.g., of an amplification product, of a hybridization complex, of a polypeptide) can be accomplished using detectable labels that may be attached or associated with a hybridization probe or antibody. The term "label" is intended to encompass the use of direct labels as well as indirect labels. Detectable labels include enzymes, prosthetic groups, fluorescent materials, luminescent materials, bioluminescent materials, and radioactive materials.

The screening and selection of modified, edited plants or plant cells can be through any methodologies known to those skilled in the art of molecular biology. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina®, PacBio®, Ion Torrent™, etc.) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known in the art.

The following non-limiting embodiments are envisioned:

1. A modified corn plant, or plant part thereof, comprising a mutant allele of the endogenous GA20 oxidase_3 locus, wherein the mutant allele comprises a DNA segment inserted into the endogenous GA20 oxidase_3 locus, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_3 locus produces a RNA transcript comprising the antisense RNA sequence.

2. The modified corn plant, or plant part thereof, of embodiment 1, wherein the mutant allele of the endogenous GA20 oxidase_3 locus suppresses the expression of a wild-type allele of the endogenous GA20 oxidase_3 locus, a wild-type allele of the endogenous GA20 oxidase_5 locus, or both.

3. The modified corn plant, or plant part thereof, of embodiment 1, wherein the RNA transcript further comprises one or more sequence elements of the endogenous GA20 oxidase_3 locus selected from the group consisting of 5' UTR, $1^{st}$ exon, $1^{st}$ intron, $2^{nd}$ exon, $2^{nd}$ intron, $3^{rd}$ exon, 3' UTR, and any portion thereof.

4. The modified corn plant, or plant part thereof, of embodiment 1, wherein the DNA segment comprises a nucleotide sequence originating from the endogenous GA20 oxidase_3 locus.

5. The modified corn plant, or plant part thereof, of embodiment 4, wherein the DNA segment corresponds to an inverted genomic fragment of the endogenous GA20 oxidase_3 locus.

6. The modified corn plant, or plant part thereof, of embodiment 1, wherein the DNA segment comprises a nucleotide sequence originating from the endogenous GA20 oxidase_5 locus.

7. The modified corn plant, or plant part thereof, of embodiment 6, wherein the DNA segment corresponds to an inverted genomic fragment of the endogenous GA20 oxidase_5 locus.

8. The modified corn plant, or plant part thereof, of embodiment 1, wherein at least a portion of the antisense RNA sequence is at least 70%, at least 75%, at least 80%, at least 85%, at least 90%, at least 95%, at least 96%, at least 97%, at least 98%, at least 99%, or 100% complementary to a corresponding endogenous sequence of the RNA transcript.

9. The modified corn plant, or plant part thereof, of embodiment 8, wherein the corresponding endogenous sequence of the RNA transcript is at least 85%, at least 90%, at least 95%, at least 96%, at least 97%, at least 98%, at least 99%, or 100% identical to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7.

10. The modified corn plant, or plant part thereof, of embodiment 8 or 9, wherein the antisense RNA sequence hybridizes to the corresponding endogenous sequence of the RNA transcript.

11. The modified corn plant, or plant part thereof, of any one of embodiments 8-10, wherein the DNA segment is inserted near or adjacent to a corresponding endogenous DNA segment of the endogenous GA20 oxidase_3 locus.

12. The modified corn plant, or plant part thereof, of embodiment 10, wherein the antisense RNA sequence encoded by the inserted DNA segment hybridizes to a corresponding endogenous sequence of the RNA transcript encoded by the corresponding endogenous DNA segment.

13. The modified corn plant, or plant part thereof, of embodiment 11 or 12, wherein the antisense RNA sequence forms a stem-loop structure with the corresponding endogenous sequence of the RNA transcript.

14. The modified corn plant, or plant part thereof, of embodiment 10, wherein the inserted DNA segment and the corresponding endogenous DNA segment of the mutant allele are separated by an intervening DNA sequence.

15. The modified corn plant, or plant part thereof, of embodiment 12, wherein the intervening DNA sequence has a length of at least 1, 2, 3, 4, 5, 6, 7, 8, 9, 10, 11, 12, 13, 14, 15, 20, 25, 30, 40, 50, 75, 100, 150, 200, 250, 300, 400, 500, 750, 1000, 1500, 2000, 3000, or 4000 consecutive nucleotides.

16. The modified corn plant, or plant part thereof, of embodiment 12, wherein the DNA segment and the corresponding endogenous DNA segment are separated by an intervening sequence of at most 1, 2, 3, 4, 5, 6, 7, 8, 9, 10, 11, 12, 13, 14, 15, 20, 25, 30, 40, 50, 75, 100, 150, 200, 250, 300, 400, 500, 750, 1000, 1500, 2000, 3000, or 4000 consecutive nucleotides.

17. The modified corn plant, or plant part thereof, of any one of embodiments 14-16, wherein the intervening DNA sequence encodes an intervening RNA sequence between the antisense RNA sequence and the corresponding endogenous sequence of the RNA transcript.
18. The modified corn plant, or plant part thereof, of embodiment 17, wherein the RNA transcript forms a stem-loop structure with the intervening RNA sequence forming the loop portion of the stem-loop structure.
19. The modified corn plant, or plant part thereof, of embodiment 18, wherein the stem-loop secondary structure contains a near-perfect-complement stem with mismatches.
20. The modified corn plant, or plant part thereof, of embodiment 18, wherein the stem-loop secondary structure contains a perfect-complement stem with no mismatch.
21. The modified corn plant, or plant part thereof, of any one of embodiments 14-20, wherein the intervening DNA sequence comprises a native sequence of the endogenous GA20 oxidase_3 locus.
22. The modified corn plant, or plant part thereof, of any one of embodiments 14-20, wherein the intervening DNA sequence comprises an exogenous sequence inserted into the endogenous GA20 oxidase_3 locus.
23. The modified corn plant, or plant part thereof, of any one of embodiments 14-20, wherein the intervening sequence contains an intron sequence.
24. The modified corn plant, or plant part thereof, of any one of embodiments 14-20, wherein the intervening sequence does not contain an intron sequence.
25. The modified corn plant, or plant part thereof, of embodiment 10, wherein the inserted DNA segment is located upstream of the corresponding endogenous DNA segment.
26. The modified corn plant, or plant part thereof, of embodiment 10, wherein the inserted DNA segment is located downstream of the corresponding endogenous DNA segment.
27. The modified corn plant, or plant part thereof, of embodiment 8, wherein the DNA segment is inserted within a region selected from the group consisting of 5' untranslated region (UTR), $1^{st}$ exon, $1^{st}$ intron, $2^{nd}$ exon, $2^{nd}$ intron, $3^{rd}$ exon and 3' UTR of the endogenous GA20 oxidase_3 locus, and a combination thereof.
28. The modified corn plant, or plant part thereof, of embodiment 8, wherein the DNA segment is inserted at a genomic site recognized by a targeted editing technique to create a double-stranded break (DSB).
29. The modified corn plant, or plant part thereof, of embodiment 8, wherein the mutant allele further comprises a deletion of at least one portion of the endogenous GA20 oxidase_3 locus.
30. The modified corn plant, or plant part thereof, of embodiment 8, wherein the sense strand of the DNA segment comprises a sequence at least 70%, at least 75%, at least 80%, at least 85%, at least 90%, at least 95%, at least 96%, at least 97%, at least 98%, at least 99%, or 100% complementary to an exon sequence of the endogenous GA20 oxidase_3 or GA20 oxidase_5 locus.
31. The modified corn plant, or plant part thereof, of embodiment 8, wherein the sense strand of the DNA segment comprises a sequence at least 70%, at least 75%, at least 80%, at least 85%, at least 90%, at least 95%, at least 96%, at least 97%, at least 98%, at least 99%, or 100% complementary to an untranslated region (UTR) sequence of the endogenous GA20 oxidase_3 or GA20 oxidase_5 locus.
32. The modified corn plant, or plant part thereof, of embodiment 8, wherein the sense strand of the DNA segment comprises a sequence at least 70%, at least 75%, at least 80%, at least 85%, at least 90%, at least 95%, at least 96%, at least 97%, at least 98%, at least 99%, or 100% complementary to an exon sequence and an intron sequence of the endogenous GA20 oxidase_3 or GA20 oxidase_5 locus, the exon sequence and the intron sequence being contiguous within the endogenous locus.
33. The modified corn plant, or plant part thereof, of embodiment 8, wherein the DNA segment comprises a sequence having at least at least 70%, at least 75%, at least 80%, at least 85%, at least 90%, at least 95%, at least 96%, at least 97%, at least 98%, at least 99%, or 100% identity to one or more of SEQ ID Nos: 13, 14, 26, 28, 30, 32 and 36.
34. The modified corn plant, or plant part thereof, of any one of embodiments 1 to 21, wherein the corn plant is homozygous for the mutant allele at the endogenous GA20 oxidase_3 locus.
35. The modified corn plant, or plant part thereof, of any one of embodiments 1 to 21, wherein the corn plant is heterozygous for the mutant allele at the endogenous GA20 oxidase_3 locus.
36. The modified corn plant, or plant part thereof, of any one of embodiments 1 to 21, wherein the DNA segment has a length of at least 15, 16, 17, 18, 19, 20, 21, 22, 23, 24, 25, 30, 35, 40, 45, 50, 75, 100, 125, 150, 175, 200, 250, 300, 400, 500, 750, or 1000 nucleotides.
37. The modified corn plant, or plant part thereof, of any one of embodiments 1 to 21, wherein the DNA segment has a length of at most 25, 50, 100, 150, 200, 250, 300, 400, 500, 750, or 1000 nucleotides.
38. The modified corn plant, or plant part thereof, of any one of embodiments 1 to 37, wherein the modified corn plant has a shorter plant height and/or improved lodging resistance relative to an unmodified control plant.
39. The modified corn plant, or plant part thereof, of any one of embodiments 1 to 37, wherein the modified corn plant exhibits an at least 2.5%, at least 5%, at least 7.5%, at least 10%, at least 15%, at least 20%, at least 25%, at least 30%, at least 35%, or at least 40% reduction in plant height at maturity relative to an unmodified control plant.
40. The modified corn plant, or plant part thereof, of embodiment 39, wherein the plant height reduction is between 5% and 40%, between 10% and 40%, between 15% and 40%, between 20% and 40%, between 30% and 40%, between 10% and 30%, between 15% and 30%, between 20% and 30%, between 5% and 30%, between 7.5% and 25%, between 10 and 20%, 5% and 7.5%, between 7.5% and 10%, between 10 and 15%, or between 15% to 20%.
41. The modified corn plant, or plant part thereof, of any one of embodiments 1 to 37, wherein the stalk or stem diameter of the modified corn plant at one or more stem internodes is at least 5%, at least 10%, at least 15%, at least 20%, at least 25%, at least 30%, at least 35%, or at least 40% greater than the stalk or stem diameter at the same one or more internodes of an unmodified control plant.
42. The modified corn plant, or plant part thereof, of any one of embodiments 1 to 37, wherein the stalk or stem diameter of the modified corn plant at one or more of the first, second, third, and/or fourth internode below the ear is at least 5%, at least 10%, at least 15%, at least 20%, at least 25%, at least 30%, at least 35%, or at least 40% greater than the same internode of an unmodified control plant.

43. The modified corn plant, or plant part thereof, of any one of embodiments 1 to 37, wherein the level of one or more active GAs in at least one internode tissue of the stem or stalk of the modified corn plant is at least 5%, at least 10%, at least 15%, at least 20%, at least 25%, at least 30%, at least 35%, or at least 40% lower than the same internode tissue of an unmodified control plant.

44. The modified corn plant, or plant part thereof, of any one of embodiments 1 to 37, wherein the level of one or more active GAs in at least one internode tissue of the stem or stalk of the modified corn plant is lower than the same internode tissue of an unmodified control plant.

45. The modified corn plant, or plant part thereof, of any one of embodiments 1 to 37, wherein the modified corn plant does not have any significant off-types in at least one female organ or ear.

46. The modified corn plant, or plant part thereof, of any one of embodiments 1 to 37, wherein the modified corn plant exhibits essentially no reproductive abnormality.

47. A method for producing a mutant allele of the endogenous GA20 oxidase_3 locus, the method comprising:
    a. generating a double-stranded break (DSB) in the endogenous GA20 oxidase_3 locus in a corn cell using a targeted editing technique;
    b. inserting at the DSB a DNA segment using a targeted editing technique, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_3 locus produces a RNA transcript comprising the antisense RNA sequence.

48. The method of embodiment 27, wherein the targeted editing technique comprises the use of at least one site-specific nuclease.

49. The method of embodiment 28, wherein the at least one site-specific nuclease is selected from the group consisting of a zinc-finger nuclease, a meganuclease, an RNA-guided nuclease, a TALE-nuclease, a recombinase, a transposase, and any combination thereof.

50. The method of embodiment 28, wherein the at least one site-specific nuclease is a RNA-guided nuclease selected from the group consisting of a Cas9 nuclease or a variant thereof, and a Cpf1 nuclease or a variant thereof.

51. The method of embodiment 27, wherein the DNA segment originates from the endogenous GA20 oxidase_3 locus or the endogenous GA20 oxidase_5 locus.

52. The method of embodiment 27, wherein the DNA segment is provided in a donor template.

53. The method of embodiment 27, wherein the method further comprises regenerating or developing a corn plant from the corn cell.

54. The method of embodiment 27, wherein the mutant allele of the endogenous GA20 oxidase_3 locus is capable of suppressing the expression of a wild-type allele of the endogenous GA20 oxidase_3 locus, a wild-type allele of the endogenous GA20 oxidase 5 locus, or both.

55. The method of embodiment 27, wherein at least a portion of the antisense RNA sequence is at least 70%, at least 75%, at least 80%, at least 85%, at least 90%, at least 95%, at least 96%, at least 97%, at least 98%, at least 99%, or 100% complementary to a corresponding endogenous sequence of the RNA transcript.

56. The method of embodiment 55, wherein the antisense RNA sequence hybridizes to the corresponding endogenous sequence of the RNA transcript.

57. The method of any one of embodiments 47 to 56, wherein the DNA segment is inserted near or adjacent to a corresponding endogenous DNA segment of the endogenous GA20 oxidase_3 locus.

58. The method of embodiment 33, wherein the antisense RNA sequence encoded by the inserted DNA segment hybridizes to a corresponding endogenous sequence of the RNA transcript encoded by the corresponding endogenous DNA segment.

59. The method of embodiment 33, wherein the antisense RNA sequence forms a stem-loop structure with the corresponding endogenous sequence of the RNA transcript.

60. The method of embodiment 33, wherein the inserted DNA segment and the corresponding endogenous DNA segment of the mutant allele are separated by an intervening DNA sequence.

61. The method of embodiment 36, wherein the intervening DNA sequence has a length of at least 1, 2, 3, 4, 5, 6, 7, 8, 9, 10, 11, 12, 13, 14, 15, 20, 25, 30, 40, 50, 75, 100, 150, 200, 250, 300, 400, 500, 750, 1000, 1500, 2000, 3000, or 4000 consecutive nucleotides.

62. The method of embodiment 36, wherein the DNA segment and the corresponding endogenous sequence are separated by an intervening sequence of at most 1, 2, 3, 4, 5, 6, 7, 8, 9, 10, 11, 12, 13, 14, 15, 20, 25, 30, 40, 50, 75, 100, 150, 200, 250, 300, 400, 500, 750, 1000, 1500, 2000, 3000, or 4000 consecutive nucleotides.

63. The method of any one of embodiments 60-62, wherein the intervening DNA sequence encodes an intervening RNA sequence between the antisense RNA sequence and the corresponding endogenous sequence of the RNA transcript.

64. The method of embodiment 63, wherein the RNA transcript forms a stem-loop structure with the intervening RNA sequence forming the loop portion of the stem-loop structure.

65. The method of any one of embodiments 60-64, wherein the intervening DNA sequence comprises a native sequence of the endogenous GA20 oxidase_3 locus.

66. The method of any one of embodiments 60-64, wherein the intervening DNA sequence comprises an exogenous sequence inserted into the endogenous GA20 oxidase_3 locus.

67. The method of embodiment 33, wherein the inserted DNA segment is located upstream of the corresponding endogenous DNA segment.

68. The method of embodiment 33, wherein the inserted DNA segment is located downstream of the corresponding endogenous DNA segment.

69. The method of embodiment 33, wherein the DNA segment is inserted within a region selected from the group consisting of 5' untranslated region (UTR), $1^{st}$ exon, $1^{st}$ intron, $2^{nd}$ exon, $2^{nd}$ intron, $3^{rd}$ exon and 3' UTR of the endogenous GA20 oxidase_3 locus, and a combination thereof.

70. The method of embodiment 33, wherein the sense strand of the DNA segment comprises (i) a reverse complement sequence of an exon sequence of the endogenous GA20 oxidase_3 or GA20 oxidase_5 locus, or (ii) a sequence that is at least 70%, at least 75%, at least 80%, at least 85%, at least 90%, at least 95%, at least 96%, at least 97%, at least 98%, at least 99%, or 100% identical to the reverse complement sequence.

71. The method of embodiment 33, wherein the sense strand of the DNA segment comprises (i) a reverse complement sequence of an untranslated region (UTR) sequence of the endogenous GA20 oxidase 3 or GA20 oxidase_5 locus, or (ii) a sequence that is at least 70%, at least 75%, at least 80%, at least 85%, at least 90%, at least 95%, at least 96%, at least 97%, at least 98%, at least 99%, or 100% identical to the reverse complement sequence.

72. The method of embodiment 33, wherein the sense strand of the DNA segment comprises (i) a reverse complement sequence of an exon sequence and an intron sequence of the endogenous GA20 oxidase_3 or GA20 oxidase_5 locus, and wherein the exon sequence and the intron sequence are contiguous within the endogenous locus, or (ii) a sequence that is at least 70%, at least 75%, at least 80%, at least 85%, at least 90%, at least 95%, at least 96%, at least 97%, at least 98%, at least 99%, or 100% identical to the reverse complement sequence.

73. The method of embodiment 33, wherein the DNA segment comprises a sequence having at least at least 70%, at least 75%, at least 80%, at least 85%, at least 90%, at least 95%, at least 97%, or 100% identity to one or more of SEQ ID Nos: 13, 14, 26, 28, 30, 32 and 36.

74. The method of any one of embodiments 33 to 43, wherein the DNA segment has a length of at least 15, 16, 17, 18, 19, 20, 21, 22, 23, 24, 25, 30, 35, 40, 45, 50, 75, 100, 125, 150, 175, 200, 250, 300, 400, 500, 750, or 1000 nucleotides.

75. The method of any one of embodiments 33 to 43, wherein the DNA segment has a length of at most 25, 50, 100, 150, 200, 250, 300, 400, 500, 750, or 1000 nucleotides.

76. A modified corn plant, or plant part thereof, comprising a mutant allele of the endogenous GA20 oxidase_5 locus, wherein the mutant allele comprises a DNA segment inserted into the endogenous GA20 oxidase_5 locus, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_5 locus produces a RNA transcript comprising the antisense RNA sequence.

77. The modified corn plant, or plant part thereof, of embodiment 45, wherein the mutant allele of the endogenous GA20 oxidase_5 locus suppresses the expression of a wild-type allele of the endogenous GA20 oxidase_3 locus, a wild-type allele of the endogenous GA20 oxidase_5 locus, or both.

78. The modified corn plant, or plant part thereof, of embodiment 45, wherein the RNA transcript further comprises one or more sequence elements of the endogenous GA20 oxidase_5 locus selected from the group consisting of 5' UTR, $1^{st}$ exon, $1^{st}$ intron, $2^{nd}$ exon, $2^{nd}$ intron, $3^{rd}$ exon, 3' UTR, and any portion thereof.

79. The modified corn plant, or plant part thereof, of embodiment 45, wherein the DNA segment comprises a nucleotide sequence originating from the endogenous GA20 oxidase_3 locus.

80. The modified corn plant, or plant part thereof, of embodiment 48, wherein the DNA segment corresponds to an inverted genomic fragment of the endogenous GA20 oxidase_3 locus.

81. The modified corn plant, or plant part thereof, of embodiment 45, wherein the DNA segment comprises a nucleotide sequence originating from the endogenous GA20 oxidase_5 locus.

82. The modified corn plant, or plant part thereof, of embodiment 50, wherein the DNA segment corresponds to an inverted genomic fragment of the endogenous GA20 oxidase_5 locus.

83. The modified corn plant, or plant part thereof, of embodiment 45, wherein at least a portion of the antisense RNA sequence is at least 70%, at least 75%, at least 80%, at least 85%, at least 90%, at least 95%, at least 96%, at least 97%, at least 98%, at least 99%, or 100% complementary to a corresponding endogenous sequence of the RNA transcript.

84. The modified corn plant, or plant part thereof, of embodiment 52, wherein the corresponding endogenous sequence of the RNA transcript is at least 85%, at least 90%, at least 95%, at least 96%, at least 97%, at least 98%, at least 99%, or 100% identical to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7.

85. The modified corn plant, or plant part thereof, of embodiment 52 or 53, wherein the antisense RNA sequence hybridizes to the corresponding endogenous sequence of the RNA transcript.

86. The modified corn plant, or plant part thereof, of any one of embodiments 83-85, wherein the DNA segment is inserted near or adjacent to a corresponding endogenous DNA segment of the endogenous GA20 oxidase_5 locus.

87. The modified corn plant, or plant part thereof, of embodiment 54, wherein the antisense RNA sequence encoded by the inserted DNA segment hybridizes to a corresponding endogenous sequence of the RNA transcript encoded by the corresponding endogenous DNA segment.

88. The modified corn plant, or plant part thereof, of embodiment 86 or 87, wherein the antisense RNA sequence forms a stem-loop structure with the corresponding endogenous sequence of the RNA transcript.

89. The modified corn plant, or plant part thereof, of embodiment 54, wherein the inserted DNA segment and the corresponding endogenous DNA segment of the mutant allele are separated by an intervening DNA sequence.

90. The modified corn plant, or plant part thereof, of embodiment 56, wherein the intervening DNA sequence has a length of at least 1, 2, 3, 4, 5, 6, 7, 8, 9, 10, 11, 12, 13, 14, 15, 20, 25, 30, 40, 50, 75, 100, 150, 200, 250, 300, 400, 500, 750, 1000, 1500, 2000, 3000, or 4000 consecutive nucleotides.

91. The modified corn plant, or plant part thereof, of embodiment 56, wherein the DNA segment and the corresponding endogenous DNA segment are separated by an intervening sequence of at most 1, 2, 3, 4, 5, 6, 7, 8, 9, 10, 11, 12, 13, 14, 15, 20, 25, 30, 40, 50, 75, 100, 150, 200, 250, 300, 400, 500, 750, 1000, 1500, 2000, 3000, or 4000 consecutive nucleotides.

92. The modified corn plant, or plant part thereof, of any one of embodiments 89-91, wherein the intervening DNA sequence encodes an intervening RNA sequence between the antisense RNA sequence and the corresponding endogenous sequence of the RNA transcript.

93. The modified corn plant, or plant part thereof, of embodiment 92, wherein the RNA transcript forms a stem-loop structure with the intervening RNA sequence forming the loop portion of the stem-loop structure.

94. The modified corn plant, or plant part thereof, of embodiment 93, wherein the stem-loop secondary structure contains a near-perfect-complement stem with mismatches.

95. The modified corn plant, or plant part thereof, of embodiment 93, wherein the stem-loop secondary structure contains a perfect-complement stem with no mismatch.

96. The modified corn plant, or plant part thereof, of any one of embodiments 89-95, wherein the intervening DNA sequence comprises a native sequence of the endogenous GA20 oxidase_5 locus.

97. The modified corn plant, or plant part thereof, of any one of embodiments 89-95, wherein the intervening DNA sequence comprises an exogenous sequence inserted into the endogenous GA20 oxidase_5 locus.

98. The modified corn plant, or plant part thereof, of any one of embodiments 89-95, wherein the intervening sequence contains an intron sequence.

99. The modified corn plant, or plant part thereof, of any one of embodiments 89-95, wherein the intervening sequence does not contain an intron sequence.

100. The modified corn plant, or plant part thereof, of embodiment 54, wherein the inserted DNA segment is located upstream of the corresponding endogenous DNA segment.

101. The modified corn plant, or plant part thereof, of embodiment 54, wherein the inserted DNA segment is located downstream of the corresponding endogenous DNA segment.

102. The modified corn plant, or plant part thereof, of embodiment 52, wherein the DNA segment is inserted within a region selected from the group consisting of 5' untranslated region (UTR), $1^{st}$ exon, $1^{st}$ intron, $2^{nd}$ exon, $2^{nd}$ intron, $3^{rd}$ exon and 3' UTR of the endogenous GA20 oxidase_5 locus, and a combination thereof.

103. The modified corn plant, or plant part thereof, of embodiment 52, wherein the DNA segment is inserted at a genomic site recognized by a targeted editing technique to create a double-stranded break (DSB).

104. The modified corn plant, or plant part thereof, of embodiment 52, wherein the mutant allele further comprises a deletion of at least one portion of the endogenous GA20 oxidase_5 locus.

105. The modified corn plant, or plant part thereof, of embodiment 52, wherein the sense strand of the DNA segment comprises a sequence at least 70%, at least 75%, at least 80%, at least 85%, at least 90%, at least 95%, at least 96%, at least 97%, at least 98%, at least 99%, or 100% complementary to an exon sequence of the endogenous GA20 oxidase_3 or GA20 oxidase_5 locus.

106. The modified corn plant, or plant part thereof, of embodiment 52, wherein the sense strand of the DNA segment comprises a sequence at least 70%, at least 75%, at least 80%, at least 85%, at least 90%, at least 95%, at least 96%, at least 97%, at least 98%, at least 99%, or 100% complementary to an untranslated region (UTR) sequence of the endogenous GA20 oxidase_3 or GA20 oxidase_5 locus.

107. The modified corn plant, or plant part thereof, of embodiment 52, wherein the sense strand of the DNA segment comprises a sequence at least 70%, at least 75%, at least 80%, at least 85%, at least 90%, at least 95%, at least 96%, at least 97%, at least 98%, at least 99%, or 100% complementary to an exon sequence and an intron sequence of the endogenous GA20 oxidase_3 or GA20 oxidase_5 locus, the exon sequence and the intron sequence being contiguous within the endogenous locus.

108. The modified corn plant, or plant part thereof, of embodiment 52, wherein the DNA segment comprises a sequence having at least at least 70%, at least 75%, at least 80%, at least 85%, at least 90%, at least 95%, at least 96%, at least 97%, at least 98%, at least 99%, or 100% identity to one or more of SEQ ID Nos: 13, 14, 26, 28, 30, 32, and 36.

109. The modified corn plant, or plant part thereof, of embodiment 45, wherein the corn plant is homozygous for the mutant allele at the endogenous GA20 oxidase_5 locus.

110. The modified corn plant, or plant part thereof, of embodiment 45, wherein the corn plant is heterozygous for the mutant allele at the endogenous GA20 oxidase_5 locus.

111. The modified corn plant, or plant part thereof, of embodiment 52, wherein the DNA segment has a length of at least 15, 16, 17, 18, 19, 20, 21, 22, 23, 24, 25, 30, 35, 40, 45, 50, 75, 100, 125, 150, 175, 200, 250, 300, 400, 500, 750, or 1000 nucleotides.

112. The modified corn plant, or plant part thereof, of embodiment 52, wherein the DNA segment has a length of at most 25, 50, 100, 150, 200, 250, 300, 400, 500, 750, or 1000 nucleotides.

113. The modified corn plant, or plant part thereof, of any one of embodiments 76 to 112, wherein the modified corn plant has a shorter plant height and/or improved lodging resistance relative to an unmodified control plant.

114. The modified corn plant, or plant part thereof, of any one of embodiments 76 to 112, wherein the modified corn plant exhibits an at least 2.5%, at least 5%, at least 7.5%, at least 10%, at least 15%, at least 20%, at least 25%, at least 30%, at least 35%, or at least 40% reduction in plant height at maturity relative to an unmodified control plant.

115. The modified corn plant, or plant part thereof, of embodiment 114, wherein the plant height reduction is between 5% and 40%, between 10% and 40%, between 15% and 40%, between 20% and 40%, between 30% and 40%, between 10% and 30%, between 15% and 30%, between 20% and 30%, between 5% and 30%, between 7.5% and 25%, between 10 and 20%, 5% and 7.5%, between 7.5% and 10%, between 10 and 15%, or between 15% to 20%.
116. The modified corn plant, or plant part thereof, of any one of embodiments 76 to 112, wherein the stalk or stem diameter of the modified corn plant at one or more stem internodes is at least 5%, at least 10%, at least 15%, at least 20%, at least 25%, at least 30%, at least 35%, or at least 40% greater than the stalk or stem diameter at the same one or more internodes of an unmodified control plant.
117. The modified corn plant, or plant part thereof, of any one of embodiments 76 to 112, wherein the stalk or stem diameter of the modified corn plant at one or more of the first, second, third, and/or fourth internode below the ear is at least 5%, at least 10%, at least 15%, at least 20%, at least 25%, at least 30%, at least 35%, or at least 40% greater than the same internode of an unmodified control plant.
118. The modified corn plant, or plant part thereof, of any one of embodiments 76 to 112, wherein the level of one or more active GAs in at least one internode tissue of the stem or stalk of the modified corn plant is at least 5%, at least 10%, at least 15%, at least 20%, at least 25%, at least 30%, at least 35%, or at least 40% lower than the same internode tissue of an unmodified control plant.
119. The modified corn plant, or plant part thereof, of any one of embodiments 76 to 112, wherein the level of one or more active GAs in at least one internode tissue of the stem or stalk of the modified corn plant is lower than the same internode tissue of an unmodified control plant.
120. The modified corn plant, or plant part thereof, of any one of embodiments 76 to 112, wherein the modified corn plant does not have any significant off-types in at least one female organ or ear.
121. The modified corn plant, or plant part thereof, of any one of embodiments 76 to 112, wherein the modified corn plant exhibits essentially no reproductive abnormality.
122. A method for producing a mutant allele of the endogenous GA20 oxidase_5 locus, the method comprising:
   a. generating a double-stranded break (DSB) in the endogenous GA20 oxidase_5 locus in a corn cell using a targeted editing technique;
   b. inserting at the DSB a DNA segment using a targeted editing technique, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_5 locus produces a RNA transcript comprising the antisense RNA sequence.
123. The method of embodiment 71, wherein the targeted editing technique comprises the use of at least one site-specific nuclease.
124. The method of embodiment 72, wherein the at least one site-specific nuclease is selected from the group consisting of a zinc-finger nuclease, a meganuclease, an RNA-guided nuclease, a TALE-nuclease, a recombinase, a transposase, and any combination thereof.
125. The method of embodiment 72, wherein the at least one site-specific nuclease is a RNA-guided nuclease selected from the group consisting of a Cas9 nuclease or a variant thereof, and a Cpf1 nuclease or a variant thereof.
126. The method of embodiment 71, wherein the DNA segment originates from the endogenous GA20 oxidase_3 locus or the endogenous GA20 oxidase_5 locus.
127. The method of embodiment 71, wherein the DNA segment is provided in a donor template.
128. The method of embodiment 71, wherein the method further comprises regenerating or developing a corn plant from the corn cell.
129. The method of embodiment 71, wherein the mutant allele of the endogenous GA20 oxidase_5 locus is capable of suppressing the expression of a wild-type allele of the endogenous GA20 oxidase_3 locus, a wild-type allele of the endogenous GA20 oxidase_5 locus, or both.
130. The method of embodiment 71, wherein at least a portion of the antisense RNA sequence is at least 70%, at least 75%, at least 80%, at least 85%, at least 90%, at least 95%, at least 96%, at least 97%, at least 98%, at least 99%, or 100% complementary to a corresponding endogenous sequence of the RNA transcript.
131. The method of embodiment 130, wherein the antisense RNA sequence hybridizes to the corresponding endogenous sequence of the RNA transcript.
132. The method of any one of embodiments 122 to 131, wherein the DNA segment is inserted near or adjacent to a corresponding endogenous DNA segment of the endogenous GA20 oxidase_5 locus.
133. The method of embodiment 77, wherein the antisense RNA sequence encoded by the inserted DNA segment hybridizes to a corresponding endogenous sequence of the RNA transcript encoded by the corresponding endogenous DNA segment.
134. The method of embodiment 77, wherein the antisense RNA sequence forms a stem-loop structure with the corresponding endogenous sequence of the RNA transcript.
135. The method of embodiment 77, wherein the inserted DNA segment and the corresponding endogenous DNA segment of the mutant allele are separated by an intervening DNA sequence.
136. The method of embodiment 80, wherein the intervening DNA sequence has a length of at least 1, 2, 3, 4, 5, 6, 7, 8, 9, 10, 11, 12, 13, 14, 15, 20, 25, 30, 40, 50, 75, 100, 150, 200, 250, 300, 400, 500, 750, 1000, 1500, 2000, 3000, or 4000 consecutive nucleotides.
137. The method of embodiment 80, wherein the DNA segment and the corresponding endogenous sequence are separated by an intervening sequence of at most 1, 2, 3, 4, 5, 6, 7, 8, 9, 10, 11, 12, 13, 14, 15, 20, 25, 30, 40, 50, 75, 100, 150, 200, 250, 300, 400, 500, 750, 1000, 1500, 2000, 3000, or 4000 consecutive nucleotides.
138. The method of any one of embodiments 135-137, wherein the intervening DNA sequence encodes an intervening RNA sequence between the antisense RNA sequence and the corresponding endogenous sequence of the RNA transcript.

139. The method of embodiment 138, wherein the RNA transcript forms a stem-loop structure with the intervening RNA sequence forming the loop portion of the stem-loop structure.

140. The method of any one of embodiments 135-139, wherein the intervening DNA sequence comprises a native sequence of the endogenous GA20 oxidase_5 locus.

141. The method of any one of embodiments 135-139, wherein the intervening DNA sequence comprises an exogenous sequence inserted into the endogenous GA20 oxidase_5 locus.

142. The method of embodiment 77, wherein the inserted DNA segment is located upstream of the corresponding endogenous DNA segment.

143. The method of embodiment 77, wherein the inserted DNA segment is located downstream of the corresponding endogenous DNA segment.

144. The method of embodiment 77, wherein the DNA segment is inserted within a region selected from the group consisting of 5' untranslated region (UTR), $1^{st}$ exon, $1^{st}$ intron, $2^{nd}$ exon, $2^{nd}$ intron, $3^{rd}$ exon and 3' UTR of the endogenous GA20 oxidase_5 locus, and a combination thereof.

145. The method of embodiment 77, wherein the sense strand of the DNA segment comprises (i) a reverse complement sequence of an exon sequence of the endogenous GA20 oxidase_3 or GA20 oxidase_5 locus, or (ii) a sequence that is at least 70%, at least 75%, at least 80%, at least 85%, at least 90%, at least 95%, at least 96%, at least 97%, at least 98%, at least 99%, or 100% identical to the reverse complement sequence.

146. The method of embodiment 77, wherein the sense strand of the DNA segment comprises (i) a reverse complement sequence of an untranslated region (UTR) sequence of the endogenous GA20 oxidase_3 or GA20 oxidase_5 locus, or (ii) a sequence that is at least 70%, at least 75%, at least 80%, at least 85%, at least 90%, at least 95%, at least 96%, at least 97%, at least 98%, at least 99%, or 100% identical to the reverse complement sequence.

147. The method of embodiment 77, wherein the sense strand of the DNA segment comprises (i) a reverse complement sequence of an exon sequence and an intron sequence of the endogenous GA20 oxidase_3 or GA20 oxidase_5 locus, and wherein the exon sequence and the intron sequence are contiguous within the endogenous locus, or (ii) a sequence that is at least 70%, at least 75%, at least 80%, at least 85%, at least 90%, at least 95%, at least 96%, at least 97%, at least 98%, at least 99%, or 100% identical to the reverse complement sequence.

148. The method of embodiment 77, wherein the DNA segment comprises a sequence having at least at least 70%, at least 75%, at least 80%, at least 85%, at least 90%, at least 95%, at least 97%, or 100% identity to one or more of SEQ ID Nos: 13, 14, 26, 28, 30, 32, and 36.

149. The method of embodiment 77, wherein the DNA segment has a length of at least 15, 16, 17, 18, 19, 20, 21, 22, 23, 24, 25, 30, 35, 40, 45, 50, 75, 100, 125, 150, 175, 200, 250, 300, 400, 500, 750, or 1000 nucleotides.

150. The method of embodiment 77, wherein the DNA segment has a length of at most 25, 50, 100, 150, 200, 250, 300, 400, 500, 750, or 1000 nucleotides.

151. A method for generating a corn plant comprising:
(a) fertilizing at least one female corn plant with pollen from a male corn plant, wherein the at least one female corn plant and/or the male corn plant comprise(s) a mutant allele of an endogenous GA20 oxidase locus, wherein the mutant allele comprises a DNA segment inserted into the endogenous GA20 oxidase locus, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 or 5-7, and wherein the mutant allele of the endogenous GA20 oxidase locus produces a RNA transcript comprising the antisense RNA sequence; and
(b) obtaining at least one seed produced by said fertilizing of step (a).

152. The method of embodiment 151, wherein said method further comprises (c) growing said at least one seed obtained in step (b) to generate at least one progeny corn plant comprising said mutant allele.

153. The method of embodiment 151, wherein said at least one seed from step (b) is heterozygous for said mutant allele.

154. The method of embodiment 151, wherein said at least one seed from step (b) is homozygous for said mutant allele.

155. The method of any one of embodiments 151-154, wherein said female corn plant is homozygous for said mutant allele.

156. The method of any one of embodiments 151-154, wherein said female corn plant is heterozygous for said mutant allele.

157. The method of any one of embodiments 151-153, 155, or 156, wherein said male corn plant lacks said mutant allele.

158. The method of any one of embodiments 151-156, wherein said male corn plant is heterozygous for said mutant allele.

159. The method of any one of embodiments 151-156, wherein said male corn plant is homozygous for said mutant allele.

160. The method of any one of embodiments 152-157, wherein said at least one progeny corn plant has a shorter plant height and/or improved lodging resistance relative to an control plant lacking said mutant allele.

161. The method of any one of embodiments 152-157, wherein said at least one progeny corn plant has a shorter plant height and/or improved lodging resistance relative to said male corn plant.

162. The method of any one of embodiments 151-161, wherein said female corn plant is an inbred corn plant.

163. The method of any one of embodiments 151-161, wherein said female corn plant is a hybrid corn plant.

164. The method of any one of embodiments 151-163, wherein said male corn plant is an inbred corn plant.

165. The method of any one of embodiments 151-163, wherein said male corn plant is a hybrid corn plant.

166. The method of any one of embodiments 151-163, wherein said female corn plant is an elite corn plant.

167. The method of any one of embodiments 151-165, wherein said male corn plant is an elite corn plant.

168. The method of any one of embodiments 151-167, wherein said female corn plant is of a first inbred corn line or variety, and wherein said male corn plant is of a different, second inbred corn line or variety.

169. The method of any one of embodiments 151-168, wherein said female corn plant and said male corn plant are grown in a greenhouse or growth chamber.

170. The method of any one of embodiments 151-168, wherein said female corn plant and said male corn plant are grown outdoors.

171. The method of any one of embodiments 151-170, wherein said female corn plant has been detasseled.

172. The method of any one of embodiments 151-170, wherein said female corn plant is a cytoplasmically male sterile corn plant.

173. A modified corn plant part, corn cell, or corn tissue comprising a mutant allele of the endogenous GA20 oxidase_3 locus, wherein the mutant allele comprises a DNA segment inserted into the endogenous GA20 oxidase_3 locus, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_3 locus produces a RNA transcript comprising the antisense RNA sequence.

174. A modified corn plant part, corn cell, or corn tissue comprising a mutant allele of the endogenous GA20 oxidase_5 locus, wherein the mutant allele comprises a DNA segment inserted into the endogenous GA20 oxidase_5 locus, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_5 locus produces a RNA transcript comprising the antisense RNA sequence.

175. A method for producing a mutant allele of the endogenous GA20 oxidase_5 locus, the method comprising:
a. generating a first double-stranded break and a second double strand break in the endogenous GA20 oxidase_5 locus in a corn cell using a targeted editing technique;
b. inserting a DNA segment between the first double-stranded break and the second double-stranded break, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_5 locus produces a RNA transcript comprising the antisense RNA sequence.

176. A method for producing a mutant allele of the endogenous GA20 oxidase_3 locus, the method comprising:
a. generating a first double-stranded break and a second double strand break in the endogenous GA20 oxidase_3 locus in a corn cell using a targeted editing technique;
b. inserting a DNA segment between the first double-stranded break and the second double-stranded break, wherein the DNA segment encodes an antisense RNA sequence that is at least 70%, at least 75%, at least 80%, at least 85%, at least 90%, at least 95%, at least 96%, at least 97%, at least 98%, at least 99%, or 100% complementary to at least 20, at least 25, at least 30, at least 40, at least 50, at least 75, at least 100, at least 150, at least 200, at least 300, at least 400, at least 500, at least 750, or at least 1000 consecutive nucleotides of one or more of SEQ ID NOs: 1-3 and 5-7, and wherein the mutant allele of the endogenous GA20 oxidase_3 locus produces a RNA transcript comprising the antisense RNA sequence.

Having described the present disclosure in detail, it will be apparent that modifications, variations, and equivalent aspects are possible without departing from the spirit and scope of the present disclosure as described herein and in the appended claims. Furthermore, it should be appreciated that all examples in the present disclosure are provided as non-limiting examples.

EXAMPLES

Example 1. Creating Dominant Alleles by Genome Editing to Produce a Hairpin-Containing Transcript FIG. 1 provides illustrative examples for the production, through targeted gene editing, of a genomic modification of the Zm.GA20ox3 locus to encode a RNA transcript with an inverted sequence that can hybridize to a corresponding sequence of the RNA transcript to produce a stem-loop structure, to cause the suppression of one or both of the copies or alleles at the endogenous Zm.GA20ox3 and Zm.GA20ox5 loci. The Zm.GA20ox3 and Zm.GA20ox5 genes share a high level of nucleotide sequence similarity of their respective exon regions. Thus, a fragment of the Zm.GA20ox5 gene, sharing sufficient sequence identity or homology with a corresponding sequence of the Zm.GA20ox3 gene, inserted into a preselected site in the Zm.GA20ox3 gene in the reverse orientation near the corresponding Zm.GA20ox3 sequence, can hybridize to the corresponding sequence to form a stem-loop structure and trigger suppression of the Zm.GA20ox3 and Zm.GA20ox5 genes. The insertion site is determined by the design of the guide RNA directing a double-stranded genomic DNA cleavage. Without being bound to any particular theory, the edited Zm.GA20ox3 gene produces a transcript able to form a stem-loop structure which can induce suppression or gene silencing of the wild-type or other alleles of the Zm.GA20ox3 and Zm.GA20ox5 genes. In this example, the inserted Zm.GA20ox5 fragment can be excised from either copy or allele of the endogenous Zm.GA20ox5 gene. This type of editing is called trans-fragment targeting (TFT) editing since the fragment originates from the endogenous Zm.GA20ox5 gene. The boundaries of the excision fragment are defined by a pair of properly designed guide RNAs. According to this example, the inserted Zm.GA20ox5 fragment can also be excised from a donor template which is a double-stranded DNA molecule comprising the desired Zm.GA20ox5 fragment and flanked by target sites for guide RNA(s). The flanking gRNA target sites can be identical, utilizing the same gRNA, or different and according to some embodiments oriented to limit the amount of gRNA target site included in the DNA insertion fragment post cleavage. These target sites can match to the endogenous genome, be artificially-derived, or match to a non-endogenous genome, relative to the endogenous genome of the plant to be edited. According to some embodiments, the target sites flanking the insertion fragment of the donor template to be excised for insertion into the endogenous locus may be heterologous with respect to the native or endogenous genome, such that any off-target DNA cleavage within the endogenous genome can be minimized or eliminated. This method is referred to as "template assist" when performed in combination with guide RNAs targeted for excising a fragment from the endogenous Zm.GA20ox5 locus. Conversely, a Zm.GA20ox3 fragment may be excised via TFT from either copy or allele of the Zm.GA20ox3 gene and/or from a donor template (e.g., template assist method) and inserted into a pre-selected site of the endogenous Zm.GA20ox5 gene to produce an inverted-repeat sequence which can be transcribed into a RNA transcript comprising a stem-loop structure that triggers RNA-mediated suppression or silencing of the wild-type or other alleles of the Zm.GA20ox3 and/or Zm.GA20ox5 genes.

With either of these approaches, however, it is possible for other types of edits or mutations to be formed, such as deletion(s) and/or inversion(s) depending on which DNA cut(s) or break(s) are created at the gRNA or editing target site(s) and the fragment(s) inserted into or between those cut site(s). An inserted DNA fragment may originate from either copy or allele of the Zm.GA20ox3 or Zm.GA20ox5 gene, or from a DNA template molecule. Therefore, a deletion can be generated from cutting one or more target sites, and/or an inversion sequence can be generated by a DNA fragment being inserted in an opposite, reverse or antisense orientation relative to the coding sequence of the edited Zm.GA20 oxidase gene. The inversion may be present in the edited gene with or without a corresponding sequence that when expressed could hybridize to form a RNA hairpin or stem-loop structure with the encoded inversion sequence of the mRNA transcribed from the edited gene. The presence of an antisense inversion sequence without the corresponding sequence and resulting hairpin or stem-loop structure may be sufficient to trigger suppression of one or both of the Zm.GA20ox3 and Zm.GA20ox5 genes through canonical or non-canonical RNA mechanisms.

A plant transformation construct (pMON419922) was designed to create a double stranded break (DSB) in the Zm.GA20ox3 gene to allow for insertion of an antisense DNA fragment of the Zm.GA20ox5 gene either from the endogenous Zm.GA20ox5 locus or an exogenously provided donor template. In this example, the construct generally contains 4 functional regions or cassettes relevant to gene editing and creation of the insertion (e.g., inversion) in the edited gene: expression of a Cpf1 or Cas12a variant protein, expression of three guide RNAs for the Zm.GA20ox3 gene locus, expression of an additional three guide RNAs for the Zm.GA20ox5 gene locus, and a donor template region comprising a Zm.GA20ox5 gene fragment for the template assist method of inserting the Zm.GA20ox5 gene fragment (approximately 400 nucleotides in length) from the donor template. Each guide RNA unit contains a common scaffold compatible with the Cpf1 mutant, and a unique spacer/targeting sequence complementary to its intended target site.

The Cpf1 expression cassette comprises a maize ubiquitin promoter (SEQ ID NO: 25) operably linked to a sequence encoding a Lachnospiraceae bacterium G532R/K595R mutant Cpf1 RNA-guided endonuclease enzyme (SEQ ID NO: 9) fused to two nuclear localization signals (SEQ ID NOs: 10 and 11). See, e.g., Gao, L. et al., Nature Biotechnol. 35(8): 789-792 (2017), the entire contents and disclosure of which are incorporated herein by reference.

One expression cassette comprises a sequence encoding three guide RNAs (two guide RNAs having targeting/spacer sequences encoded by the SP1 and SP2 DNA sequences in Table 2 below (see also FIG. 1) that target two closely spaced-apart sites in exon 1 of the Zm.GA20ox3 gene; and another guide RNA having a targeting/spacer sequence encoded by the SP3 DNA sequence in Table 2 below (see also FIG. 1) targeting a site in exon 1 of the Zm.GA20ox5 gene), operably linked to a maize RNA polymerase III (Pol3) promoter (SEQ ID NO: 12). Spacer sequences SP1 and SP2 target two alternative breakage sites in exon-1 of Zm.GA20ox3 that are spaced apart by about 68 nucleotides, and either breakage site is able to receive a reverse complement insertion fragment, or the insertion fragment could replace the sequence between SP1 and SP2. It is also possible that the insertion fragment could integrate at both SP1 and SP2 target sites.

Another expression cassette comprises a sequence encoding an additional three guide RNAs (two guide RNAs having targeting/spacer sequences encoded by the SP4 and SP5 DNA sequences in Table 2 (see also FIG. 1) that target two closely spaced-apart target sites in exon 1 of the Zm.GA20ox5 gene; and another guide RNA having targeting/spacer sequences encoded by the SP6 DNA sequence in Table 2 (see also FIG. 1) targeting two identical engineered sites flanking the Zm.GA20ox5 gene fragment in the donor template region), operably linked to a synthetic promoter. Spacer sequences SP3 or SP4 target two alternative breakage sites in exon-1 of the endogenous Zm.GA20ox5 gene that are spaced apart by about 83 nucleotides, whereas the spacer sequence SP5 targets another breakage point in exon-1 of the endogenous Zm.GA20ox5 gene spaced apart from the cleavage site for the SP4 spacer by a greater distance of about 577 nucleotides. The targeting/spacer sequence SP6 is derived from a soybean PDS gene that has been separately demonstrated to work in combination with Cpf1 to direct cleavage of a target site in an endogenous PDS gene of a soybean plant.

Another nearly identical plant transformation construct (pMON422388) was designed to create a double stranded break (DSB) in the Zm.GA20ox3 gene to allow for insertion of an antisense DNA fragment of the Zm.GA20ox5 gene, but this second construct did not encode the guide RNA having the targeting/spacer sequence encoded by the SP6 DNA sequence for the template assist method, such that the fragment would originate from an endogenous copy of the Zm.GA20ox5 gene.

With the constructs described in this example, guide RNAs with spacers SP3 and SP4 may work in combination with a guide RNA with spacer SP5 would produce a fragment between about 500 and 700 bp from exon-1 of the endogenous Zm.GA20ox5 gene that could be inserted into a site within exon-1 of the endogenous Zm.GA20ox3 gene in the reverse complementary orientation, such that the RNA molecule transcribed from the endogenous Zm.GA20ox3 gene forms a stem-loop structure in the RNA transcript that can trigger suppression or silencing of the other copy/copies or allele(s) of the endogenous Zm.GA20ox3 and/or Zm.GA20ox5 gene(s). The resulting fragment could be referred to as a SP3-SP5 fragment (SEQ ID NO: 13) or a SP4-SP5 fragment (SEQ ID NO: 14), depending on whether spacer SP3 or SP4 was involved. In addition, a donor template containing a Zm.GA20ox5 gene fragment flanked by two SP6 spacer sequences can produce a Zm.GA20ox5 gene fragment (referred to as a SP6-SP6 fragment (e.g., SEQ ID NO: 26)), if used in combination with the first transformation construct described above containing the SP6 sequence, for insertion into a site within the endogenous Zm.GA20ox3 gene in the reverse complementary orientation.

The DNA sequences encoding the guide RNA spacers and their intended target sites are listed in Table 2.

TABLE 2

Example guide RNAs used for editing the Zm.GA20ox3 locus.

| Guide RNA Spacer | Target Site | Spacer Sequence | SEQ ID |
|---|---|---|---|
| SP1 | GA20ox3_2587 | CTGGAAGGAGACCCTGTCCTTCG | 15 |
| SP2 | GA20ox3_2655 | CCGGCACCCTCGGCCAAGATTTC | 16 |
| SP3 | GA20ox5_428 | CTCCCTGCCTTCGTCTTTGTCGT | 17 |
| SP4 | GA20ox5_511 | CTGCATACTTGCAGCTCGCACAT | 18 |
| SP5 | GA20ox5_1088 | CTGGAAGGAGACCCTGTCGTTCG | 19 |
| SP6 | Template Gm.PDS site | GTAAGAAGCTCTTCACCGTTCCA | 20 | sequencing the PCR products. This first PCR approach was used to determine which type of inverted insertion occurred in the endogenous Zm.GA20ox3 gene (see Tables 3 and 4).

According to a second PCR approach, a PCR primer pair including one primer (SEQ ID NO: 23) hybridizing to a sequence upstream (on the 5' side) of the two guide RNA target sites (SP1 and SP2) in the Zm.GA20ox3 gene and the other primer (SEQ ID NO: 24) hybridizing to a sequence downstream of the two SP1 and SP2 guide RNA target sites, such that a PCR product is generated spanning the possible insertion sites in the Zm.GA20ox3 gene. Thus, the presence and size of the PCR fragment using this approach would show whether an insertion occurred at the target sites, but independent of orientation. The PCR product can also be sequenced to determine the type and orientation of the insertion. According to this second approach, the size/sequence of the PCR product could also be used to determine whether the inserted GA20ox5 fragment originated from the endogenous GA20ox5 locus or the donor template region, and the zygosity of the plant could be determined by whether the wild-type PCR fragment size/sequence was present.

Individual R1 plants produced by selfing R0 plants having one or more of the edits were assayed for the type of insertion and the zygosity of the insertion mutant or allele (see Tables 3 and 4). As used herein, "homo" means homozygous for the mutant allele, and "hetero" means heterozygous for the mutant allele. Tables 3 and 4 further provide the genomic DNA sequence of the coding sequence or region of the edited GA20 oxidase 3 gene from the start to stop codon and the sequence of the inversion or antisense sequence within such coding sequence or region of the edited GA20 oxidase 3 gene (each by SEQ ID NO). To avoid repetition, the inversion type and coding and inversion sequences are only provided in the first row of Tables 3 and 4 for each Edit ID. Edit IDs E270933 and E271059 in Table 3 were generated with the pMON419922 construct, and Edit IDs E376333 and E376314 in Table 4 (and Edit ID E376274) were created using the pMON422388 construct. Additional edits were generated with these constructs, but either were not recovered in R1 plants/seeds, had other T-DNA insertions and/or did not produce small RNAs, and were therefore discarded and not advanced for further testing. Edit ID E376274 created with the pMON422388 construct comprising an inverted GA20ox5 SP4-SP5 fragment inserted into the GA20ox3 SP1 target site was not recovered in R1 plants/seeds and was therefore not advanced. Edit ID Example 2. Confirmation of Inversion Edits in Plants Using the Constructs in Example 1

An inbred corn plant line was transformed via *Agrobacterium*-mediated transformation with one of the transformation vectors described above in Example 1. The transformed plant tissues were grown to produce mature R0 plants. R0 plants having one or more unique genome edit(s) were self-crossed to produce R1 plants. To determine the edits and insertions in the endogenous Zm.GA20ox3 gene of the R0 and R1 plants, one or two PCR assay approaches were performed, with primers designed to identify the size or junctions of the intended insertions. One approach used a PCR primer pair including one primer (SEQ ID NO: 21) hybridizing to a sequence in the inserted Zm.GA20ox5 gene fragment and another primer (SEQ ID NO: 22) hybridizing to a sequence in the endogenous GA20ox3 gene, where the primers are oriented such that a PCR product is generated when the Zm.GA20ox5 gene fragment is inserted in the antisense orientation in the endogenous GA20ox3 gene (i.e., the PCR product was only generated across the 3' end of the inserted fragment when oriented in the inverted antisense direction). If a PCR fragment was generated, then a Zm.GA20ox5 gene fragment was inserted at the target site in the antisense orientation. In addition, whether the inserted Zm.GA20ox5 fragment originated from the endogenous Zm.GA20ox5 locus or the donor template region could also be determined and distinguished by PCR product size and/or E376274 for the GA20 oxidase 3 gene has a genomic coding sequence of SEQ ID NO: 35 and an inversion sequence of SEQ ID NO: 36.

Tables 3 and 4 also provide information about possible simple/small or larger edit(s) or deletion(s) that may be present in the GA20 oxidase 5 gene. Simple or small deletion(s) may also be present in the endogenous GA20 oxidase 5 (GA20ox5) gene at one or more of the individual SP3, SP4 and SP5 target sites, and large deletion(s) may be present in the endogenous GA20ox5 gene spanning between the SP3/SP5 or SP4/SP5 target sites. For the pMON422388 construct, Table 4 provides pooled information and numbers for the R1 plants grouped by Edit ID. As can be seen in Tables 3 and 4, R0 and R1 plants in many cases did contain one or more edits or deletions in the GA20ox5 locus, although some R1 plants (designated as "unknown" in the tables) were not determined to contain an edit or deletion in the GA20ox5 gene. In other cases, the zygosity of an edited GA20ox5 allele was not determined and is therefore designated as "homozygous or heterozygous". However, the edited GA20ox5 alleles present in R0 and R1 plants were removed and segregated away from the edited GA20ox3 alleles in subsequent generations.

TABLE 3

Editing Inversion and Zygosity in R0 and R1 plants for pMON419922

| Edit ID | R1 Plant ID | Editing inversion type | R1 zygosity call for GA20ox3 mutant | GA20ox5 Edit | Genomic Coding Sequence (SEQ ID NO) | Inversion Sequence (SEQ ID NO) |
|---|---|---|---|---|---|---|
| E270933 | P757870 | GA20ox5 SP4-SP5 fragment into GA20ox3 SP1 target site; 6 nucleotide deletion at SP2 | hetero | unknown | 27 | 28 |
| E270933 | P757885 | | hetero | unknown | | |
| E270933 | P758012 | | hetero | unknown | | |
| E270933 | P758049 | | hetero | unknown | | |
| E270933 | P758040 | | hetero | Heterozygous large deletion | | |
| E270933 | P758007 | | hetero | unknown | | |
| E270933 | P757888 | | hetero | Heterozygous large deletion | | |
| E270933 | P757932 | | hetero | Heterozygous large deletion | | |
| E270933 | P757965 | | hetero | unknown | | |
| E270933 | P758046 | | hetero | unknown | | |
| E270933 | P757857 | | hetero | unknown | | |
| E270933 | P757881 | | hetero | unknown | | |
| E270933 | P757925 | | hetero | unknown | | |
| E270933 | P757982 | | hetero | unknown | | |
| E270933 | P757985 | | hetero | Heterozygous large deletion | | |
| E270933 | P758051 | | hetero | unknown | | |
| E270933 | P757886 | | hetero | unknown | | |
| E270933 | P757853 | | hetero | unknown | | |
| E270933 | P757904 | | hetero | unknown | | |
| E270933 | P757956 | | hetero | unknown | | |
| E270933 | P757970 | | hetero | unknown | | |
| E270933 | P757987 | | hetero | unknown | | |
| E270933 | P757962 | | hetero | unknown | | |
| E270933 | P757949 | | hetero | unknown | | |
| E270933 | P758001 | | hetero | unknown | | |
| E270933 | P758004 | | hetero | unknown | | |
| E271059 | P758336 | donor template fragment into GA20ox3 SP1 target site; 9 nucleotide deletion at SP2 | hetero | Homozygous or heterozygous small deletion | 29 | 30 |
| E271059 | P758342 | | hetero | Homozygous or heterozygous small deletion | | |
| E271059 | P758343 | | hetero | Biallelic for small deletions; T-DNA insert | | |

TABLE 3-continued

Editing Inversion and Zygosity in R0 and R1 plants for pMON419922

| Edit ID | R1 Plant ID | Editing inversion type | R1 zygosity call for GA20ox3 mutant | GA20ox5 Edit | Genomic Coding Sequence (SEQ ID NO) | Inversion Sequence (SEQ ID NO) |
|---|---|---|---|---|---|---|
| E271059 | P758349 | | hetero | Homozygous or heterozygous small deletion | | |
| E271059 | P758352 | | hetero | Homozygous small deletion | | |
| E271059 | P758354 | | hetero | Homozygous or heterozygous small deletion | | |
| E271059 | P758355 | | hetero | Homozygous small deletion | | |
| E271059 | P758330 | | hetero | Homozygous or heterozygous small deletion | | |

TABLE 4

Editing Inversion and Zygosity in R0 and R1 plants for pMON422388

| Edit ID | Number of R1 Plants | Editing inversion type | R1 zygosity call for GA20ox3 mutant | GA20ox5 Deletion | Genomic Coding Sequence (SEQ ID NO) | Inversion Sequence (SEQ ID NO) |
|---|---|---|---|---|---|---|
| E376333 | 8 | GA20ox5 SP4-SP5 fragment to GA20ox3 SP2; 7 nucleotide deletion at SP1 | hetero | 4 with large GA20ox5 deletion; 1 with small GA20ox5 deletion; and 3 with both. | 31 | 32 |
| E376333 | 17 | | homo | 2 with large GA20ox5 deletion; 1 with small GA20ox5 deletion; 6 with both; and 8 unknown. | | |
| E376333 | 10 | | homo or hetero | unknown | | |
| E376314 | 8 | GA20ox5 SP4-SP5 fragment to GA20ox3 SP2; 6 nucleotide at SP1 | hetero | unknown | 33 | 34 |
| E376314 | 1 | | homo | unknown | | |
| E376314 | 1 | | homo or hetero | unknown | | |

Example 3. Reduced Plant Height of Corn Plants with Edited Allele

Figure 2:
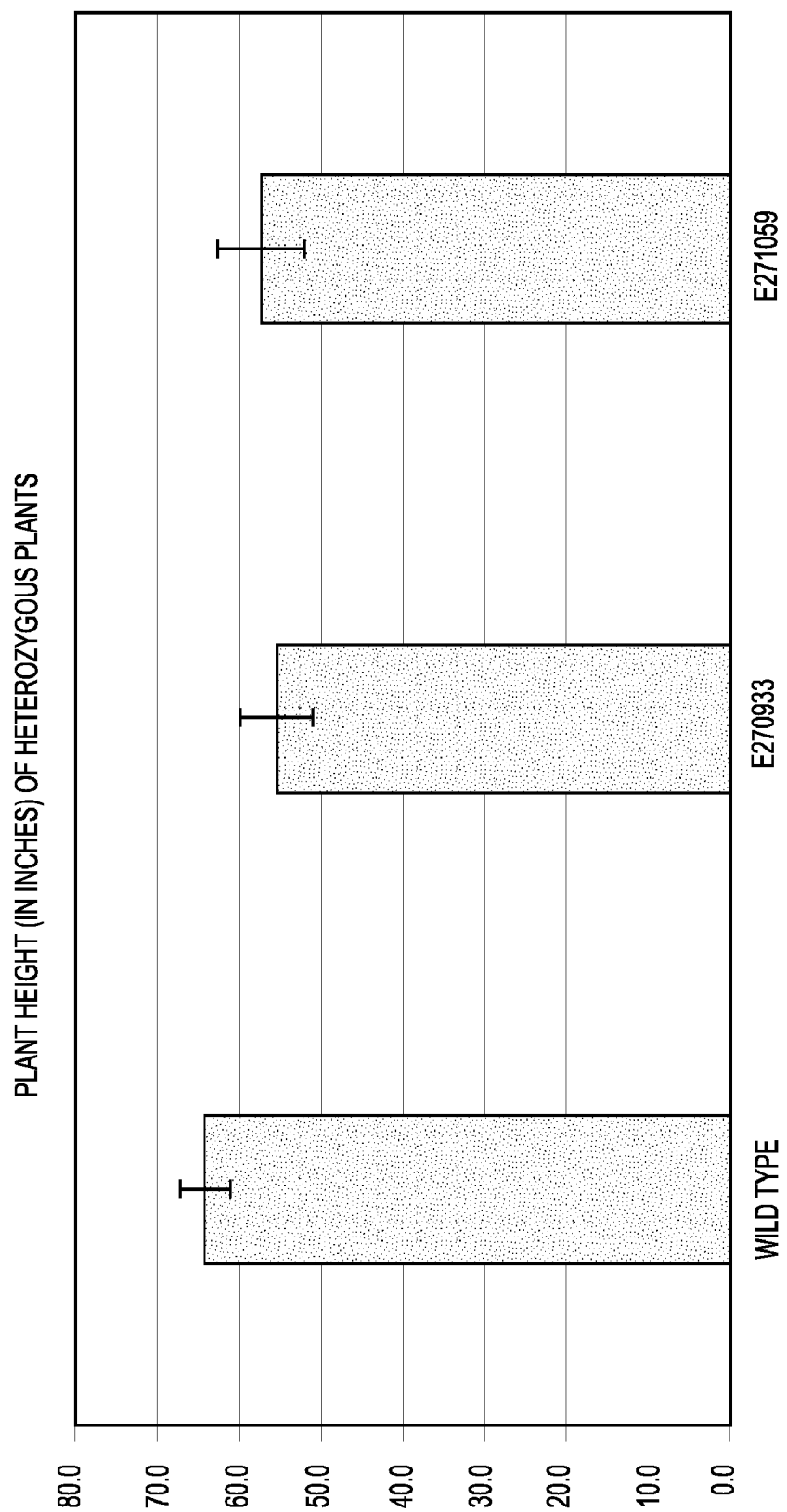
FIG. 2 depicts the average heights of wild type and heterozygous edited corn plants in inches (Y-axis).

R1 corn plants heterozygous for an edited allele of the GA20 oxidase 3 gene with the corresponding inversion identified in Example 2 were grown to maturity to measure their plant heights along with wild type control plants. R1 seeds were planted in soil and grown to maturity in the greenhouse under day/night temperatures of 85° F./70° F. (29.4° C./21.1° C.) and a photoperiod of 16 hours light/8 hours dark using standard nutrient and light conditions for corn plant growth and development. Plant heights (PHT) of these R1 plants were measured at R2 growth stage from the soil level to the base of the uppermost fully expanded leaf. Table 5 provides the plant heights of individual R1 plants heterozygous for one of two hairpin inversion edits, along with wild type control plants. Average plant heights for WT and each edit are also provided (see also FIG. 2 showing the average plant heights with error bars).

These plant heights demonstrate that plants heterozygous for an edited GA20 oxidase 3 allele comprising an inversion sequence have reduced plant heights averaging 54.0 inches or 57.3 inches for the two edited alleles, versus an average plant height of 64.2 inches for the WT control.

The plant height data shown in this example demonstrate that plants heterozygous for an edited allele of the GA20 oxidase 3 gene comprising an antisense inversion sequence have significantly reduced plant heights in comparison to wild type control plants, suggesting that these edited hairpin inversion alleles of the GA20 oxidase 3 gene act in a dominant or semi-dominant manner to produce a reduced plant height phenotype (i.e., semi-dwarf or short stature corn plants), especially since edited loss-of-function alleles of the GA20 oxidase 3 or GA20 oxidase 5 genes alone without an antisense or inversion sequence have been shown to not produce short stature corn plants. See, e.g., Published PCT Application Nos. WO/2019/161149, WO/2019/161147 and WO/2019/161144, the entire contents and disclosures of which are incorporated herein by reference. However, many of these R1 plants may also be homozygous or heterozygous for edited GA20ox5 allele(s) (see Table 3). The presence and zygosity of edited GA20ox5 alleles is unknown for many of the R1 plants, but R1 Plant IDs P758040, P757888, P757932 and P757985 for the E270933 Edit ID were heterozygous for a large deletion in the GA20ox5 gene, R1 Plant ID P758352 was homozygous for a small deletion in the GA20ox5 gene, R1 Plant ID P758343 contained small deletion(s) and a T-DNA insert in the GA20ox5 gene, and P758336 was homozygous or heterozygous for a small deletion in the GA20ox5 gene. Therefore, it is possible that additional mutation(s) in the GA20ox5 gene could also have an effect on R1 plant height. Further plant height measurements will be made in subsequent generations having the edited GA20ox5 alleles removed to confirm the shorter plant height phenotype.

TABLE 5

Plant Heights of R1 plants heterozygous for edited inversion alleles of Zm.GA20ox3

| Edit ID | R1 Plant ID | Plant height (inches) |
| --- | --- | --- |
| E270933 | P757870 | 56.25 |
| E270933 | P757885 | 49.75 |
| E270933 | P758012 | 55 |
| E270933 | P758049 | 48.5 |
| E270933 | P758040 | 54.5 |
| E270933 | P758007 | 62 |
| E270933 | P757888 | 58 |
| E270933 | P757932 | 58 |
| E270933 | P757965 | 52.75 |
| E270933 | P758046 | 56.5 |
| E270933 | P757857 | 61.5 |
| E270933 | P757881 | 63.5 |
| E270933 | P757925 | 53.25 |
| E270933 | P757982 | 56.75 |
| E270933 | P757985 | 50.25 |
| E270933 | P758051 | 50.5 |
| | Edit ID E270933 Average | 55.4 |
| E271059 | P758352 | 54 |
| E271059 | P758343 | 54.5 |
| E271059 | P758336 | 63.5 |
| | Edit ID E271059 Average | 57.3 |
| Wild type | WT 1 | 63.5 |
| Wild type | WT 2 | 63.75 |

TABLE 5-continued

Plant Heights of R1 plants heterozygous for edited inversion alleles of Zm.GA20ox3

| Edit ID | R1 Plant ID | Plant height (inches) |
| --- | --- | --- |
| Wild type | WT 3 | 68.5 |
| Wild type | WT 4 | 61 |
| | Wild type Average | 64.2 |

Example 4. Collection of Samples from R2 or R3 Plants for Molecular Assays

For the E270933 inversion edit from the pMON419922 construct, a R1 plant heterozygous for the E270933 edit (P757982) was selfed (self-pollinated) to obtain selected homozygous R2 plants, which were themselves either (i) self-pollinated to produce homozygous inbred R3 plants or (ii) crossed to another elite parental line to produce heterozygous hybrid R3 plants. For the E376333 inversion edit from the pMON422388 construct, a R1 plant homozygous for the E376333 edit (P127584) containing a large deletion in the GA20ox5 gene was either (i) self-pollinated to produce homozygous inbred R2 plants or (ii) crossed to another elite parental line to produce heterozygous hybrid R2 plants. Edited GA20ox5 alleles present in R1 plants were removed in R2 and R3 plants by segregation and selection. The R3 plants containing the E270933 edit, the R2 plants containing the E376333 edit, and wild type control plants of the same parental lines, were grown under standard conditions in the greenhouse and sampled at V2 growth stage for the molecular assays described below. The plants were cut just above the soil level and the entire above-ground portion of the plants were placed in 50 mL conical tubes and immediately frozen in liquid nitrogen. Each sample contained one or two sibling plants of the same genotype. The number of samples for each assay and genotype are provided in Table 6. The frozen samples were milled and used for the small RNA and GA hormone assays described in Examples 5 and 6 below.

TABLE 6

Description of samples for small RNA and GA hormones assays.

| Editing Construct ID | Edit ID | Parental elite line(s) | Number of samples for small RNA assay | Number of samples for GA hormone assay |
| --- | --- | --- | --- | --- |
| pMON419922 | E270933 | Hybrid | 8 | 10 |
| pMON422388 | E376333 | Hybrid | 5 | 5 |
| pMON419922 | E270933 | Inbred | 9 | 10 |
| pMON422388 | E376333 | Inbred | 9 | 10 |
| Hybrid Wild type | | | 1 | |
| Inbred Wild type | | | 2 | |

Example 5. Detection of Small RNAs in Plants Having an Edited Inversion Allele

To generate small RNA libraries for sequencing, Illumina's TruSeq small RNA Library Preparation Kit was used according to the manufacturer's protocol (Document #15004197v02) with a modification at the library purification step. Samples of each genotype for this small RNA assay experiment are identified in Example 4 above. After amplification of cDNA, individual libraries were gel purified using a 6% Novex TBE PAGE gel for size separation. The gel was stained with 1×SYBR Gold for 20 minutes. The final library product was sequenced on Illumina's NextSeq platform with a minimum depth of 3 million reads per sample. After sequencing, reads were processed through the following steps: the sequencing adapters were trimmed; reads matching housekeeping noncoding RNAs were removed; and libraries were normalized to reads per million. Between 1 and 9 samples per genotype were assayed.

mRNAs expressed from the edited GA20 oxidase 3 genes containing the E270933 and E376333 inversion edits were predicted to produce a hairpin or stem-loop RNA structure comprising the inversion sequence and the native sequence in the GA20 oxidase 3 gene that is complementary and could hybridize to the inversion sequence. Since double stranded RNA hairpins or stem-loop structures can trigger RNA interference (RNAi) and suppression of genes encoding identical or homologous RNA sequences, plants containing the inversion edits were assayed for the presence of small RNAs. RNAi would be expected to produce small RNAs of about 21 nucleotides in length (21-mers) from the stem of the stem-loop structure consisting in this example of the GA20ox5 inversion sequence and the GA20ox3 native sequence.

Figure 3:
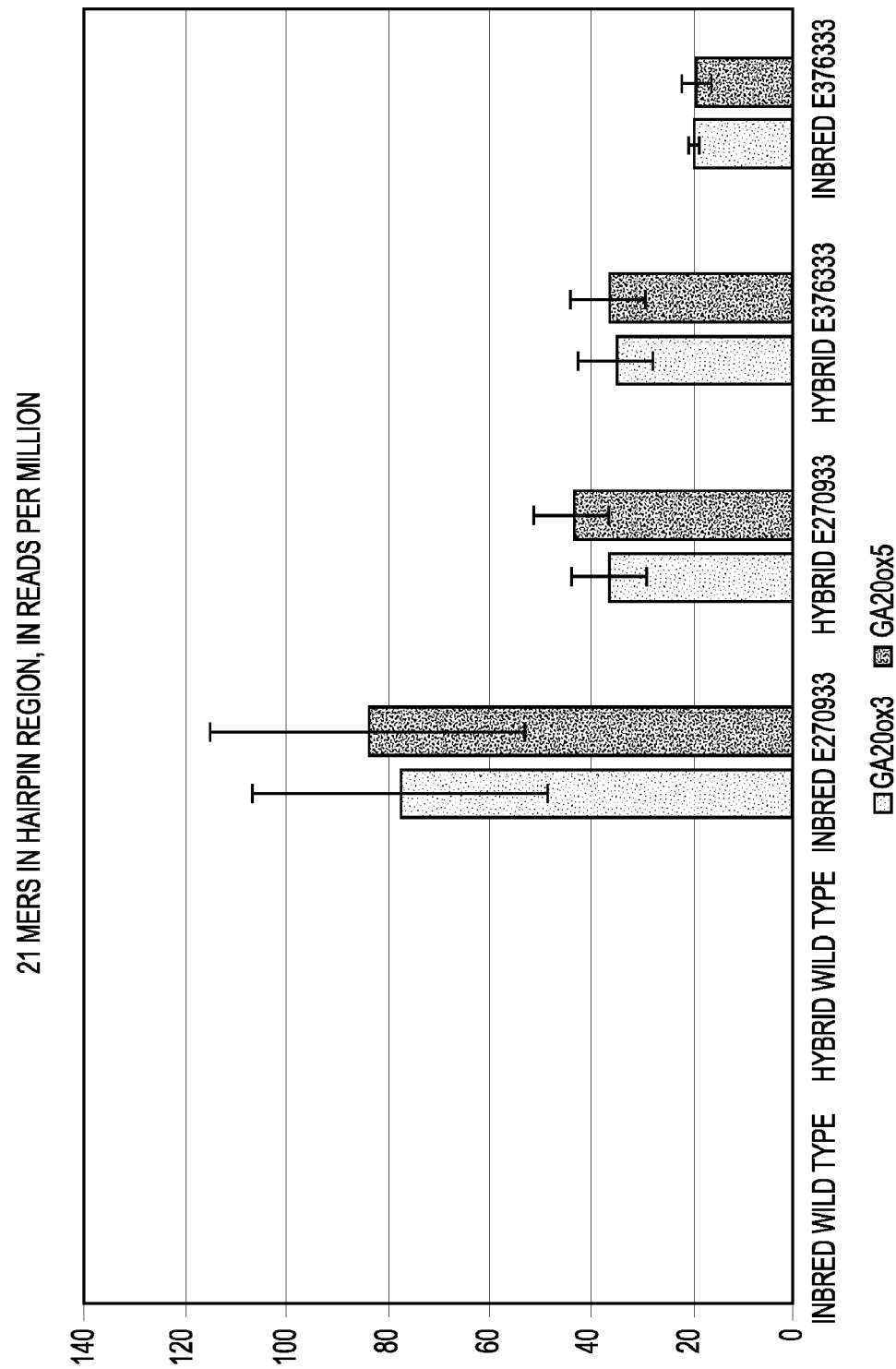
FIG. 3 depicts the number of 21-mer small RNAs (Y-axis) per million reads that mapped to the regions in the stem of the edited stem-loop comprising the inversion sequence from GA20ox5 and a corresponding sequence of the edited GA20ox3 gene that were detected in samples from plants containing edited GA20ox3 alleles.

As shown in FIG. 3, small 21-mer RNAs corresponding to the regions in the stem of the edited stem-loop comprising the inversion sequence from GA20ox5 and a corresponding sequence of the edited GA20ox3 gene were detected in samples from plants containing the edited GA20ox3 alleles indicating the presence of small RNAs in tissues from these edited plants, which were not present in wild type control plants. The abundance of these small RNAs was measured as the number of reads per million total sequencing reads. Small RNAs were present in inbred plants homozygous for the edited allele and hybrid plants heterozygous for the edited allele, with these small RNAs ranging between 19 and 84 reads per million. The abundance of small RNAs appeared consistent with the number of copies of the edited GA20ox3 allele given that heterozygous hybrid plants produced fewer small RNAs than the homozygous inbred plants.

The presence in these samples of small RNAs corresponding to the edited complementary stem region of the edited GA20ox3 gene is consistent with the edited GA20ox3 inversion allele triggering RNAi suppression of the GA20ox3 gene and possibly also the GA20ox5 gene. Additional experiments will determine whether the levels of GA20ox3 and/or GA20ox5 mRNA transcripts are reduced in plants homozygous or heterozygous for edited GA20ox3 or GA20ox5 alleles containing an inversion sequence, relative to controls.

Example 6. Detection of GA Hormones in Plants Having an Edited Inversion Allele

Reduced expression of GA20 oxidase genes can alter the levels of GA hormones in corn plants, which can in turn affect plant height with lower levels of active GAs potentially reducing plant height. The levels of bioactive GA hormones and their precursors were measured in plants containing the edited GA20ox3 alleles. GA20 oxidase is active in the GA biosynthetic pathway and catalyzes the sequential oxidation of metabolic intermediates GA12 and GA53 into GA9 and GA20, respectively (the "early 13-hydroxylation pathway" and "non 13-hydroxylation pathway"). The primary bioactive forms of GA include GA1, GA3 and GA4, which are further downstream of GA20 oxidase activity and the GA9 and GA20 intermediates in the biosynthetic pathway. A reduction or suppression of the expression level and/or enzymatic function of GA20 oxidase genes, as may be expected with the GA20ox3 inversion edits, may result in reduction of downstream metabolites (GA20 and GA9) and accumulation of upstream precursors (GA53 and GA12).

For this experiment, samples were collected as provided in Example 4 above. Freshly frozen plant sample tissues were extracted and cleaned using Waters solid phase extraction MAX cartridge plate. GA hormones and two internal standards were analyzed using UPLC coupled with an ABSciex 5500 Mass Spectrometry with MRM method. The final GA hormone values were calculated based on the calibration curve with ABSciex software Multi-Quan. Each GA hormone calibration curve was in good linear fit, the R2 linear regression was >0.99. The eight technical controls per 96-well plate for each hormone were also included and evaluated in analytical process for meeting the standard criterion. GA levels were measured in terms of pmol/gram of sample tissue.

Figure 4:
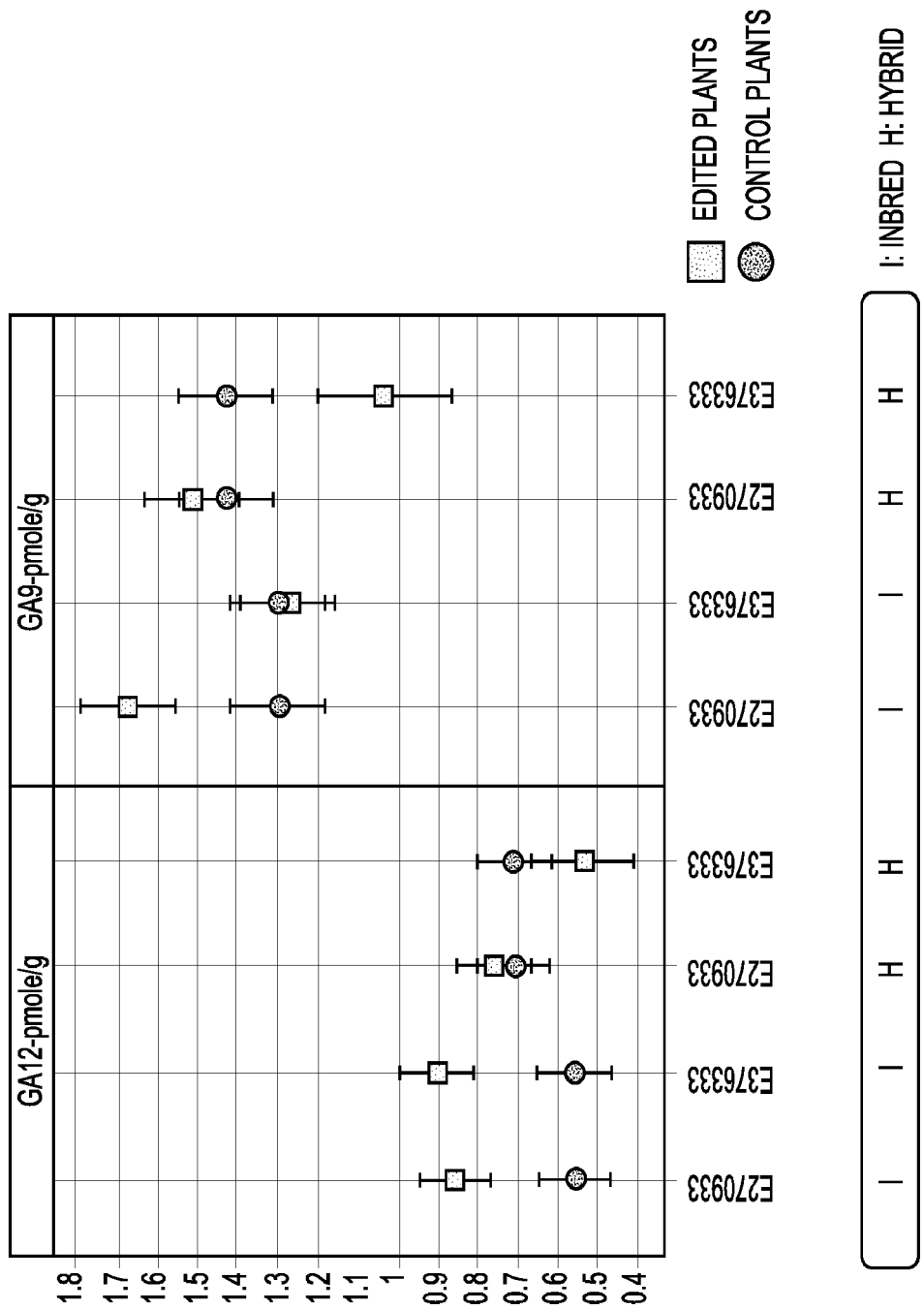
FIG. 4. Depicts the concentrations of GA12 and GA9 in pmole/g (Y-axis) in edited and control corn plants.

As shown in FIG. 4, the levels of GA12 were increased in inbred plants homozygous for the edited allele (E270933 and E376333) but were statistically neutral or unchanged in hybrid plants heterozygous for the edited E270933 and E376333 alleles, relative to wild type control plants. As further shown in FIG. 4, the levels of GA9 were increased in inbred plants homozygous for one of the edited alleles (E270933) but neutral in inbred plants homozygous for the other edited allele (E376333), and the levels of GA9 were neutral (E270933) or decreased (E376333) in hybrid plants heterozygous for the edited allele, each relative to wild type control plants.

Figure 5:
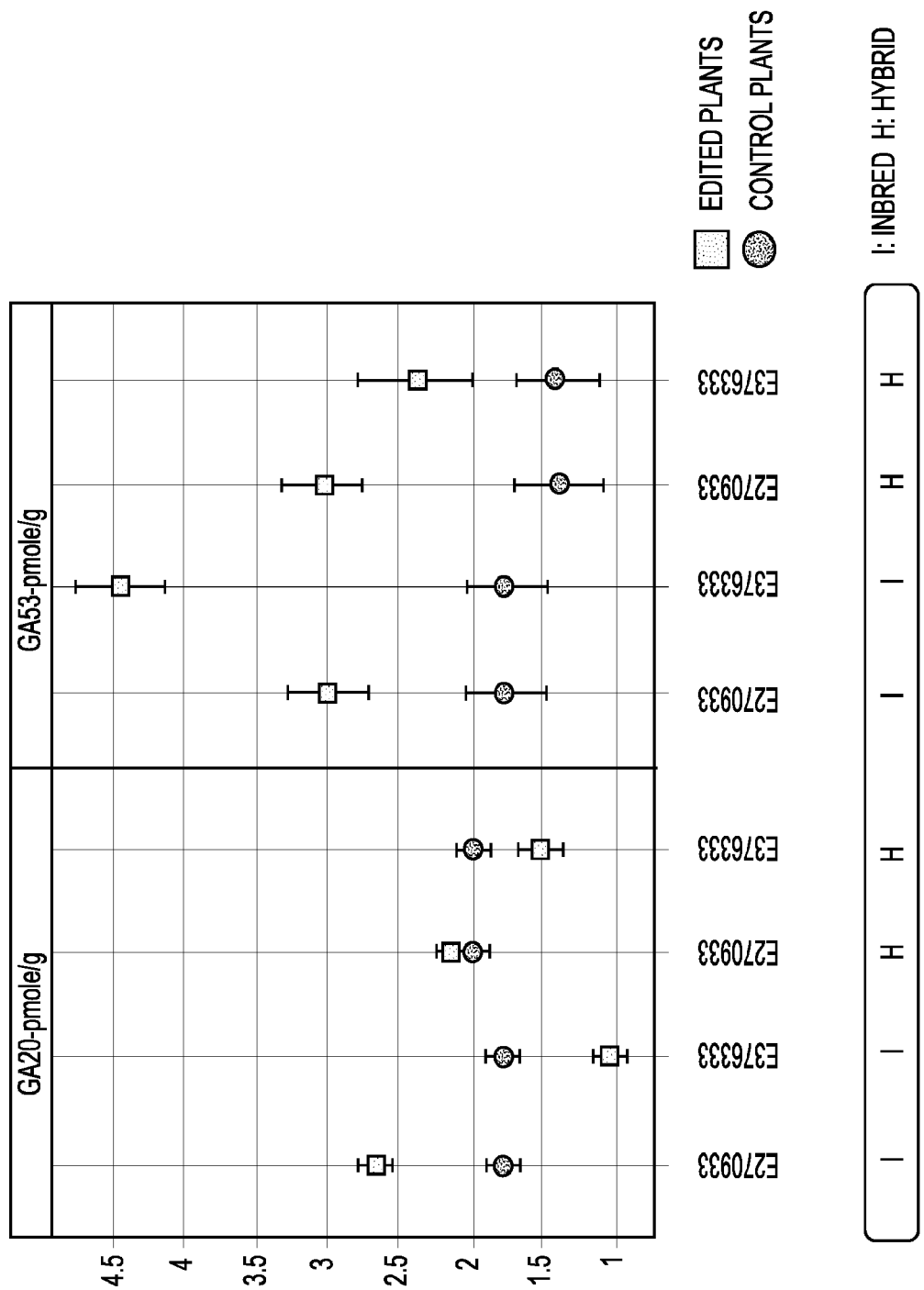
FIG. 5 depicts the concentrations of GA20 and GA53 in pmole/g (Y-axis) in edited and control corn plants.

As shown in FIG. 5, the levels of GA20 were decreased in inbred plants homozygous for one of the edited alleles (E376333) but were increased in inbred plants homozygous for the other edited allele (E270933), and the levels of GA20 were neutral (E270933) or decreased (E376333) in hybrid plants heterozygous for these edited alleles, each relative to wild type control plants. As further shown in FIG. 5, the levels of GA53 were increased in inbred plants homozygous for each edited allele (E270933 and E376333) and in hybrid plants heterozygous for each edited allele (E270933 and E376333), relative to wild type control plants.

Figure 6:
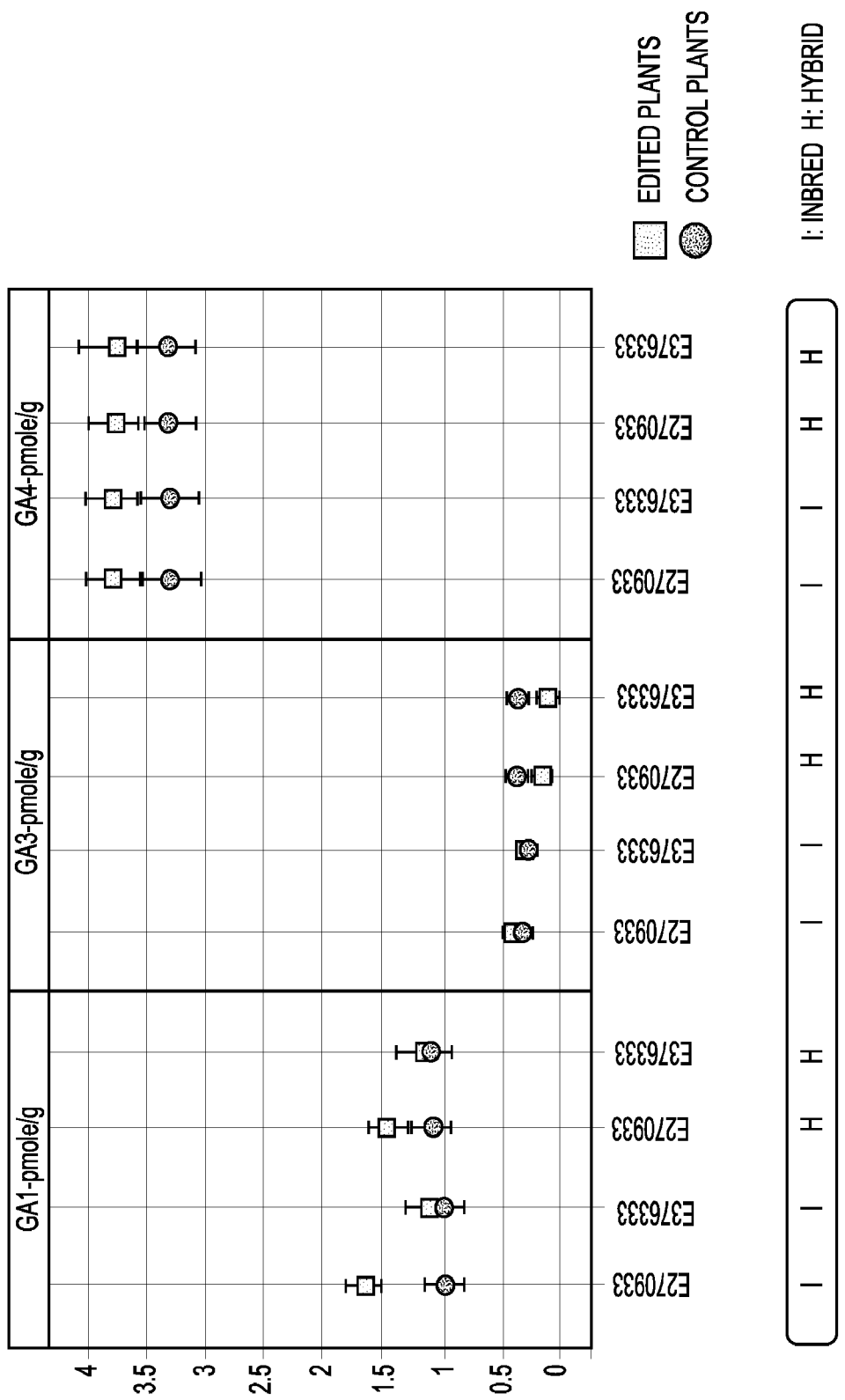
FIG. 6 depicts the concentrations of GA1, GA3, and GA4 in pmole/g (Y-axis) in edited and control corn plants.

FIG. 6 provides the results for levels of active GAs (GA1, GA3 and GA4) measured in samples collected at V2 growth stage of the edited inbred and hybrid plants relative to wild type controls. As shown in FIG. 6, the levels of these active GAs were generally not statistically changed in the inbred and hybrid plants containing each of the edited alleles (E270933 and E376333), except for a small increase in GA4 in inbred plants homozygous for one of the edited alleles (E270933).

These data support the theory that the edited GA20 oxidase 3 gene containing an inversion sequence and encoding a transcript that may form a RNA stem-loop structure is able to affect the levels of GA hormones in inbred and hybrid plants containing the edited alleles. While the data in this experiment are mixed, there is support for increased accumulation of the GA12 and GA53 precursors upstream of GA20 oxidase activity and decreased levels of GA9 and GA20 products of GA20 oxidase activity in plants containing the edited GA20 oxidase 3 allele, although some samples had increased levels of the downstream GA9 and GA20 products. Greater support for decreased GA20 oxidase expression and/or activity with the edited GA20 oxidase 3 alleles is provided in this example by the accumulated levels of upstream GA12 and GA53 precursors. GA12 was neutral to increased in samples from plants with the edited GA20 oxidase 3 allele, and GA53 was increased across all samples from plants having the edited GA20 oxidase 3 allele.

Although the levels of bioactive GAs were not shown to be reduced in this example, this may be due to the early V2 growth stage when the plant tissue samples were collected. The pattern of expression from the endogenous GA20 oxidase 3 locus of transcripts containing the inversion, antisense or stem-loop sequence is also dependent on the endogenous GA20 oxidase 3 gene promoter, which may not drive expression (or expression at a sufficiently high level) at the V2 growth stage to produce a measurable effect on the levels of GA hormones. Without being bound by theory, it is possible that expression of an inversion/hairpin-containing transcript from an edited allele of an endogenous GA20ox3 or GA20ox5 gene under the control of the respective GA20ox3 or GA20ox5 endogenous promoter may be greater at later stages of development and thus have a greater effect on the level(s) of GA hormones at those later stages. The active GAs are also further downstream and not a direct product of GA20 oxidase activity. Future experiments will determine if lower active GA levels are observed at later stages of development in plants heterozygous or homozygous for an edited GA20 oxidase 3 or GA20 oxidase 5 allele. This is supported by the altered levels of GA precursors observed in this example at the early V2 growth stage.

What is claimed is:

1. A modified corn plant, or plant part thereof, comprising a mutant allele of the endogenous GA20 oxidase_3 locus, wherein the mutant allele comprises a DNA segment inserted into the endogenous GA20 oxidase_3 locus, wherein the DNA segment encodes an antisense RNA sequence that is at least 70% complementary to at least 20 consecutive nucleotides of one or more of SEQ ID NOs: 1-3 and 5-7, and wherein the mutant allele of the endogenous GA20 oxidase_3 locus produces a RNA transcript comprising the antisense RNA sequence.

2. The modified corn plant, or plant part thereof, of claim 1, wherein the mutant allele of the endogenous GA20 oxidase_3 locus suppresses the expression of a wild-type allele of the endogenous GA20 oxidase_3 locus, a wild-type allele of the endogenous GA20 oxidase_5 locus, or both.

3. The modified corn plant, or plant part thereof, of claim 1, wherein the RNA transcript further comprises one or more sequence elements of the endogenous GA20 oxidase_3 locus selected from the group consisting of 5' UTR, 1st exon, 1st intron, 2nd exon, 2nd intron, 3rd exon, 3' UTR, and any portion thereof.

4. The modified corn plant, or plant part thereof, of claim 1, wherein:
   a. the DNA segment comprises a nucleotide sequence originating from the endogenous GA20 oxidase_3 locus,
   b. the DNA segment comprises an inverted genomic fragment of the endogenous GA20 oxidase_3 locus,
   c. the DNA segment comprises a nucleotide sequence originating from the endogenous GA20 oxidase_5 locus, or
   d. the DNA segment comprises an inverted genomic fragment of the endogenous GA20 oxidase_5 locus.

5. The modified corn plant, or plant part thereof, of claim 1, wherein:
   a. the antisense RNA sequence is at least 80% complementary to a corresponding endogenous sequence of the RNA transcript, and/or
   b. the corresponding endogenous sequence of the RNA transcript is at least 85% identical to at least 20 consecutive nucleotides of one or more of SEQ ID NOs: 1-3 and 5-7.

6. The modified corn plant, or plant part thereof, of claim 5, wherein the DNA segment is inserted:
   a. within a region selected from the group consisting of 5' untranslated region (UTR), 1st exon, 1st intron, 2nd exon, 2nd intron, 3rd exon and 3' UTR of the endogenous GA20 oxidase_3 locus, and a combination thereof, or
   b. at a genomic site recognized by a targeted editing technique to create a double-stranded break (DSB).

7. The modified corn plant, or plant part thereof, of claim 6, wherein the antisense RNA sequence forms a stem-loop structure with the corresponding endogenous sequence of the RNA transcript.

8. The modified corn plant, or plant part thereof, of claim 6, wherein the inserted DNA segment and the corresponding endogenous DNA segment of the mutant allele are separated by an intervening DNA sequence, wherein the intervening DNA sequence comprises:
   a. a native sequence of the endogenous GA20 oxidase_3 locus, or
   b. an exogenous sequence inserted into the endogenous GA20 oxidase_3 locus.

9. The modified corn plant, or plant part thereof, of claim 5, wherein the mutant allele further comprises a deletion of at least one portion of the endogenous GA20 oxidase_3 locus.

10. The modified corn plant, or plant part thereof, of claim 5, wherein the sense strand of the DNA segment comprises:
    a. a sequence at least 70% complementary to an exon sequence of the endogenous GA20 oxidase_3 or GA20 oxidase_5 locus,
    b. a sequence at least 70% complementary to an untranslated region (UTR) sequence of the endogenous GA20 oxidase_3 or GA20 oxidase_5 locus,
    c. a sequence at least 70% complementary to an exon sequence and an intron sequence of the endogenous GA20 oxidase_3 or GA20 oxidase_5 locus, the exon sequence and the intron sequence being contiguous within the endogenous locus, or
    d. a sequence having at least at least 70% identity to one or more of SEQ ID Nos: 13, 14, 26, 28, 30, 32 and 36, or the complement thereof.

11. The modified corn plant, or plant part thereof, of claim 1, wherein:
   a. the corn plant is homozygous for the mutant allele at the endogenous GA20 oxidase_3 locus, or
   b. the corn plant is heterozygous for the mutant allele at the endogenous GA20 oxidase_3 locus, and wherein
      i. the modified corn plant has a shorter plant height and/or improved lodging resistance relative to an unmodified control plant,
      ii. the level of one or more active GAs in at least one internode tissue of the stem or stalk of the modified corn plant is lower than the same internode tissue of an unmodified control plant, or
      iii. the modified corn plant does not have any significant off-types in at least one female organ or ear.

12. A method for producing a mutant allele of the endogenous GA20 oxidase_3 locus, the method comprising:
   a. generating a double-stranded break in the endogenous GA20 oxidase_3 locus in a corn cell using a targeted editing technique; and
   b. inserting at the double-stranded break a DNA segment, wherein the DNA segment encodes an antisense RNA sequence that is at least 70% complementary to at least 20, consecutive nucleotides of one or more of SEQ ID NOs: 1-3 and 5-7, and wherein the mutant allele of the endogenous GA20 oxidase_3 locus produces a RNA transcript comprising the antisense RNA sequence.

13. The method of claim 12, wherein:
   a. the targeted editing technique comprises the use of at least one site-specific nuclease,
   b. the DNA segment originates from the endogenous GA20 oxidase_3 locus or the endogenous GA20 oxidase_5 locus,
   c. the DNA segment is provided in a donor template, and/or
   d. the method further comprises regenerating or developing a corn plant from the corn cell.

14. The method of claim 12, wherein the mutant allele of the endogenous GA20 oxidase_3 locus is capable of suppressing the expression of a wild-type allele of the endogenous GA20 oxidase_3 locus, a wild-type allele of the endogenous GA20 oxidase_5 locus, or both.

15. The method of claim 12, wherein the DNA segment is inserted within a region selected from the group consisting of 5' untranslated region (UTR), 1st exon, 1st intron, 2nd exon, 2nd intron, 3rd exon and 3' UTR of the endogenous GA20 oxidase_3 locus, and a combination thereof.

16. The method of claim 15, wherein:
   a. the antisense RNA sequence encoded by the inserted DNA segment hybridizes to a corresponding endogenous sequence of the RNA transcript encoded by the corresponding endogenous DNA segment, and/or
   b. the antisense RNA sequence forms a stem loop structure with the corresponding endogenous sequence of the RNA transcript.

17. The method of claim 15, wherein the inserted DNA segment and the corresponding endogenous DNA segment of the mutant allele are separated by an intervening DNA sequence, wherein the intervening DNA sequence comprises:
   a. a native sequence of the endogenous GA20 oxidase_3 locus, or
   b. an exogenous sequence inserted into the endogenous GA20 oxidase_3 locus.

18. The method of claim 15, wherein the sense strand of the DNA segment comprises:
   a. (i) a reverse complement sequence of an exon sequence of the endogenous GA20 oxidase_3 or GA20 oxidase_5 locus, or (ii) a sequence that is at least 70% identical to the reverse complement sequence,
   b. (i) a reverse complement sequence of an untranslated region (UTR) sequence of the endogenous GA20 oxidase_3 or GA20 oxidase_5 locus, or (ii) a sequence that is at least 70% identical to the reverse complement sequence, or
   c. (i) a reverse complement sequence of an exon sequence and an intron sequence of the endogenous GA20 oxidase_3 or GA20 oxidase_5 locus, and wherein the exon sequence and the intron sequence are contiguous within the endogenous locus, or (ii) a sequence that is at least 70% identical to the reverse complement sequence.

19. The method of claim 15, wherein the DNA segment comprises a sequence having at least at least 70% identity to one or more of SEQ ID Nos: 13, 14, 26, 28, 30, 32 and 36.

20. A method for producing a mutant allele of the endogenous GA20 oxidase_3 locus, the method comprising:
   a. generating a first double-stranded break and a second double strand break in the endogenous GA20 oxidase_3 locus in a corn cell using a targeted editing technique; and
   b. inserting a DNA segment between the first double-stranded break and the second double-stranded break, wherein the DNA segment encodes an antisense RNA sequence that is consecutive nucleotides of one or more of SEQ ID NOs: 1-3 and 5-7, and wherein the mutant allele of the endogenous GA20 oxidase_3 locus produces a RNA transcript comprising the antisense RNA sequence.

21. A modified corn plant, or plant part thereof, comprising a mutant allele of the endogenous GA20 oxidase_5 locus, wherein the mutant allele comprises a DNA segment inserted into the endogenous GA20 oxidase_5 locus, wherein the DNA segment encodes an antisense RNA sequence that is at least 70% complementary to at least 20 consecutive nucleotides of one or more of SEQ ID NOs: 1-3 and 5-7, and wherein the mutant allele of the endogenous GA20 oxidase_5 locus produces a RNA transcript comprising the antisense RNA sequence.

22. The modified corn plant, or plant part thereof, of claim 21, wherein the mutant allele of the endogenous GA20 oxidase_5 locus suppresses the expression of a wild-type allele of the endogenous GA20 oxidase_3 locus, a wild-type allele of the endogenous GA20 oxidase_5 locus, or both.

23. The modified corn plant, or plant part thereof, of claim 21, wherein the RNA transcript further comprises one or more sequence elements of the endogenous GA20 oxidase_5 locus selected from the group consisting of 5' UTR, 1st exon, 1st intron, 2nd exon, 2nd intron, 3rd exon, 3' UTR, and any portion thereof.

24. The modified corn plant, or plant part thereof, of claim 21, wherein:
   a. the DNA segment comprises a nucleotide sequence originating from the endogenous GA20 oxidase_3 locus,
   b. the DNA segment comprises an inverted genomic fragment of the endogenous GA20 oxidase_3 locus,
   c. the DNA segment comprises a nucleotide sequence originating from the endogenous GA20 oxidase_5 locus, or
   d. the DNA segment comprises an inverted genomic fragment of the endogenous GA20 oxidase_5 locus.

25. The modified corn plant, or plant part thereof, of claim 21, wherein:
   a. the antisense RNA sequence is at least 80% complementary to a corresponding endogenous sequence of the RNA transcript, and/or
   b. the corresponding endogenous sequence of the RNA transcript is at least 85% identical to at least 20 consecutive nucleotides of one or more of SEQ ID NOs: 1-3 and 5-7.

26. The modified corn plant, or plant part thereof, of claim 25, wherein the DNA segment is inserted:
   a. within a region selected from the group consisting of 5' untranslated region (UTR), 1st exon, 1st intron, 2nd exon, 2nd intron, 3rd exon and 3' UTR of the endogenous GA20 oxidase_5 locus, and a combination thereof, or
   b. at a genomic site recognized by a targeted editing technique to create a double-stranded break (DSB).

27. The modified corn plant, or plant part thereof, of claim 26, wherein the antisense RNA sequence forms a stem-loop structure with the corresponding endogenous sequence of the RNA transcript.

28. The modified corn plant, or plant part thereof, of claim 26, wherein the inserted DNA segment and the corresponding endogenous DNA segment of the mutant allele are separated by an intervening DNA sequence, wherein the intervening DNA sequence comprises:
   a. a native sequence of the endogenous GA20 oxidase_5 locus, or
   b. an exogenous sequence inserted into the endogenous GA20 oxidase_5 locus.

29. The modified corn plant, or plant part thereof, of claim 25, wherein the mutant allele further comprises a deletion of at least one portion of the endogenous GA20 oxidase_5 locus.

30. The modified corn plant, or plant part thereof, of claim 25, wherein the sense strand of the DNA segment comprises:
   a. a sequence at least 70% complementary to an exon sequence of the endogenous GA20 oxidase_3 or GA20 oxidase_5 locus,
   b. a sequence at least 70% complementary to an untranslated region (UTR) sequence of the endogenous GA20 oxidase_3 or GA20 oxidase_5 locus,
   c. a sequence at least 70% complementary to an exon sequence and an intron sequence of the endogenous GA20 oxidase_3 or GA20 oxidase_5 locus, the exon sequence and the intron sequence being contiguous within the endogenous locus, or
   d. a sequence having at least at least 70% identity to one or more of SEQ ID Nos: 13, 14, 26, 28, 30, 32 and 36, or the complement thereof.

31. The modified corn plant, or plant part thereof, of claim 21, wherein:
   a. the corn plant is homozygous for the mutant allele at the endogenous GA20 oxidase_5 locus, or
   b. the corn plant is heterozygous for the mutant allele at the endogenous GA20 oxidase_5 locus, and wherein
      i. the modified corn plant has a shorter plant height and/or improved lodging resistance relative to an unmodified control plant,
      ii. the level of one or more active GAs in at least one internode tissue of the stem or stalk of the modified corn plant is lower than the same internode tissue of an unmodified control plant, or
      iii. the modified corn plant does not have any significant off-types in at least one female organ or ear.

32. A method for producing a mutant allele of the endogenous GA20 oxidase_5 locus, the method comprising:
   a. generating a double-stranded break (DSB) in the endogenous GA20 oxidase_5 locus in a corn cell using a targeted editing technique; and
   b. inserting at the DSB a DNA segment using a targeted editing technique, wherein the DNA segment encodes an antisense RNA sequence that is at least 70% complementary to at least 20 consecutive nucleotides of one or more of SEQ ID NOs: 1-3 and 5-7, and wherein the mutant allele of the endogenous GA20 oxidase_5 locus produces a RNA transcript comprising the antisense RNA sequence.

33. The method of claim 32, wherein:
   a. the targeted editing technique comprises the use of at least one site-specific nuclease,
   b. the DNA segment originates from the endogenous GA20 oxidase_3 locus or the endogenous GA20 oxidase_5 locus,
   c. the DNA segment is provided in a donor template, or
   d. the method further comprises regenerating or developing a corn plant from the corn cell.

34. The method of claim 32, wherein the mutant allele of the endogenous GA20 oxidase_5 locus is capable of suppressing the expression of a wild-type allele of the endogenous GA20 oxidase_3 locus, a wild-type allele of the endogenous GA20 oxidase_5 locus, or both.

35. The method of claim 32, wherein the DNA segment is inserted within a region selected from the group consisting of 5' untranslated region (UTR), 1st exon, 1st intron, 2nd exon, 2nd intron, 3rd exon and 3' UTR of the endogenous GA20 oxidase_5 locus, and a combination thereof.

36. The method of claim 35, wherein:
   a. the antisense RNA sequence encoded by the inserted DNA segment hybridizes to a corresponding endogenous sequence of the RNA transcript encoded by the corresponding endogenous DNA segment, and/or
   b. the antisense RNA sequence forms a stem loop structure with the corresponding endogenous sequence of the RNA transcript.

37. The method of claim 35, wherein the inserted DNA segment and the corresponding endogenous DNA segment of the mutant allele are separated by an intervening DNA sequence, wherein the intervening DNA sequence comprises:
   a. a native sequence of the endogenous GA20 oxidase_5 locus, or
   b. an exogenous sequence inserted into the endogenous GA20 oxidase_5 locus.

38. The method of claim 35, wherein the sense strand of the DNA segment comprises:
   a. (i) a reverse complement sequence of an exon sequence of the endogenous GA20 oxidase_3 or GA20 oxidase_5 locus, or (ii) a sequence that is at least 70% identical to the reverse complement sequence,
   b. (i) a reverse complement sequence of an untranslated region (UTR) sequence of the endogenous GA20 oxidase_3 or GA20 oxidase_5 locus, or (ii) a sequence that is at least 70% identical to the reverse complement sequence, or
   c. (i) a reverse complement sequence of an exon sequence and an intron sequence of the endogenous GA20 oxidase_3 or GA20 oxidase_5 locus, and wherein the exon sequence and the intron sequence are contiguous within the endogenous locus, or (ii) a sequence that is at least 70% identical to the reverse complement sequence.

39. The method of claim 35, wherein the DNA segment comprises a sequence having at least at least 70% identity to one or more of SEQ ID Nos: 13, 14, 26, 28, 30, 32 and 36.

40. A method for producing a mutant allele of the endogenous GA20 oxidase_5 locus, the method comprising:
   a. generating a first double-stranded break and a second double strand break in the endogenous GA20 oxidase_5 locus in a corn cell using a targeted editing technique; and
   b. inserting a DNA segment between the first double-stranded break and the second double-stranded break, wherein the DNA segment encodes an antisense RNA sequence that is consecutive nucleotides of one or more of SEQ ID NOs: 1-3 and 5-7, and wherein the mutant allele of the endogenous GA20 oxidase_5 locus produces a RNA transcript comprising the antisense RNA sequence.

41. A method for generating a corn plant comprising:
   a. fertilizing at least one female corn plant with pollen from a male corn plant, wherein the at least one female corn plant and/or the male corn plant comprise(s) a mutant allele of an endogenous GA20 oxidase locus, wherein the mutant allele comprises a DNA segment inserted into the endogenous GA20 oxidase locus, wherein the DNA segment encodes an antisense RNA sequence that is at least 70% complementary to at least 20 consecutive nucleotides of one or more of SEQ ID NOs: 1-3 or 5-7, and wherein the mutant allele of the endogenous GA20 oxidase locus produces a RNA transcript comprising the antisense RNA sequence; and
   b. obtaining at least one seed produced by said fertilizing of step (a).

42. The method of claim 41, wherein said method further comprises (c) growing said at least one seed obtained in step (b) to generate at least one progeny corn plant comprising said mutant allele.

43. A modified corn plant part, corn cell, or corn tissue comprising a mutant allele of the endogenous GA20 oxidase_3 locus, wherein the mutant allele comprises a DNA segment inserted into the endogenous GA20 oxidase_3 locus, wherein the DNA segment encodes an antisense RNA sequence that is at least 70% complementary to at least 20 consecutive nucleotides of one or more of SEQ ID NOs: 1-3 and 5-7, and wherein the mutant allele of the endogenous GA20 oxidase_3 locus produces a RNA transcript comprising the antisense RNA sequence.

44. A modified corn plant part, corn cell, or corn tissue comprising a mutant allele of the endogenous GA20 oxidase_5 locus, wherein the mutant allele comprises a DNA segment inserted into the endogenous GA20 oxidase_5 locus, wherein the DNA segment encodes an antisense RNA sequence that is at least 70% complementary to at least 20 consecutive nucleotides of one or more of SEQ ID NOs: 1-3 and 5-7, and wherein the mutant allele of the endogenous GA20 oxidase_5 locus produces a RNA transcript comprising the antisense RNA sequence.

* * * * *